US012681018B2

(12) United States Patent
Beck et al.

(10) Patent No.: US 12,681,018 B2

(45) Date of Patent: Jul. 14, 2026

(54) PHOTOACTIVE FLUORESCENT COMPOUNDS AND USE THEREOF FOR LABELING OF PROTEINS

(71) Applicant: EIKON THERAPEUTICS, INC., Hayward, CA (US)

(72) Inventors: Hilary Plake Beck, Emerald Hills, CA (US); David Trombley Mcswiggen, Berkeley, CA (US); Leah Brigit Cleary, Oakland, CA (US); Daniel James Anderson, Redwood City, CA (US); Yihong Li, San Bruno, CA (US); Anne Ruth Sizemore, Scranton, PA (US)

(73) Assignee: EIKON THERAPEUTICS, INC., Hayward, CA (US)

( * ) Notice: Subject to any disclaimer, the term of this patent is extended or adjusted under 35 U.S.C. 154(b) by 776 days.

(21) Appl. No.: 17/873,828

(22) Filed: Jul. 26, 2022

(65) Prior Publication Data

US 2023/0086732 A1 Mar. 23, 2023

Related U.S. Application Data

(60) Provisional application No. 63/339,707, filed on May 9, 2022, provisional application No. 63/226,141, filed on Jul. 27, 2021.

(51) Int. Cl.

| | |
|---|---|
| ***G01N 33/58*** | (2006.01) |
| ***C09B 11/24*** | (2006.01) |
| ***C09B 11/28*** | (2006.01) |
| ***C09K 11/06*** | (2006.01) |

(52) U.S. Cl.

CPC ............ *G01N 33/582* (2013.01); *C09B 11/24* (2013.01); *C09B 11/28* (2013.01); *C09K 11/06* (2013.01); *C09K 2211/1007* (2013.01); *C09K 2211/1018* (2013.01)

(58) Field of Classification Search

CPC ........ A61K 31/416; A61P 21/04; A61P 25/28; A61P 9/00; A61P 37/06; A61P 13/10; A61P 13/00; C07D 209/12; C07D 209/30; C07D 209/40; C07D 209/42; C07D 209/48; C07D 231/56; C07D 401/04; C07D 401/06; C07D 401/12; C07D 401/14; C07D 403/04; C07D 403/06; C07D 403/12; C07D 405/12; C07D 471/04; C07D 487/04

USPC .......................................... 548/953; 514/403

See application file for complete search history.

(56) References Cited

U.S. PATENT DOCUMENTS

| | | |
|---|---|---|
| 10,161,932 B2 | 12/2018 | Lavis et al. |
| 2021/0054001 A1 | 2/2021 | Lavis et al. |
| 2021/0171490 A1 | 6/2021 | Lavis et al. |

FOREIGN PATENT DOCUMENTS

| | | |
|---|---|---|
| WO | WO 2017/201531 A1 * | 11/2012 |
| WO | WO 2015/153813 A * | 10/2015 |
| WO | WO 2015/153813 A1 | 10/2015 |
| WO | WO 2018/046753 A1 | 3/2018 |
| WO | WO 2018/182811 A1 | 10/2018 |

OTHER PUBLICATIONS

Vandemoortele et al., “Review: Pick a Tag and Explore the Functions of Your Pet Protein”, Trends in Biotechnology, Oct. 2019, vol. 37, No. 10, pp. 1078-1090; https://doi.org/10.1016/j.tibtech.2019.03.016 (Year: 2019).*

Toseland, “Fluorescent Labeling And Modification Of Proteins”, J Chem Biol. Jul. 2013; 6(3): 85-95; doi: 10.1007/s12154-013-0094-5) (Year: 2013).*

Jradi et al., “Chemistry of Photosensitive Fluorophores for Single-Molecule Localization Microscopy”, ACS Chemical Biology 2019, 14(6), 1077-1090DOI: 10.1021/acschembio.9b00197 (Year: 2019).*

Berge et al., “Pharmaceutical Salts”, J. Pharm. Sci. Jan. 1977; 66(1):1-19. doi: 10.1002/jps.2600660104. PMID: 833720. (Year: 1977).*

Zhang et al., “Live-Cell Imaging at the Nanoscale With Bioconjugatable and Photoactivatable Fluorophores,” Bioconjugate Chemistry (2020), 31(4), 1052-1062; (Year: 2020).*

Grimm et al., “A General Method to Fine-Tune Fluorophores for Live-Cell and In Vivo Imaging”, Nat Methods. Oct. 2017; 14(10):987-994. (Year: 2017).*

Grimm et al., Nat Methods. Mar. 2015 ; 12(3): 244-250, doi:10.1038/nmeth.3256) (Year: 2015).*

(Continued)

*Primary Examiner* — Jeffrey H Murray

*Assistant Examiner* — Grace Ching Hsu

(74) *Attorney, Agent, or Firm* — Jones Day

(57) ABSTRACT

Provided herein are novel photoactive fluorescent compounds of Formula (A) or a salt, a single stereoisomer, a mixture of stereoisomers or an isotopic form thereof, wherein G, R, X, Z, and $L_A$ are as defined herein, and their use in labeling proteins, for example, tagged proteins, comprising their use for visualizing the location and dynamics of proteins in living cells:

(A)

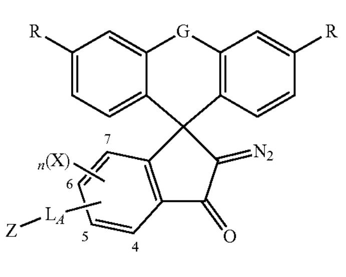

10 Claims, 6 Drawing Sheets

(56) References Cited

OTHER PUBLICATIONS

Butkevich et al., 2017, "Hydroxylated Fluorescent Dyes for Live-Cell Labeling: Synthesis, Spectra and Super-Resolution STED** Microscopy", Chemistry—A European Journal 23(50):12114-12119.
Deo et al., 2021, "The HaloTag as a general scaffold for far-red tunable chemigenetic indicators", Nature Chemical Biology, 17:718-723.
Grimm et al., 2016, "Bright Photoactivatable Fluorophores for Single-Molecule Imaging", Nature Methods, 13(12):985-988.
Grimm et al., 2017, "General Synthetic Method for Si-Fluoresceins and Si-Rhodamines", ACS Central Science 3(9):975-985.
International Search Report and Written Opinion for International Application No. PCT/US2022/038317, mailed Oct. 24, 2022.
Zhang et al., 2020, "Live-Cell Imaging at the Nanoscale with Bioconjugatable and Photoactivatable Fluorophores", Bioconjugate Chemistry, 31(4):1052-1062.
Grimm et al., 2020, "Deuteration improves small-molecule fluorophores," BioRxiv preprint, available at https://doi.org/10.1101/2020.08.17.250027.
Grimm et al., 2021, "A General Method to Improve Fluorophores Using Deuterated Auxochromes," JACS Au 1(5):690-696.

* cited by examiner

PHOTOACTIVE FLUORESCENT COMPOUNDS AND USE THEREOF FOR LABELING OF PROTEINS

1. CROSS REFERENCE TO RELATED APPLICATIONS

This application claims the benefit of U.S. Provisional Application No. 63/226,141 filed on Jul. 27, 2021 and U.S. Application No. 63/339,707 filed on May 9, 2022, the disclosure of each of which is incorporated herein by reference in its entirety.

2. FIELD

Provided herein are novel photoactive fluorescent compounds and their use in labeling proteins, for example, tagged proteins, and their use for visualizing the location and dynamics of proteins in living cells.

3. BACKGROUND

Fluorescence microscopy is useful in visualizing the location and dynamics of biomolecules in living cells. The process involves the labeling of biomolecules with bright, photostable fluorescent dyes that absorb photons and then emit them at a different wavelength. Green Fluorescent Protein (GFP) and other genetically encoded fluorophores were previously the gold standard of fluorescent imaging because they allowed labeling with genetic specificity. A number of efforts were undertaken to improve the proteinaceous dyes by enhancing photostability and other properties; such efforts included enzyme-based self-labeling tags such as HaloTag, which allowed the labeling of specific protein fusions with synthetic fluorophores and enabled diverse imaging experiments inside living cells. See U.S. Pat. No. 10,161,932.

The rhodamine dyes have been and remain in widespread use due to, among other properties, their brightness and photostability. The rhodamines' photophysics are known because of their importance as, inter alia, biological probes. See Grimm et al., "Deuteration Improves Small-Molecule Fluorophores," 2020, BioRxiv preprint, available at https://doi.org/10.1101/2020.08.17.250027 (Grimm et al., 2020). Methods that increase the brightness and photostability of fluorophores have been described. Such methods include the incorporation of deuterium into the alkylamino auxochromes of the rhodamines and other dyes. See Grimm et al., "A General Method to Improve Fluorophores Using Deuterated Auxochromes," *JACS Au* 2021, 1(5), 690-696 (Grimm et al., 2021). However, the rhodamine dyes do not have cell permeability properties that would allow optimized live-cell labeling experiments. See U.S. Pat. No. 10,161,932.

In an effort to enhance cell permeability and improve brightness, azetidine-substituted fluorescent compounds were developed. Such compounds include molecules that are azetidine-substituted derivatives of known fluorescent tags. These compounds can display greater quantum yields compared to their parent compounds. See U.S. Pat. No. 10,161,932. Subsequently, the fluorescence quantum yield of rhodamine and other dyes was improved by incorporating deuterium into their alkylamino substituents. However, deuteration was found to prevent or slow unfavorable characteristics such as photochemically-induced spectral shifts and irreparable photobleaching. See Grimm et al., 2020.

Thus, there remains a need for photoactive fluorescent compounds with improved photostability, brightness, labeling specificity, control of density, and other properties for use in labeling proteins, and this disclosure addresses this need.

4. SUMMARY

In one aspect, provided herein is a compound of Formula (I):

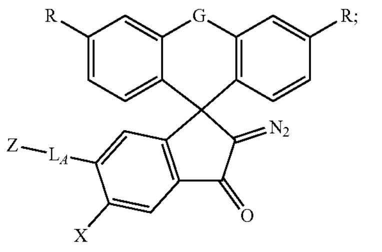

(I)

or a salt, a single stereoisomer, a mixture of stereoisomers or an isotopic form thereof, wherein:

G is —O—, —S—, —$SO_2$—, —$C(C_{1-3}$ alkyl$)_2$-, —$N(C_{1-3}$ alkyl)-, —$Si(C_{1-3}$ alkyl$)_2$-, —P(═O)(OH)—, —P(═O)($C_{1-3}$ alkyl)-, or —P(═O)(Ph)-;

R is

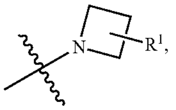

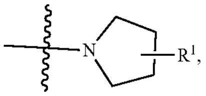

or

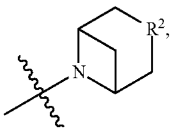

wherein:

$R^1$ is —OH, —C(═O)OH, —C(═O)O($C_{1-3}$ alkyl), —C(═O)N($C_{1-3}$ alkyl$)_2$, —N($C_{1-3}$ alkyl$)_2$, —$(CH_2)_n$O($C_{1-3}$ alkyl),

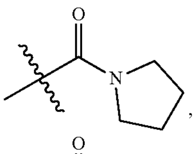

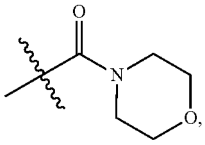

or

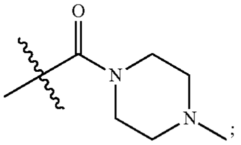

where n is an integer from 1-3;

$R^2$ is —O— or —N($C_{1-3}$ alkyl)-;

X is hydrogen or halogen;

$L_A$ is a linker; and

Z comprises a moiety that covalently bonds to a tagged protein.

In certain embodiments, the tagged protein comprises a HaloTag, SNAP-tag, or CLIP-tag.

In certain embodiments, $L_A$ is a linker of the following Formula (IA):

$$-(L^2)_b-(L^1)_a- \quad \text{(IA);}$$

wherein each $L^1$ is independently:

(i) —$C_{1-6}$-alkylene-, —$C_{1-6}$-alkenylene-, or —$C_{1-6}$-alkynylene-;

(ii) a heteroaryl; or (iii) —NHC(O)—, —C(O)NH—, —OC(O)—, —C(O)O—, —N($C_{1-3}$ alkyl)-C(O)—, —C(O)—N($C_{1-3}$ alkyl)-, —$C_{1-6}$-alkylene-NH—, —NH—$C_{1-6}$-alkylene-, —$C_{1-6}$-alkylene-O—, —O—$C_{1-6}$-alkylene-, —C(O)—$C_{1-6}$-alkylene-, or —$C_{1-6}$-alkylene-C(O)—;

each $L^2$ is independently —$C_{1-6}$-alkylene-, —$(OCH_2)_p$, —$(CH_2O)_p$—, —$(OCH_2CH_2)_p$—, or —$(CH_2CH_2O)_p$—;

p is an integer of 1 to 3;

a and b are each independently an integer of 1 or 2; and wherein $L^1$ and $L^2$ are in an orientation such that $-(L^2)_b-$ is bonded to Z in Formula (I).

In certain embodiments, Z is

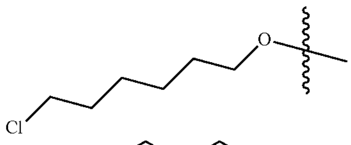

,

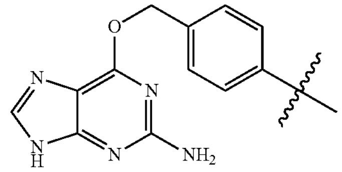

,

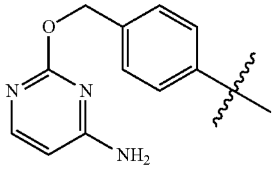

, or

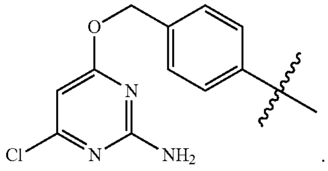

.

In another aspect, provided herein is a method of labeling a protein, comprising contacting a sample comprising a tagged protein with a compound of Formula (I), so as to yield a labeled protein.

5. BRIEF DESCRIPTION OF THE FIGURES

FIG. 1 provides a schematic of specificity, brightness and density control for a commercial non-photoactivatable dye, Janelia Fluor® 549 ($JF_{549}$), a commercial photoactivatable dye (PA-$JF_{549}$), and an hypothetical ideal dye.

Figure 5:
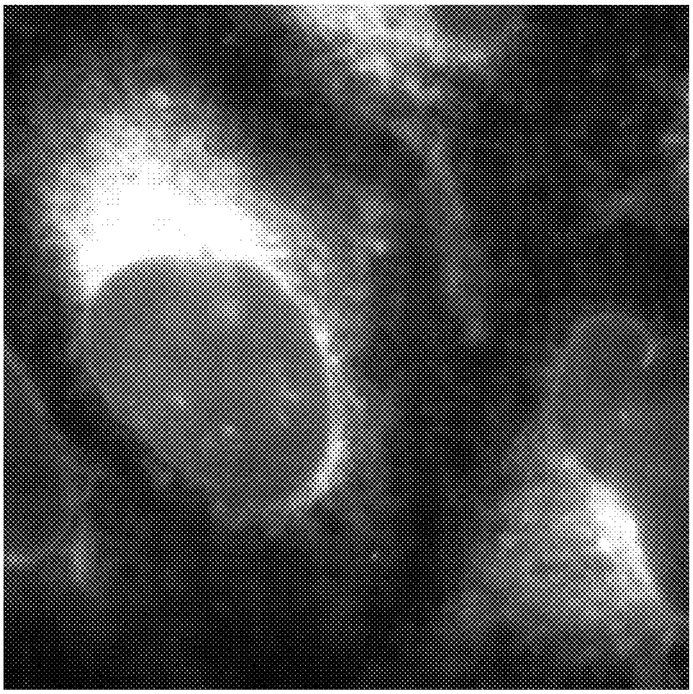

FIG. 5 shows an example field of view ER-HaloTag Fusion expressing U2OS, co-stained with Potomac Red (CAS: 2127150-65-4; Grimm et al., 2017). Labelling specificity of the photoactivatable dye compound of Example 4 was measured and compared to PA-$JF_{549}$.

Figure 6:
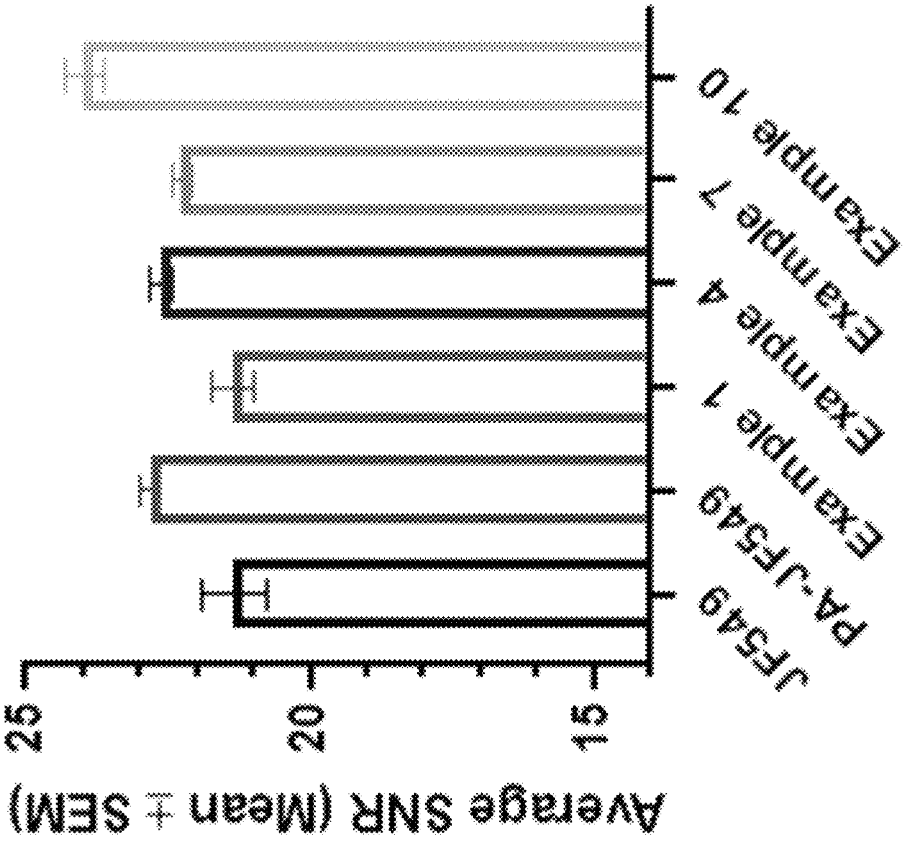

FIG. 6 shows signal to noise ratio (SNR) for $JF_{549}$, PA-$JF_{549}$, and photoactivatable dye compounds of Examples 1, 4, 7, and 10.

6. DETAILED DESCRIPTION

6.1 Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

As used herein, the term "or" is to be interpreted as an inclusive "or" meaning any one or any combination. Therefore, "A, B or C" means any of the following. "A; B; C; A and B; A and C; B and C; A, B and C". An exception to this definition will occur only when a combination of elements, functions, steps or acts are in some way inherently mutually exclusive.

As used herein, the term "about" or "approximately" means an acceptable error for a particular value as determined by those skilled in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the term "salt(s)" refers to a salt prepared from a non-toxic acid or base including an inorganic acid and base and an organic acid and base. Suitable base addition salts of the compounds disclosed herein, include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art.

As used herein and unless otherwise indicated, the term "stereoisomer" or "stereomerically pure" means one stereoisomer of a compound disclosed herein that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereomerically pure forms of such compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques et al., *Enantiomers, Racemates and Resolutions* (Wiley Interscience, New York, 1981); Wilen et al., *Tetrahedron* 33:2725 (1977); Eliel, E. L., *Stereochemistry of Carbon Compounds* (McGraw Hill, N Y, 1962); and Wilen, *Tables of Resolving Agents and Optical Resolutions* p. 268 (E. L. Eliel, Ed., Univ. of Notre Dame Press, Notre Dame, IN, 1972).

It should also be noted that the compounds disclosed herein can include E and Z isomers, or a mixture thereof, and cis and trans isomers or a mixture thereof. In certain embodiments, the compounds disclosed herein are isolated as either the E or Z isomer. In other embodiments, the compounds disclosed herein are a mixture of the E and Z isomers.

The term "isotopic form" or "isotope" as used herein means that, for example, the compounds may be radiolabeled with radioactive isotopes, such as for example tritium (3H), iodine-125 ($^{125}I$), sulfur-35 ($^{35}S$), or carbon-14 ($^{14}C$), or may be isotopically enriched, such as with carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are carbon-13, or nitrogen-15 enriched compounds. As used herein, "deuterated", means a compound wherein at least one hydrogen (H) has been replaced by deuterium (indicated by D or $^{2}H$), that is, the compound is enriched in deuterium in at least one position.

"Alkyl," as used herein, refers to a straight or branched saturated hydrocarbon group containing from 1-10 carbon atoms. In certain embodiments, alkyl includes one carbon atom ("$C_1$ alkyl"). In certain embodiments, alkyl includes 1-2 carbon atoms ("$C_{1-2}$ alkyl"). In certain embodiments, alkyl includes 1-3 carbon atoms ("$C_{1-3}$ alkyl"). In certain embodiments, alkyl includes 1-4 carbon atoms ("$C_{1-4}$ alkyl"). In certain embodiments, alkyl includes 1-6 carbon atoms ("$C_{1-6}$ alkyl"). In certain embodiments, alkyl includes 1-10 carbon atoms ("$C_{1-10}$ alkyl"). In certain embodiments, alkyl includes methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, or n-decyl.

"Alkylene," as used herein, refers to a straight or branched saturated divalent hydrocarbon group containing from 1-10 carbon atoms, and in certain embodiments includes 1-6 carbon atoms. In certain embodiments, alkylene includes 1-3 carbon atoms ("$C_{1-3}$ alkylene"). In certain embodiments, alkylene includes 1-4 carbon atoms ("$C_{1-4}$ alkylene"). In certain embodiments, alkylene includes 1-6 carbon atoms ("$C_{1-6}$ alkylene"). In certain embodiments, alkylene includes 1-10 carbon atoms ("$C_{1-10}$ alkylene").

"Alkenylene," as used herein, refers to a straight or branched chain alkenyl group with one hydrogen removed, thereby rendering this group divalent. In certain embodiments, alkenylene includes 1-3 carbon atoms ("$C_{1-3}$ alkenylene"). In certain embodiments, alkenylene includes 1-4 carbon atoms ("$C_{1-4}$ alkenylene"). In certain embodiments, alkenylene includes 1-6 carbon atoms ("$C_{1-6}$ alkenylene"). In certain embodiments, alkenylene includes 1-10 carbon atoms ("$C_{1-10}$ alkenylene"). Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. The alkenylene group may be unsubstituted or substituted (e.g., optionally substituted alkenylene) as described for alkyl.

"Alkynylene," as used herein, refers to a straight-chain or branched-chain divalent substituent including one or two carbon-carbon triple bonds and containing only C and H when unsubstituted. In certain embodiments, alkynylene includes 1-3 carbon atoms ("$C_{1-3}$ alkynylene"). In certain embodiments, alkynylene includes 1-4 carbon atoms ("$C_{1-4}$ alkynylene"). In certain embodiments, alkynylene includes 1-6 carbon atoms ("$C_{1-6}$ alkynylene"). In certain embodiments, alkynylene includes 1-10 carbon atoms ("$C_{1-10}$ alkynylene"). Non-limiting examples of the alkynylene groups include ethyn-1,2-diyl; prop-1-yn-1,3-diyl; prop-2-yn-1,1-diyl; but-1-yn-1,3-diyl; but-1-yn-1,4-diyl; but-2-yn-1,1-diyl; but-2-yn-1,4-diyl; but-3-yn-1,1-diyl; but-3-yn-1,2-diyl; but-3-yn-2,2-diyl; and buta-1,3-diyn-1,4-diyl. The alkynylene group may be unsubstituted or substituted (e.g., optionally substituted alkynylene) as described for alkynyl groups.

"Heteroaryl," as used herein, refers to a monocyclic, bicyclic, or tricyclic ring of 5 to 14 ring atoms containing one or more ring heteroatoms independently selected from O—, S—, —N= (trivalent nitrogen), and N(H)—, and the remaining ring atoms being carbon atoms, wherein the monocyclic ring is aromatic and wherein at least one of the rings in the bicyclic or tricyclic rings is aromatic (but does not have to be a ring which contains a heteroatom, e.g.; tetrahydroquinolinyl, dihydroisoquinolinyl, dihydrobenzodioxinyl, 2,3-dihydrobenzo[b][1,4]dioxinyl, and the like). In certain embodiments, heteroaryl is a monocylic ring of 5 to 6 rings atoms. Unless stated otherwise, the valency may be located on any atom of any ring of the heteroaryl group, valency rules permitting. In certain embodiments, heteroaryl includes, but is not limited to, triazolyl, tetrazolyl, pyrrolyl, imidazolyl, thienyl, furanyl, pyrazolyl, thiazolyl, oxazolyl, isooxazolyl, oxadiazolyl, thiadiazolyl, indolyl, indolinyl, isoindolinyl, indazolyl, benzimidazolyl, benzoxazolyl, benzofuranyl, benzothienyl, benzopyranyl, benzothiazolyl, pyridyl, pyrazinyl, pyrimidinyl, pyridazinyl, quinolinyl, isoquinolinyl, tetrahydroisoquinolinyl, dihydroisoquinolinyl, pyrrolo[3,2-c]pyridinyl, pyrrolo[1,2-b]pyridazinyl, imidazo[1,2-a]pyridinyl, benzo[d][1,3]dioxolyl, 2,3 dihydrobenzo[b][1,4]dioxinyl, furo[2,3-d]thiazolyl, thieno[2,3-d]oxazolyl, thieno[3,2-b]furanyl, furo[2,3-d]pyrimidinyl, furo[3,2-b]pyridinyl, furo[3,2-c]pyridinyl, 6,7-dihydro-5H-cyclopenta[b]pyridinyl, 7,8 dihydro-6H-cyclopenta[g]quinoxalinyl, dihydrobenzodioxinyl, or 2,3-dihydrobenzo[b][1,4]dioxinyl.

As used herein and unless otherwise specified, a "halogen" is fluorine, chlorine, bromine or iodine.

6.2 Embodiments (a) Compounds

In one aspect, provided herein are photoactive fluorescent compounds. In one embodiment, the photoactive fluorescent compounds are for use in labeling, for example, labeling proteins. In one embodiment, the compounds disclosed herein are useful for visualizing the location and dynamics of protein in living cells.

Figure 1:
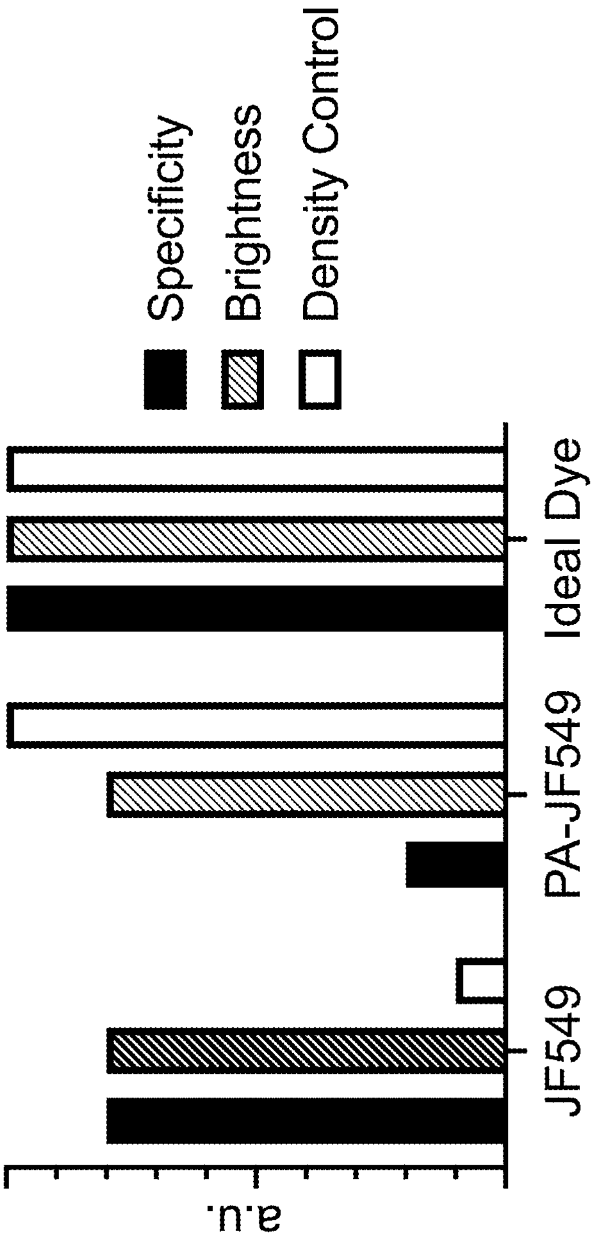

These compounds display unexpectedly improved properties, such as improved photostability, brightness, labeling specificity, and control of density, which are desired properties for photoactive fluorescent compounds. See FIG. 1 which provides a schematic of specificity, brightness and density control for a commercial non-photoactivatable dye, Janelia Fluor® 549 ($JF_{549}$), a commercial photoactivatable dye (PA-$JF_{549}$), and an ideal dye. $JF_{549}$ exhibits high specificity and brightness but poor density control. On the other hand, PA $JF_{549}$ exhibits high brightness and density control but poor specificity. An ideal dye would exhibit high specificity, brightness and density control, which are not predictable properties based on structural features alone. For example, modification of the PA-$JF_{549}$ core structure can alter not only the photophysical properties of the photoconverted dye produced, but can also alter the dye's propensity to photoactivate after exposure to blue light. As noted above, the compounds disclosed herein, which have modified PA-$JF_{549}$ core structures, display unexpectedly improved properties.

In certain embodiments, the compound is of Formula (I):

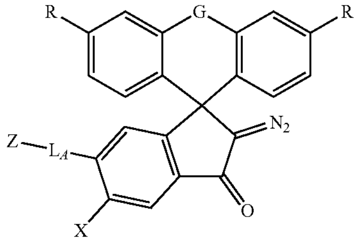

(I)

or a salt, a single stereoisomer, a mixture of stereoisomers or an isotopic form thereof, wherein $L_A$ is a linker, Z comprises a moiety that covalently bonds to a tagged protein, and the other variables are as defined herein.

In certain embodiments, $L_A$ is a linker of Formula (IA):

$$-(L_2)_b-(L^1)^a- \quad \text{(IA)}$$

wherein:

each $L^1$ is independently:

(i) —$C_{1-6}$-alkylene-, —$C_{1-6}$-alkenylene-, or —$C_{1-6}$-alkynylene-;

(ii) a heteroaryl; or (iii) —NHC(O)—, —C(O)NH—, —OC(O)—, —C(O)O—, —N($C_{1-3}$ alkyl)-C(O)—, —C(O)—N($C_{1-3}$ alkyl)-, —$C_{1-6}$-alkylene-NH—, —NH—$C_{1-6}$-alkylene-, —$C_{1-6}$-alkylene-N($C_{1-6}$-alkylene)-, —N($C_{1-6}$-alkylene)-$C_{1-6}$-alkylene-, —$C_{1-6}$-alkylene-O—, —O—$C_{1-6}$-alkylene-, —C(O)—$C_{1-6}$-alkylene-, or —$C_{1-6}$-alkylene-C(O)—;

each $L^2$ is independently —$C_{1-6}$-alkylene-, —$(OCH_2)_p$, —$(CH_2O)_p$—, —$(OCH_2CH_2)_p$—, or —$(CH_2CH_2O)_p$—;

p is an integer of 1 to 3; and a and b are each independently an integer of 1 or 2.

In certain embodiments, $L_A$ is in an orientation such that -$(L^2)_b$- is bonded to Z, as depicted below in Formula (IB):

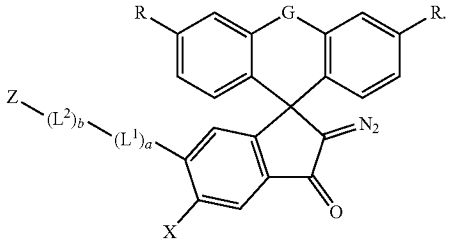

(IB)

In certain embodiments, the compound of Formula (IB) is that wherein:

when R is

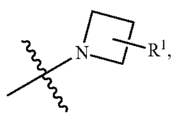

$R^1$ is H and X is H, then Z-$(L^2)_b$-$(L')_a$- is not

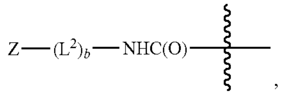

, wherein the wavy line represents a point of attachment to the rest of the compound.

In certain embodiments of the compound of Formula (I) or (IB), G is —O—, —S—, —$SO_2$—, —$C(C_{1-3}$ alkyl$)_2$-, —$N(C_{1-3}$ alkyl)-, —$Si(C_{1-3}$ alkyl$)_2$-, —P(═O)(OH)—, —P(═O)$(C_{1-3}$ alkyl)-, or —P(═O)(Ph)-.

In certain embodiments of the compound of Formula (I) or (IB), R is

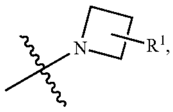

,

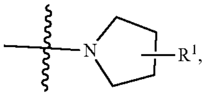

, or

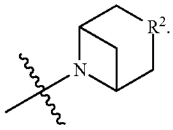

.

In certain embodiments of the compound of Formula (I) or (IB), $R^1$ is —OH, —C(═O)OH, —C(═O)O$(C_{1-3}$ alkyl), —C(═O)$N(C_{1-3}$ alkyl$)_2$, —$N(C_{1-3}$ alkyl$)_2$, —$(CH_2)_n$O$(C_{1-3}$ alkyl),

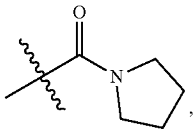

,

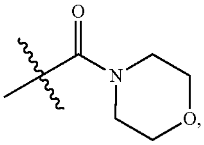

, or

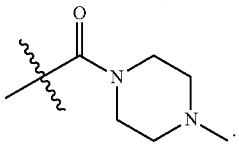

.

In certain embodiments of the compound of Formula (I) or (IB), $R^2$ is —O— or —$N(C_{1-3}$ alkyl)-.

In certain embodiments of the compound of Formula (I) or (IB), X is hydrogen or halogen.

In certain embodiments of the compound of Formula (I) or (IB), X is halogen.

In certain embodiments, the compound of Formula (IB) is that wherein:

R is

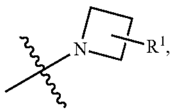

, $R^1$ is H and X is halo.

In certain embodiments of the compound of Formula (I) or (IB), Z is

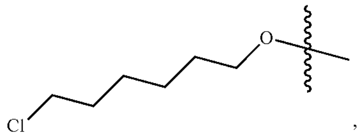

,

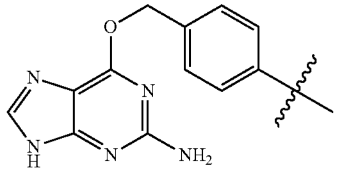

,

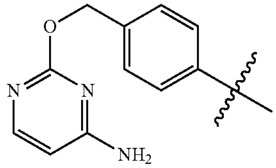

, or

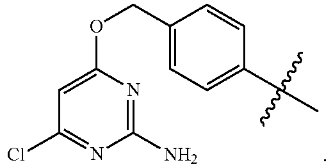

.

In certain embodiments, the compound of Formula (I)

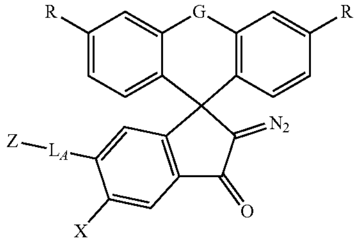

(I)

is that wherein:

G is —O—, —S—, —$SO_2$—, —$C(C_{1-3}$ alkyl$)_2$-, —$N(C_{1-3}$ alkyl)-, —$Si(C_{1-3}$ alkyl$)_2$-, —P(═O)(OH)—, —P(═O)$(C_{1-3}$ alkyl)-, or —P(═O)(Ph)-;

R is

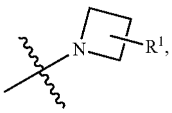

,

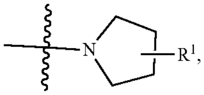

, or

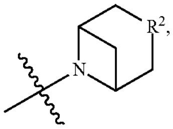

, wherein the wavy line ( ) represents a point of attachment to the rest of the compound;

wherein:

$R^1$ is H, —OH, —C(═O)OH, —C(═O)O$(C_{1-3}$ alkyl), —C(═O)$N(C_{1-3}$ alkyl$)_2$, —$N(C_{1-3}$ alkyl$)_2$, —$(CH_2)_n$O$(C_{1-3}$ alkyl),

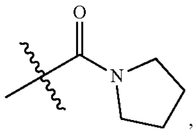,
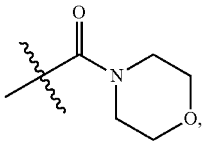, or
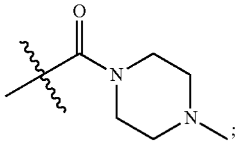;

$R^2$ is —O— or —N($C_{1-3}$ alkyl)-;
X is hydrogen or halogen;
$L_A$ is a linker; and
Z is

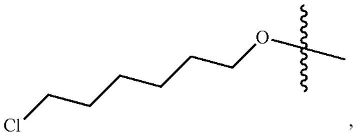,
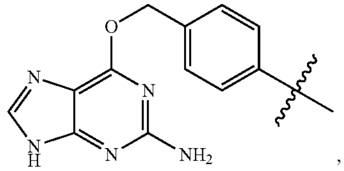,
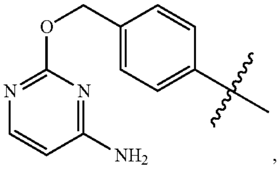, or
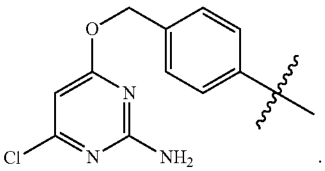.

In certain embodiments, the compound of Formula (I) is that wherein:

when $L_A$ is a linker of Formula (IA), R is

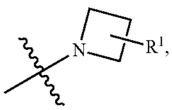, $R^1$ is H and X is H, then Z-$(L^2)_b$-$(L^1)_a$- is not

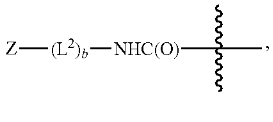, wherein the wavy line ( ) represents a point of attachment to the rest of the compound.

In certain embodiments, the compound of Formula (IB)

(IB)

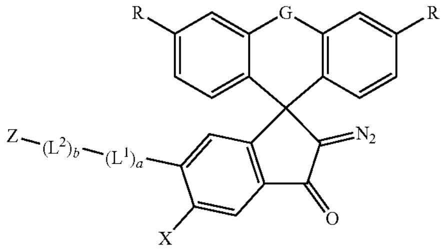

is that wherein:

G is —O—, —S—, —$SO_2$—, —C($C_{1-3}$ alkyl)$_2$-, —N($C_{1-3}$ alkyl)-, —Si($C_{1-3}$ alkyl)$_2$-, —P(═O)(OH)—, —P(═O)($C_{1-3}$ alkyl)-, or —P(═O)(Ph)-;

R is

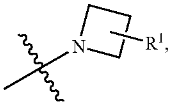,
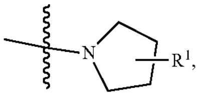, or
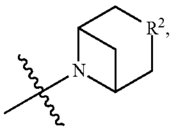, wherein the wavy line ( ) represents a point of attachment to the rest of the compound;

wherein:

$R^1$ is H, —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

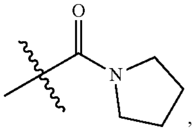,
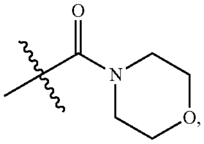, or
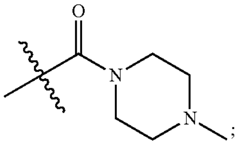;

$R^2$ is —O— or —N($C_{1-3}$ alkyl)-;

X is hydrogen or halogen;

each $L^1$ is independently:

(i) —$C_{1-6}$-alkylene-, —$C_{1-6}$-alkenylene-, or —$C_{1-6}$-alkynylene-;

(ii) a heteroaryl; or (iii) —NHC(O)—, —C(O)NH—, —OC(O)—, —C(O)O—, —N($C_{1-3}$ alkyl)-C(O)—, —C(O)—N($C_{1-3}$ alkyl)-, —$C_{1-6}$-alkylene-NH—, —NH—$C_{1-6}$-alkylene-, —$C_{1-6}$-alkylene-N($C_{1-6}$-alkylene)-, —N($C_{1-6}$-alkylene)-$C_{1-6}$-alkylene-, —$C_{1-6}$-alkylene-O—, —O—$C_{1-6}$-alkylene-, —C(O)—$C_{1-6}$-alkylene-, or —$C_{1-6}$-alkylene-C(O)—;

each $L^2$ is independently —$C_{1-6}$-alkylene-, —$(OCH_2)_p$, —$(CH_2O)_p$—, —$(OCH_2CH_2)_p$—, or —$(CH_2CH_2O)_p$—;

p is an integer of 1 to 3;

a and b are each independently an integer of 1 or 2; and Z is

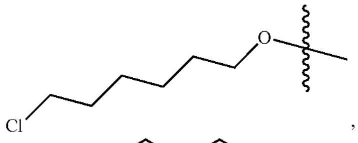

,

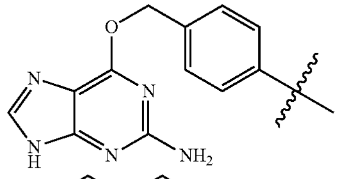

,

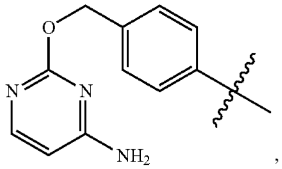

, or

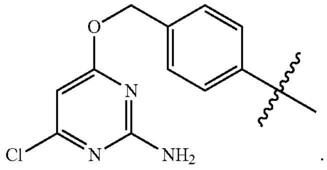

.

In some such embodiments of the compound of Formula (IB), Z is

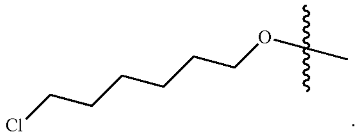 [SMILES: *OCCCCCCCl]

.

In some such embodiments of the compound of Formula (IB), where Z is

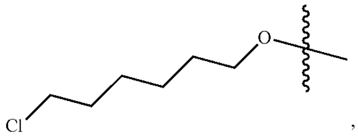 [SMILES: *OCCCCCCCl]

,

X is hydrogen.

In some such embodiments of the compound of Formula (IB), where Z is

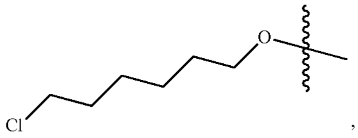 [SMILES: *OCCCCCCCl]

,

X is Fluorine.

In certain embodiments, the compound of Formula (I) is that wherein:

when R is

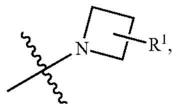

$R^1$ is H and X is H, then Z-$(L^2)_b$-$(L^1)_a$- is not

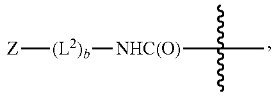

, wherein the wavy line ( ) represents a point of attachment to the rest of the compound.

In certain embodiments, the tagged protein comprises a HaloTag®, SNAP-tag®, or CLIP-tag®.

In certain embodiments, provided herein is a compound of Formula (II):

(II)

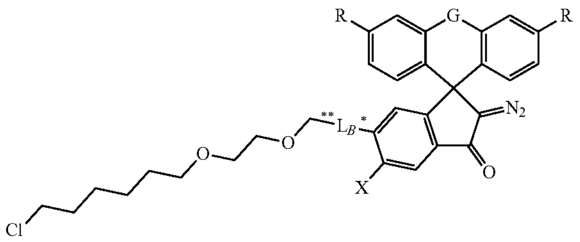

or a salt, a single stereoisomer, a mixture of stereoisomers, or an isotopic form thereof, wherein: the asterixes "**" and "*" denote the orientation of linker $L_B$; and the other variables are as defined herein.

In certain embodiments of the compound of Formula (II), G is —O—, —S—, —$SO_2$—, —C($C_{1-3}$ alkyl)$_2$-, —N($C_{1-3}$ alkyl)-, —Si($C_{1-3}$ alkyl)$_2$-, —P(═O)(OH)—, —P(═O)($C_{1-3}$ alkyl)-, or —P(═O)(Ph)-.

In certain embodiments of the compound of Formula (II), R is

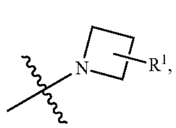

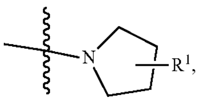

, or

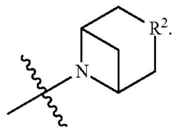

In certain embodiments of the compound of Formula (II), $R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

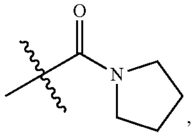, 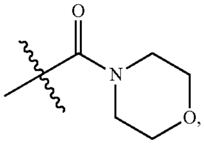, or

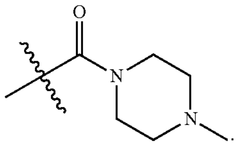.

In certain embodiments of the compound of Formula (II), X is hydrogen or halogen. In some such embodiments, X is hydrogen. In some such embodiments, X is halogen.

In certain embodiments of the compound of Formula (II), $R^2$ is —O— or —N($C_{1-3}$ alkyl)-.

In certain embodiments of the compound of Formula (II), $L_B$ is (i) —$C_{1-6}$-alkylene-, —$C_{1-6}$-alkenylene-, or —$C_{1-6}$-alkynylene-; (ii) a heteroaryl; or (iii) —NHC(O)—, —C(O)NH—, —OC(O)—, —C(O)O—, —N($C_{1-3}$ alkyl)-C(O)—, —C(O)—N($C_{1-3}$ alkyl)-, —$C_{1-6}$-alkylene-NH—, —NH—$C_{1-6}$-alkylene-, —$C_{1-6}$-alkylene-N($C_{1-6}$-alkylene)-, —N($C_{1-6}$-alkylene)-$C_{1-6}$-alkylene-, —$C_{1-6}$-alkylene-O—, —O—$C_{1-6}$-alkylene-, —C(O)—$C_{1-6}$-alkylene-, or —$C_{1-6}$-alkylene-C(O)—.

In certain embodiments of the compound of Formula (II), Z is

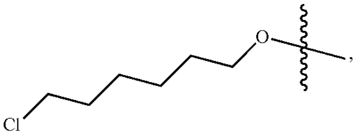 [SMILES: *OCCCCCCCl],

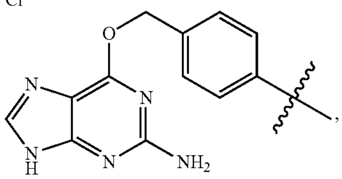,

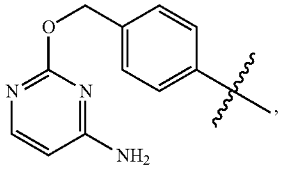, or

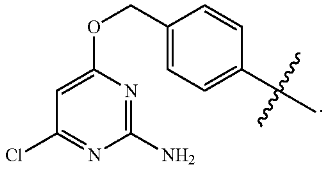.

In some such embodiments of the compound of Formula (II), Z is

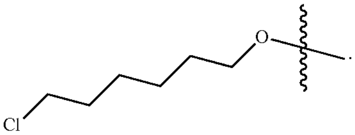 [SMILES: *OCCCCCCCl].

In some such embodiments of the compound of Formula (II), where Z is

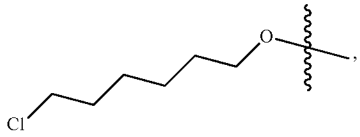 [SMILES: *OCCCCCCCl],

X is hydrogen.

In some such embodiments of the compound of Formula (II), where Z is

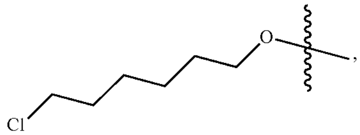,

X is Fluorine.

In certain embodiments, the compound of Formula (II):

(II)

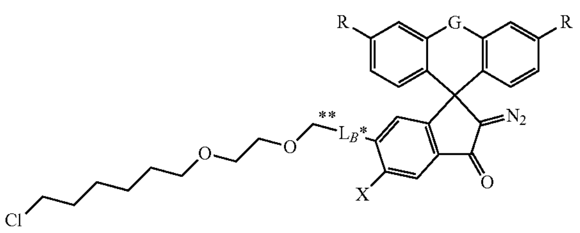

is that wherein.

G is —O—, —S—, —$SO_2$—, —C($C_{1-3}$ alkyl)$_2$-, —N($C_{1-3}$ alkyl)-, —Si($C_{1-3}$ alkyl)$_2$-, —P(═O)(OH)—, —P(═O)($C_{1-3}$ alkyl)-, or —P(═O)(Ph)-;

R is

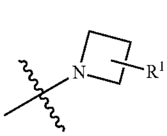 or 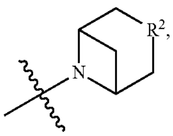, wherein:

$R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

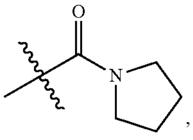, 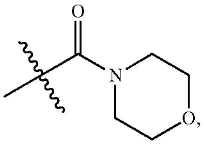, or

-continued

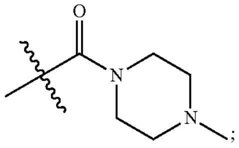

where n is an integer from 1-3; and $R^2$ is —O— or —N($C_{1-3}$ alkyl)-;

X is hydrogen or halogen;

$L_B$ is (i) —$C_{1-6}$-alkylene-, —$C_{1-6}$-alkenylene-, or —$C_{1-6}$-alkynylene-; (ii) a heteroaryl; or (iii) —NHC(O)—, —C(O)NH—, —OC(O)—, —C(O)O—, —N($C_{1-3}$ alkyl)-C(O)—, —C(O)—N($C_{1-3}$ alkyl)-, —$C_{1-6}$-alkylene-NH—, —NH—$C_{1-6}$-alkyl, —$C_{1-6}$-alkylene-N($C_{1-6}$-alkylene)-, —N($C_{1-6}$-alkylene)-$C_{1-6}$-alkylene-, —$C_{1-6}$-alkylene-O—, —O—$C_{1-6}$-alkylene-, —C(O)—$C_{1-6}$-alkylene-, or —$C_{1-6}$-alkylene-C(O)—.

In certain embodiments of the compound of Formula (II), G is —O—, —S—, or —$SO_2$—; R is

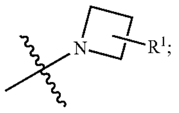

$R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, or —$(CH_2)_n$O($C_{1-3}$ alkyl); $L_B$ is —NHC(O)—, or —C(O)NH—, and X is hydrogen.

In certain embodiments of the compound of Formula (II), G is —O—, or —S—; R is

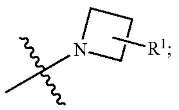

$R^1$ is —C(═O)OH, —C(═O)O($C_{1-3}$ alkyl), —C(═O)N($C_{1-3}$ alkyl)$_2$, or —$(CH_2)_n$O($C_{1-3}$ alkyl); $L_B$ is —NHC(O)—, or —C(O)NH—, and X is hydrogen.

In certain embodiments, provided herein is a compound of Formula (III):

In certain embodiments of the compound of Formula (III), G is —O—, —S—, —N($CH_3$)—, —Si($CH_3$)$_2$—, —C($CH_3$)$_2$—, or —$SO_2$—.

In certain embodiments of the compound of Formula (III), $L_B$ is a linker comprising

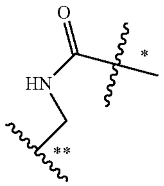
,
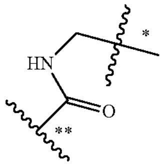
,
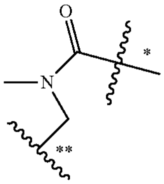
,
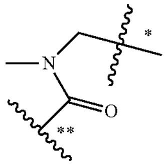
,
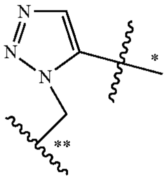
,
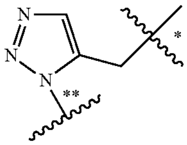
,
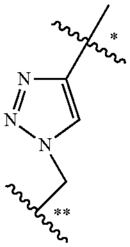
,
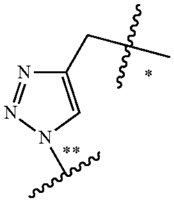
,
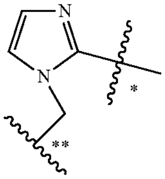
,
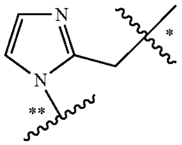
, (III)

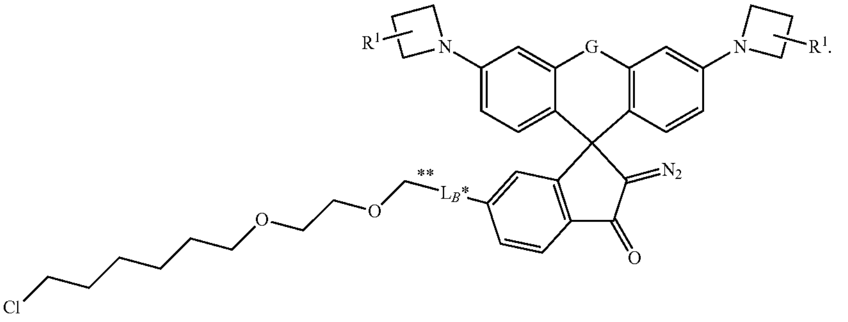

-continued

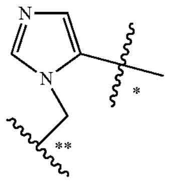, 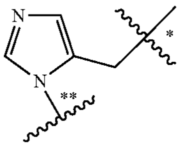,

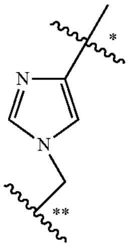, 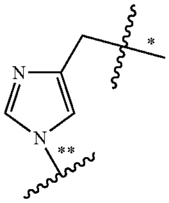, 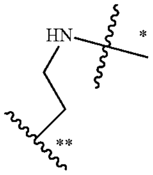,

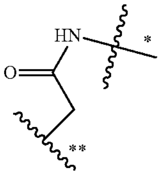, 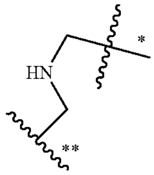, 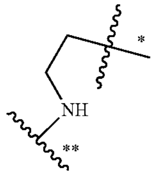,

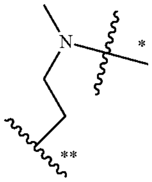, 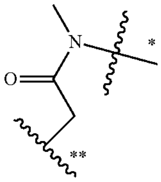, 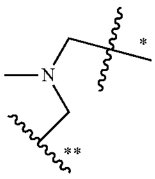,

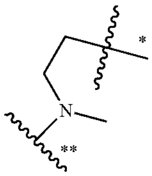, 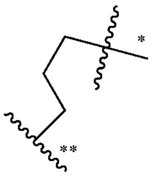, 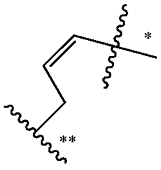,

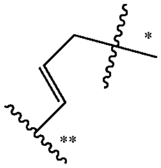, 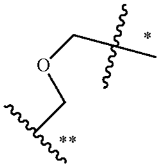,

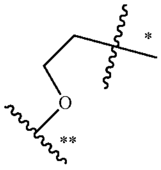, or 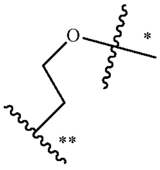, wherein * and ** denote the orientation of the above embodiments in linker $L_B$. It should be noted that those skilled in the art would understand that the placement of the squiggle bond, whether depicted in the middle of the bond, or at the end of the bond, is irrelevant, such that the structures of, for example,

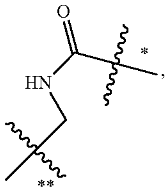, 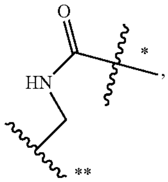, 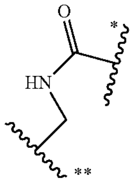, and

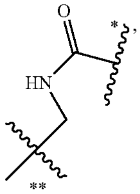, are all equivalent to each other.

In certain embodiments of the compound of Formula (III), $L_B$ comprises a heteroaryl.

In certain embodiments of the compound of Formula (III), the heteroaryl is a triazole or an imidazole.

In certain embodiments of the compound of Formula (III), $R^1$ is

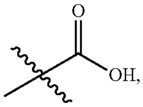, 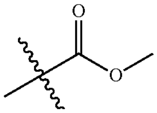, 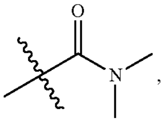,

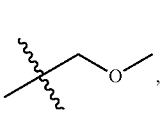, 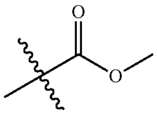, 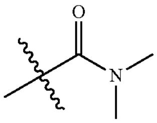,

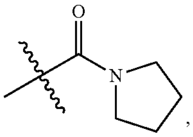, 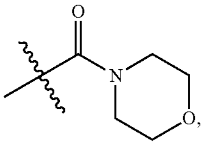, or

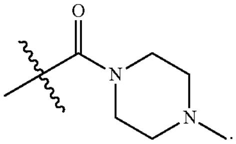.

In certain embodiments of the compound of Formula (III), $R^1$ is H and $L_B$ is

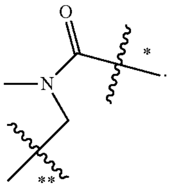.

In certain embodiments, provided herein is a compound of Formula (IV):

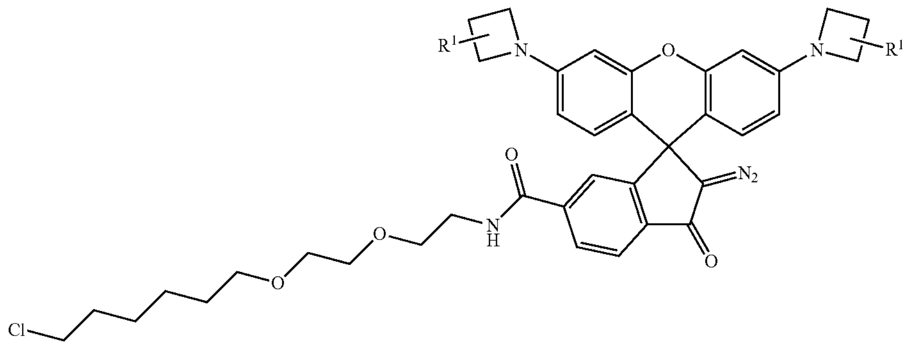

(IV)

wherein:

$R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

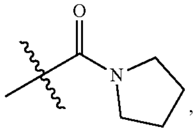,

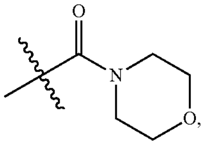 or

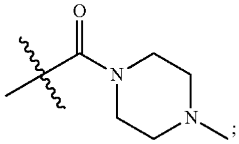

where n is an integer from 1-3.

In certain embodiments, $R^1$ is —$N(CH_3)_2$.

In certain embodiments, $R^1$ is —OH.

In certain embodiments, $R^1$ is

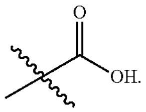 [SMILES: *C(=O)O]

In certain embodiments, $R^1$ is

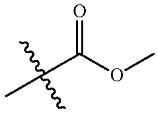.

In certain embodiments, $R^1$ is

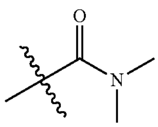.

In certain embodiments, $R^1$ is

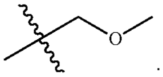 [SMILES: *COC].

In certain embodiments, $R^1$ is

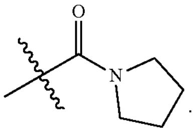 [SMILES: *C(=O)N1CCCC1]

In certain embodiments, $R^1$ is

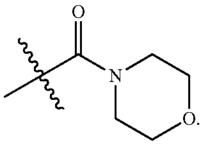 [SMILES: *C(=O)N1CCOCC1]

In certain embodiments, $R^1$ is

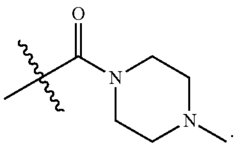 [SMILES: *C(=O)N1CCN(C)CC1]

In certain embodiments, provided herein is a compound of Formula (V):

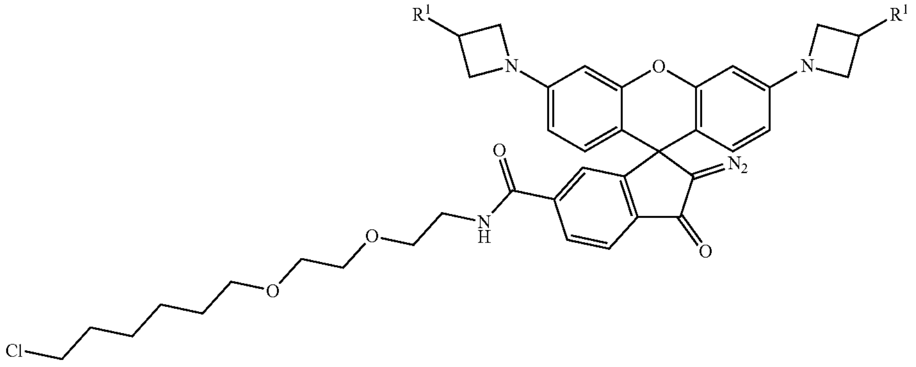

(V)

wherein:

$R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

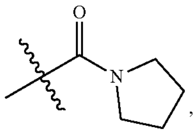
,
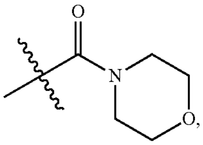
, or

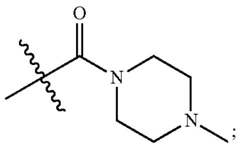
;

where n is an integer from 1-3.

In certain embodiments, provided herein is a compound of Formula (V):

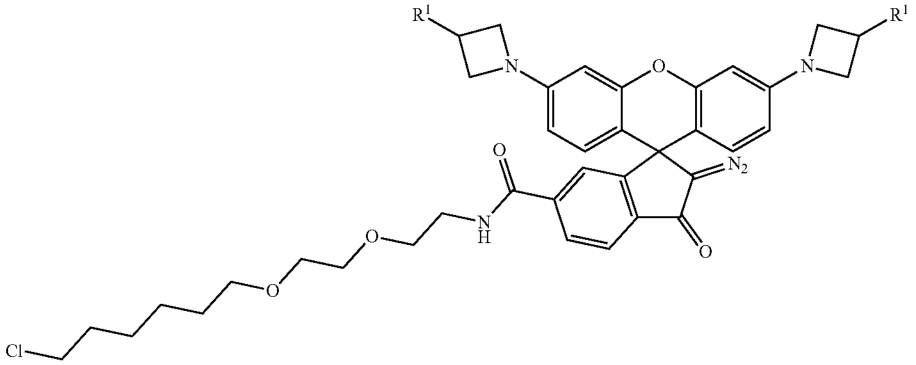

(V)

wherein:

$R^1$ is —OH, —C(═O)OH, —C(═O)O($C_{1-3}$ alkyl), —C(═O)NH($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

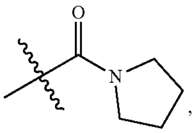
,
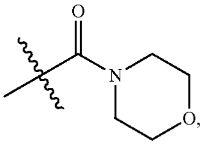
, or

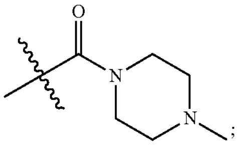
;

where n is an integer from 1-3.

In certain embodiments, provided herein is a compound of Formula (V):

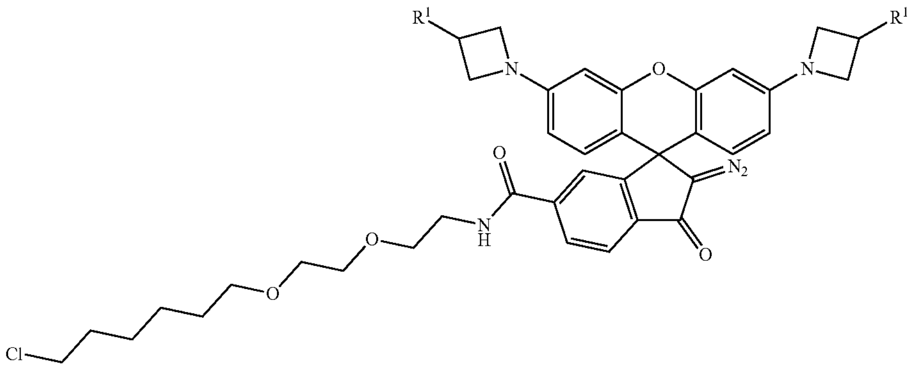

(V)

wherein:

$R^1$ is —OH, —C(═O)OH, —C(═O)O($C_{1-3}$ alkyl), —C(═O)$NH_2$, —C(═O)NH($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),

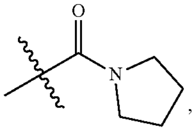
,
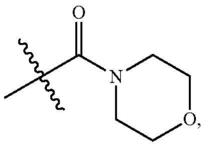
, or

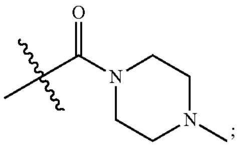
;

where n is an integer from 1-3.

In certain embodiments, $R^1$ is —N$(CH_3)_2$.

In certain embodiments, $R^1$ is —OH.

In certain embodiments, $R^1$ is

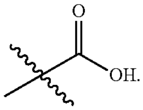 [SMILES: *C(=O)O]

In certain embodiments, $R^1$ is

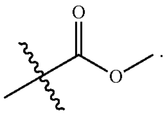 [SMILES: *C(=O)OC]

In certain embodiments, $R^1$ is

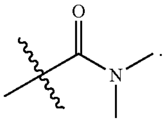 [SMILES: *C(=O)N(C)C]

In certain embodiments, $R^1$ is

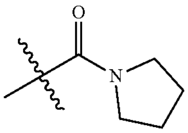

In certain embodiments, $R^1$ is

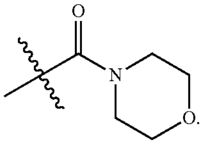 [SMILES: *C(=O)N1CCOCC1]

In certain embodiments, $R^1$ is

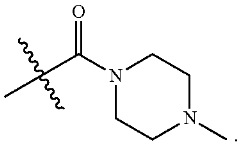 [SMILES: *C(=O)N1CCN(C)CC1]

In certain embodiments, $R^1$ is

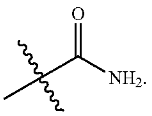 [SMILES: *C(N)=O]

In certain embodiments, provided herein is a compound of Formula (VI):
(VI)
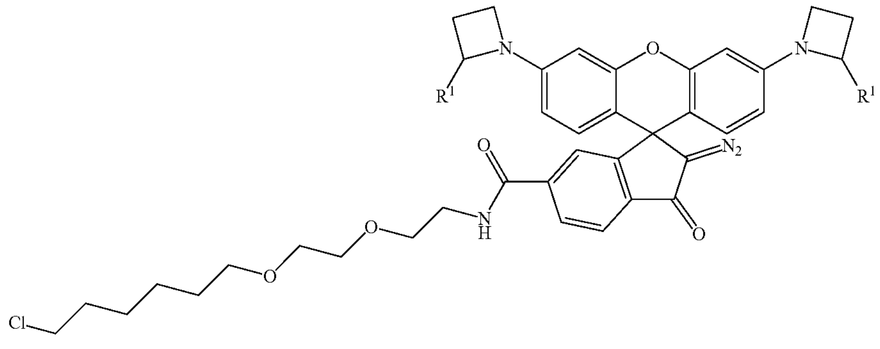
wherein:
$R^1$ is —OH, —C(═O)OH, —C(═O)O($C_{1-3}$ alkyl), —C(═O)N($C_{1-3}$ alkyl)$_2$, —N($C_{1-3}$ alkyl)$_2$, —$(CH_2)_n$O($C_{1-3}$ alkyl),
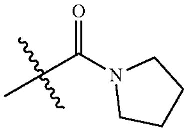,
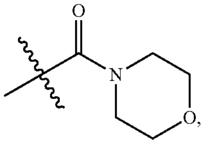, or
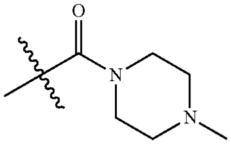;
where n is an integer from 1-3.
In certain embodiments, $R^1$ is
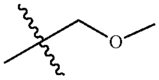.
In certain embodiments, $R^1$ is
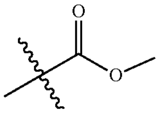.
In certain embodiments, $R^1$ is
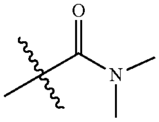.
In certain embodiments, provided herein is a compound of Formula (VIa):
(VIa)
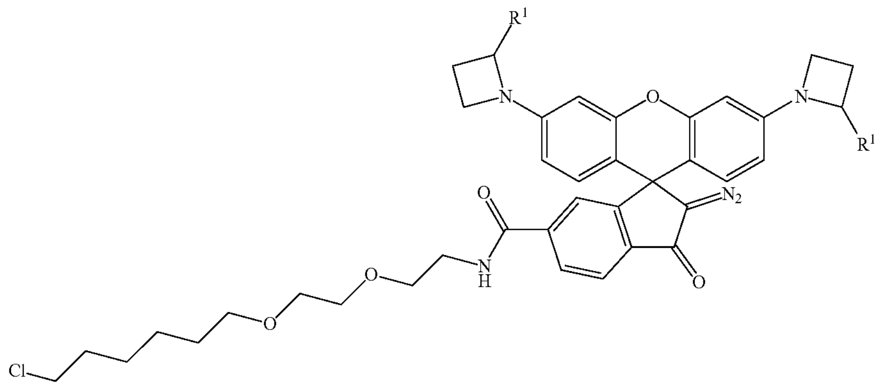

wherein:
$R^1$ is —OH, —C(O)OH, —C(=O)O($C_{1-3}$ alkyl), —C(=O)N($C_{1-3}$ alkyl)$_2$, —N($C_{1-3}$ alkyl)$_2$, —$(CH_2)_n$O($C_{1-3}$ alkyl),
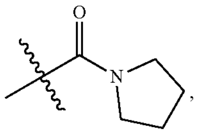
,
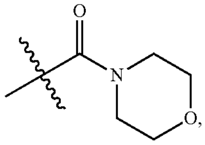
, or
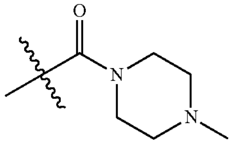
;
where n is an integer from 1-3.
In certain embodiments, $R^1$ is
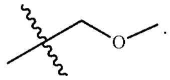 [SMILES: *COC]
.
In certain embodiments, $R^1$ is
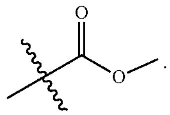 [SMILES: *C(=O)OC]
.
In certain embodiments, $R^1$ is
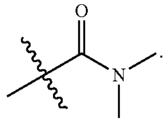 [SMILES: *C(=O)N(C)C]
.
In certain embodiments, the compound is:
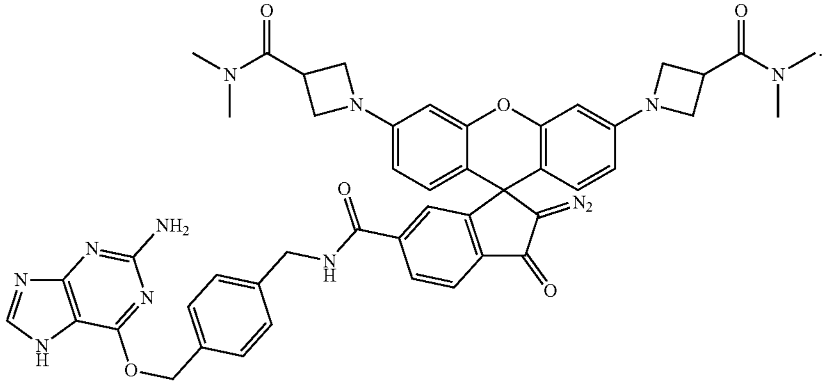
In certain embodiments, the compound is:
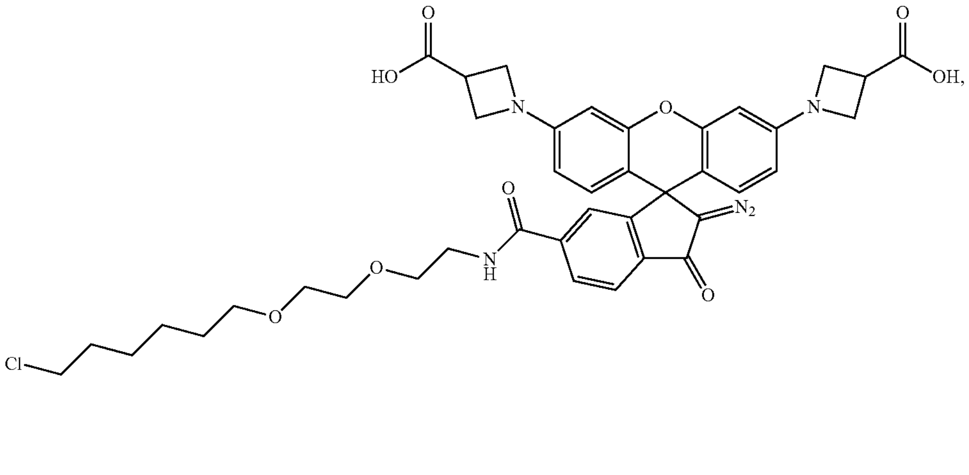
, -continued
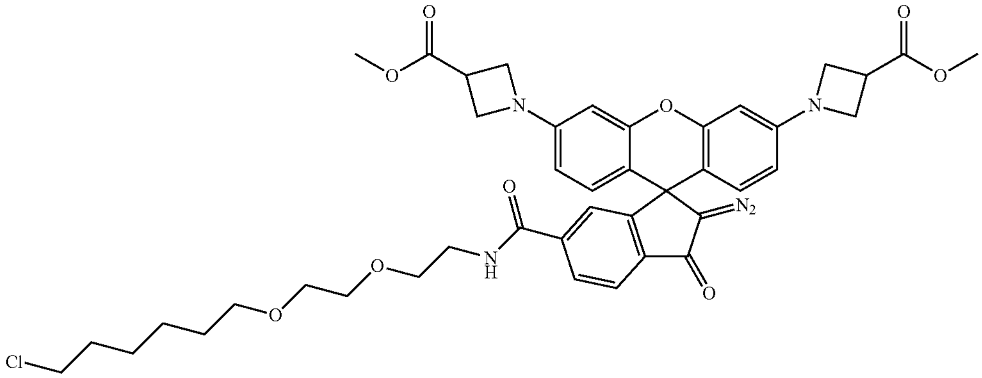
,
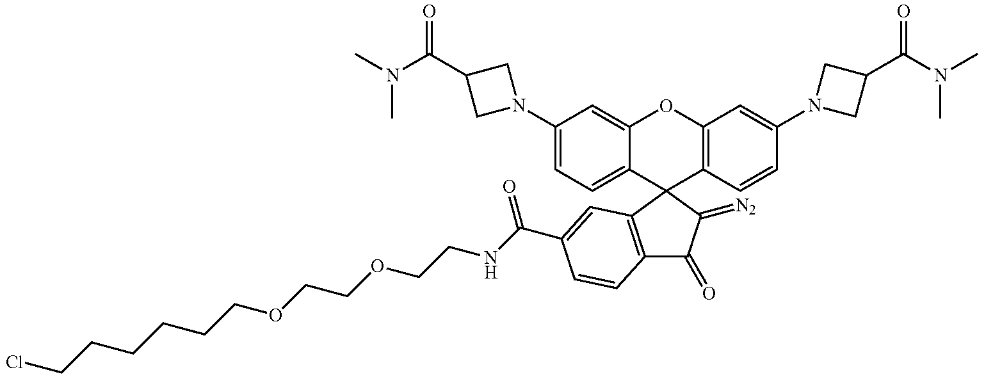
,
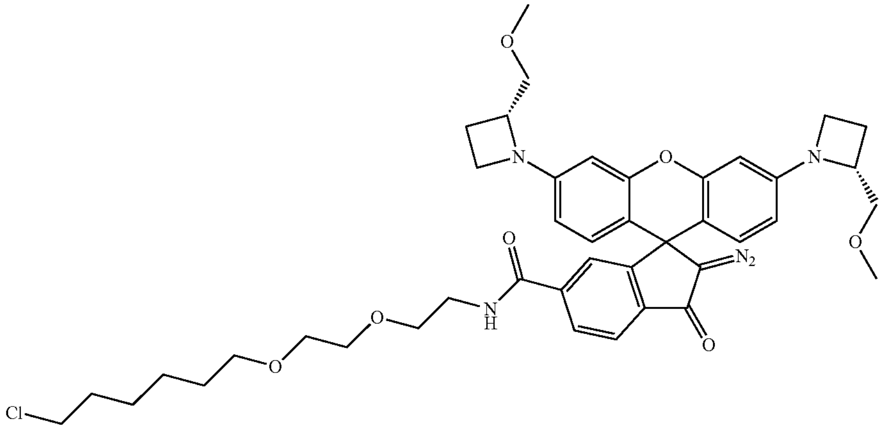
, or
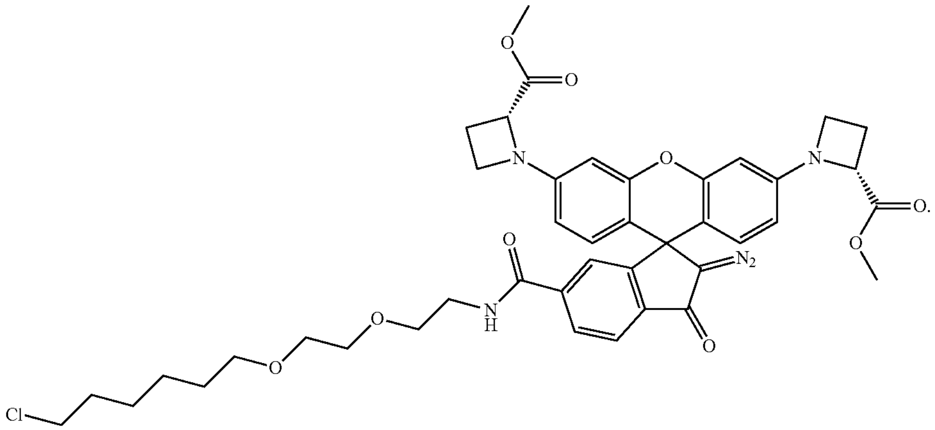

In certain embodiments, the compound is:
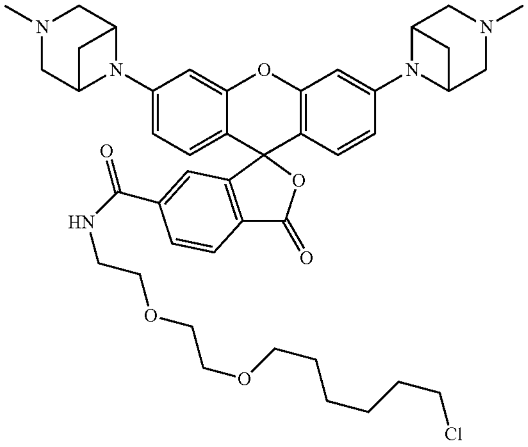
,
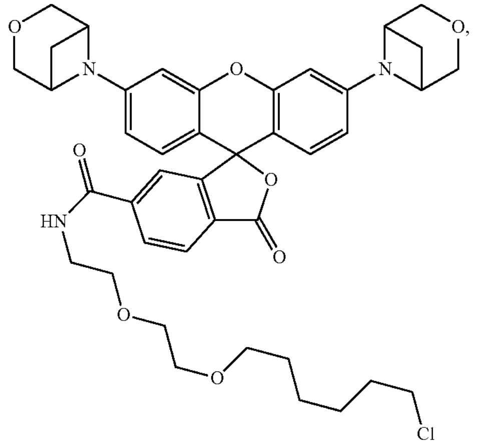
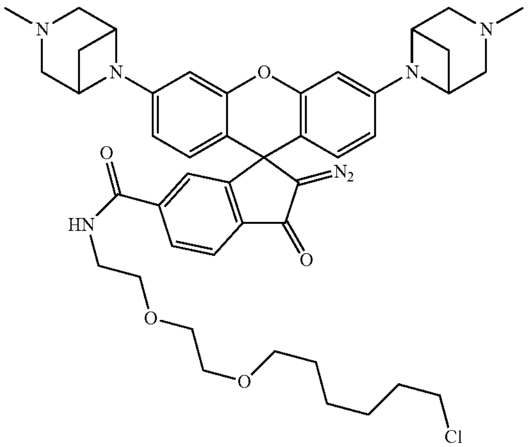
,
-continued
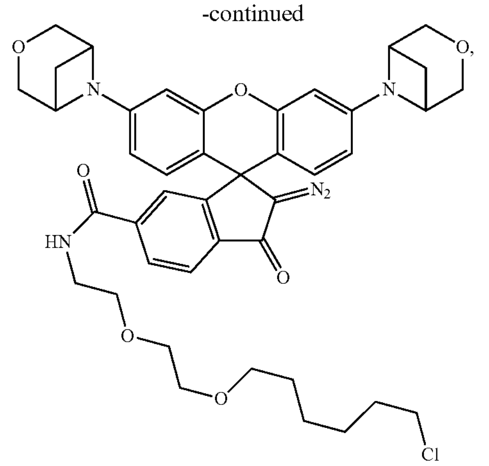
or
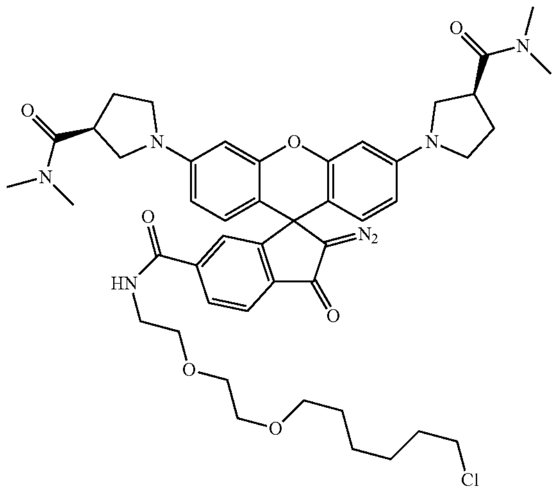
.
In certain embodiments, the compound is:
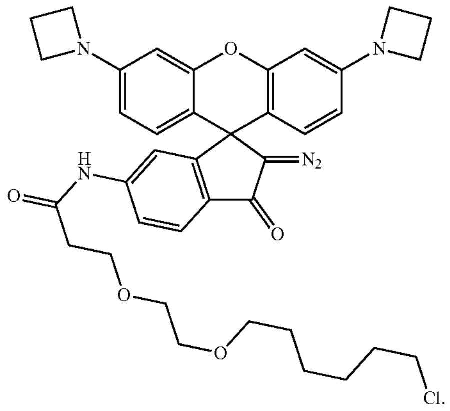

In certain embodiments, the compound of Formula (VIa) is:

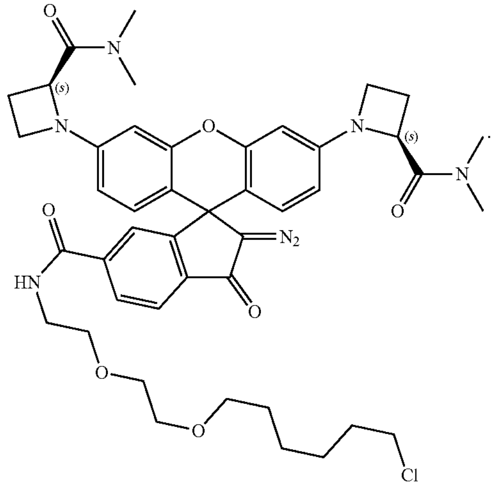

In certain embodiments, the compound of Formula (VIa) is:

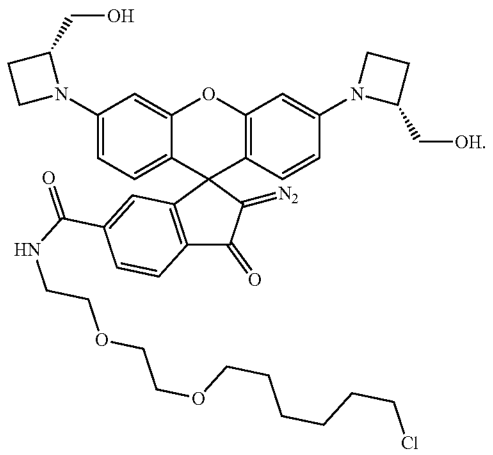

In certain embodiments, provided herein is a compound of Formula (VII):

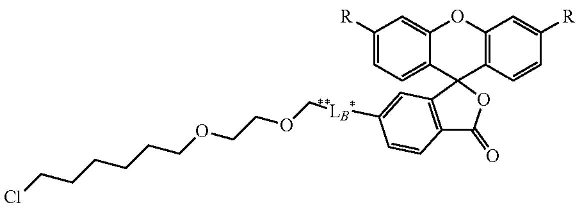

wherein:

R is

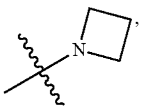, 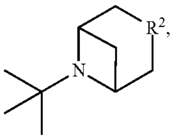, or

-continued

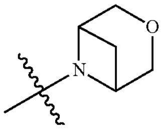

wherein:

$R^2$ is —$CH_3$ and $L_B$ is a linker comprising:

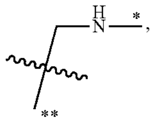, 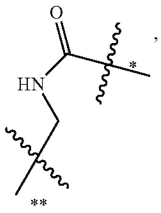,

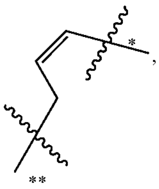, or 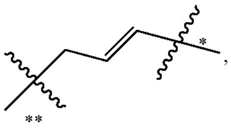, wherein * and ** denote the orientation of the above embodiments in linker $L_B$.

In certain embodiments of the compound of formula (VII), R is not

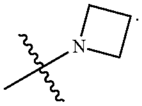.

In certain embodiments of the compound of formula (VII), $L_B$ is not

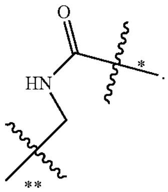 [SMILES: *CNC(*)=O].

In certain embodiments of the compound of formula (VII), when R is

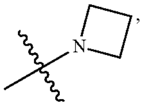, $L_B$ is not

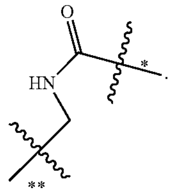 [SMILES: *CNC(*)=O]

In certain embodiments of the compound of formula (VII), when R is

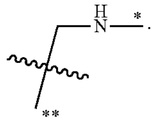

$L_B$ is

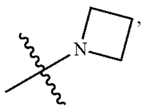

In certain embodiments of the compound of formula (VII), when R is

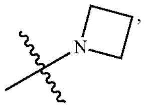

$L_B$ is

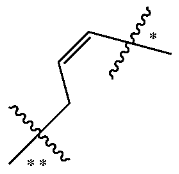

or

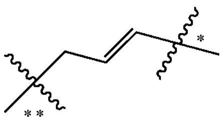

.

In certain embodiments, the compound is dimethyl 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylate).

In certain embodiments, the compound is 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid).

In certain embodiments, the compound is N-(2-(2-((6-chlorohexyl)oxy)ethoxy)ethyl)-2-diazo-3',6'-bis((R)-2-(methoxymethyl)azetidin-1-yl)-3-oxo-2,3-dihydrospiro[indene-1,9'-xanthene]-6-carboxamide.

In certain embodiments, the compound is 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylazetidine-3-carboxamide).

In certain embodiments, the compound is N-(2-(2-((6-chlorohexyl)oxy)ethoxy)ethyl)-3',6'-bis(3-methyl-3,6-diazabicyclo[3.1.1]heptan-6-yl)-3-oxo-3H-spiro[isobenzofuran-1,9'-xanthene]-6-carboxamide.

In certain embodiments, the compound is 3',6'-di(3-oxa-6-azabicyclo[3.1.1]heptan-6-yl)-N-(2-(2-((6-chlorohexyl)oxy)ethoxy)ethyl)-3-oxo-3H-spiro[isobenzofuran-1,9'-xanthene]-6-carboxamide.

In certain embodiments, the compound is 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N-methylazetidine-3-carboxamide).

In certain embodiments, the compound is (2S,2'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylazetidine-2-carboxamide).

In certain embodiments, the compound is N-(2-(2-((6-chlorohexyl)oxy)ethoxy)ethyl)-2-diazo-3',6'-bis((R)-2-(hydroxymethyl)azetidin-1-yl)-3-oxo-2,3-dihydrospiro[indene-1,9'-xanthene]-6-carboxamide.

In certain embodiments, the compound is (3S,3'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylpyrrolidine-3-carboxamide).

In certain embodiments, the compound is 1,1'-(6'-((2-(2-((6-chlorohexyl)oxy)ethoxy)ethyl)carbamoyl)-5,5-dimethyl-3'-oxo-3'H,5H-spiro[dibenzo[b,e]siline-10,1'-isobenzofuran]-3,7-diyl)bis(N,N-dimethylazetidine-3-carboxamide).

In certain embodiments, the compound is 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxamide.

In certain embodiments, the compound is 3',6'-di(azetidin-1-yl)-6-((2-(2-((6-chlorohexyl)oxy)ethoxy)ethyl)amino)-3H-spiro[isobenzofuran-1,9'-xanthen]-3-one.

In certain embodiments, the compound is 3-(2-((6-chlorohexyl)oxy)ethoxy)-N-(3',6'-di(azetidin-1-yl)-2-diazo-3-oxo-2,3-dihydrospiro[indene-1,9'-xanthen]-6-yl)propanamide.

In certain embodiments, the compound is (E)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one.

In certain embodiments, the compound is (Z)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one.

In certain embodiments, the compound is 3',6'-di(azetidin-1-yl)-6-(4-(2-((6-chlorohexyl)oxy)ethoxy)butyl)-2-diazospiro[indene-1,9'-xanthen]-3(2H)-one.

It should be noted that if there is a discrepancy between a depicted structure and a name for that structure, the depicted structure is to be accorded more weight.

The above paragraphs present a number of embodiments of the compounds provided herein. In each instance the embodiment includes both the recited compound(s) as well as a salt, a single stereoisomer, mixture of stereoisomers thereof, or an isotopic form thereof.

(b) Tagged Proteins

In another aspect, provided herein are tagged proteins.

In certain embodiments, the tagged protein is a kinase. In certain embodiments, the tagged protein is a transcription factor. In certain embodiments, the tagged protein is a chromatin modulator. In certain embodiments, the tagged protein is an adapter. In certain embodiments, the tagged protein is a transporter. In certain embodiments, the tagged protein is a pathogenic aggregator.

In certain embodiments, the tagged protein is a histone. In certain embodiments, the histone is a H2B-HaloTag protein.

In certain embodiments, the tag is a HaloTag® (see, e.g., England et al., "HaloTag Technology: A Versatile Platform for Biomedical Applications," *Bioconjugate Chem.* 2015, 26(6), 975-986 (England et al., 2015)). It should be noted that one skilled in the art would know how to make a protein with fused HaloTag®.

In certain embodiments, the HaloTag® is derived from a bacterial enzyme. In certain embodiments, the bacterial enzyme is a haloalkane dehalogenase. In certain embodiments, the HaloTag® is part of a protein fused to a HaloTag®. In certain embodiments, the HaloTag® is expressed using standard recombinant protein expression techniques. In certain embodiments, the HaloTag® protein coding region is inserted near a gene of interest. In certain embodiments, the HaloTag® is self-labeling. In certain embodiments, the HaloTag® specifically binds to a chloroalkane linker. In certain embodiments, the binding of the HaloTag® to the chloroalkane linker is irreversible under physiological conditions. In certain embodiments, the HaloTag® is used as a protein label in enzymatic assays. In certain embodiments, the HaloTag® is used as a protein label in cellular imaging. In certain embodiments, the HaloTag® is used as a protein label for fluorescence microscopy. In certain embodiments, the HaloTag® is used as a protein label in protein arrays. In certain embodiments, the HaloTag® is used as a protein label to determine sub-cellular localization of proteins.

In certain embodiments, the HaloTagged protein is a kinase, a transcription factor, a chromatin modulator, an adapter, a transporter, or a pathogenic aggregator.

In certain embodiments, the tag is a SNAP-tag® (see, e.g., Kolberg et al., "SNAP-Tag Technology: A General Introduction," *Current Pharmaceutical Design,* 2013, 19(30), 5406-5413 (Kolberg et al., 2013)). It should be noted that one skilled in the art would know how to make a SNAP-tagged protein.

In certain embodiments, the SNAP-tag® is engineered from the enzyme alanine glyoxylate transaminase. In certain embodiments, the CLIP-tag® is self-labeling. In certain embodiments, the SNAP-tag® is encoded by the $O^6$-methylguanine-DNA methyltransferase (MGMT) gene. In certain embodiments, the SNAP-tag® reacts covalently with $O^6$ benzylguanine derivatives. In certain embodiments, the SNAP-tag® is used as a protein label in enzymatic assays. In certain embodiments, the SNAP-tag® is used as a protein label in cellular imaging. In certain embodiments, the SNAP-tag® is used as a protein label in fluorescence microscopy. In certain embodiments, the SNAP-tag® is used as a protein label in protein arrays. In certain embodiments, the SNAP-tag® is used as a protein label to determine sub-cellular localization of proteins.

In certain embodiments, the SNAP-tagged protein is a kinase, a transcription factor, a chromatin modulator, an adapter, a transporter, or a pathogenic aggregator.

In certain embodiments, the tag is a CLIP-tag® (see, e.g., Corrêa et al., "Considerations and Protocols for the Synthesis of Custom Protein Labeling Probes," *Methods Mol Biol.* 2015, 1266, 55-79 (Corrêa et al., 2015)). It should be noted that one skilled in the art would know how to make a CLIP-tagged protein.

In certain embodiments, the CLIP-tag® is self-labeling. In certain embodiments, the CLIP-tag® is an orthogonal tag. In certain embodiments, the CLIP-tag® is encoded by the $O^6$-methylguanine-DNA methyltransferase (MGMT) gene. In certain embodiments, the CLIP-tag® reacts covalently with benzylcytosine derivatives. In certain embodiments, the CLIP-tag® is used as a protein label in protein complementation assays. In certain embodiments, the CLIP-tag® is used as a protein label in protein-protein interaction studies. In certain embodiments, the CLIP-tag® is used as a protein label in enzymatic assays. In certain embodiments, the CLIP-tag® is used as a protein label in cellular imaging. In certain embodiments, the CLIP-tag® is used as a protein label in fluorescence microscopy. In certain embodiments, the CLIP-tag® is used as a protein label in protein arrays. In certain embodiments, the CLIP-tag® is used as a protein label to determine sub-cellular localization of proteins.

In certain embodiments, the CLIP-tagged protein is a kinase, a transcription factor, a chromatin modulator, an adapter, a transporter, or a pathogenic aggregator.

(c) Labeled Proteins and Methods

In another aspect, provided herein are methods of making labeled proteins for measuring individual protein movement within the cellular environment.

In certain embodiments, the method comprises contacting a sample comprising a tagged protein with a compound described herein, so as to yield a labeled protein. Without being bound by any mechanism or theory, it will be understood that a tagged protein generally has a genetically modified active site, which can specifically bind the reactive linker of a photoactive fluorescent dye compound, to form a covalent bond between the tag and the linker (see, e.g., Jradi et al., "Chemistry of Photosensitive Fluorophores for Single-Molecule Localization Microscopy," *ACS Chem. Bio.* 2019, 14(6), 1077-1090 (Jradi et al., 2019); see also, e.g., England et al., 2015; Kolberg et al., 2013; and Corrêa et al., 2015). The tagged protein-compound covalent complex is referred to herein as the labeled protein. The covalent bond is formed quickly and essentially irreversibly under physiological conditions.

The labeled protein may then exposed to light, for example, 405 nm light, causing the covalently bonded photoactive dye compound to become fluorescent.

Figure 2:
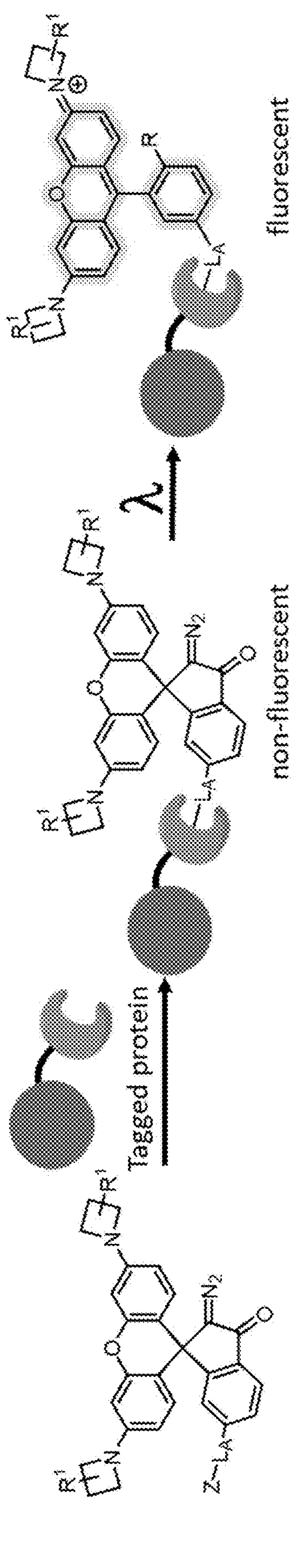
FIG. 2 shows the preparation of photoactivated fluorescently tagged (e.g., labeled) protein.

FIG. 2 shows a schematic for the preparation of a photoactivated labeled protein. As shown in the figure, and as explained above, a tagged protein described herein is contacted with a compound, for example, a photoactive fluorescent dye compound, described herein, resulting in the formation of a covalent bond between the tagged protein and the compound to form the labeled protein. The labeled protein is then treated with light, for example, 405 nm light, causing the covalently attached compound to become fluorescent.

In certain embodiments, a tagged protein described herein is contacted with a compound, for example, a photoactive fluorescent dye compound, described herein, to form the labeled protein. In certain embodiments, the compound is a fluorophore. In certain embodiments, the compound contains a moiety that binds to the tagged protein to form a labeled protein. In certain embodiments, the tagged protein is covalently bonded to the compound, to form the labeled protein. In certain embodiments, the compound bonds covalently to a lysine residue on the tagged protein, forming the labeled protein. In certain embodiments, the compound bonds covalently to a cysteine residue on the tagged protein, forming the labeled protein. In certain embodiments, the compound bonds covalently to an aspartate residue on the tagged protein, forming the labeled protein.

In certain embodiments, the compound portion of the labeled protein fluoresces when exposed to light. Without being bound by any mechanism or theory, it will be understood that the compound portion of the labeled protein may undergo a Wolff rearrangement when exposed to light, commonly followed by decarboxylation of the compound.

In certain embodiments, the labeled protein is illuminated with a 405 nm light source. In certain embodiments, the intensity of the 405 nm light source is about 365 mW. In certain embodiments, the labeled protein is illuminated for about 5 minutes.

In certain embodiments, the labeled protein solution is filtered following incubation. In certain embodiments, the solution is filtered through a desalting column.

In certain embodiments, the labeled protein fluoresces when exposed to light. In certain embodiments, the light is a laser. In certain embodiments, the light wavelength (k) is about 405 nm. In certain embodiments, the intensity of the 405 nm light is less than 1 mW. In certain embodiments, the intensity of the 405 nm light is about 12 mW. In certain embodiments, the intensity of the 405 nm light is between about 0 mW and about 12 mW. In certain embodiments, the intensity of the 405 nm light is greater than 12 mW, for example, about 15, about 20, about 25, about 30, about 35, about 40, about 45, about 50, about 55, about 60, about 70, about 80, about 90, about 100, about 200, about 300, or about 400 mW. In certain embodiments, the laser is pulsed. In certain embodiments, the laser intensity is increased over time during pulsation. In certain embodiments, 561 nm (k) light is used to stimulate the fluorophore of the labeled protein. In certain embodiments, the light wavelength (k) is about 561 nm. In certain embodiments, the intensity of the 561 nm light is about 500 mW. In certain embodiments, the sample comprises one or more live cells, and the protein is labeled in the one or more live cells. In certain embodiments, the protein is labeled in a subcellular compartment of the one or more live cells. In certain embodiments, the protein is labeled in the nucleus of the one or more live cells. In certain embodiments, the protein is labeled in the cytoplasm of the one or more live cells. In certain embodiments, the protein is labeled in the plasma membrane of the one or more live cells. In certain embodiments, the protein is labeled in the mitochondria of the one or more live cells. In certain embodiments, the protein is labeled in the outer membrane of the mitochondria of the one or more live cells. In certain embodiments, the protein is labeled in the inner membrane of the mitochondria of the one or more live cells. In certain embodiments, the protein is labeled in the mitochondrial matrix of the one or more live cells. In certain embodiments, the protein is labeled in the Golgi body of the one or more live cells. In certain embodiments, the protein is labeled in the lysosome of the one or more live cells. In certain embodiments, the protein is labeled in the endosomes of the one or more live cells. In certain embodiments, the protein is labeled in the endoplasmic reticulum of the one or more live cells. In certain embodiments, the protein is labeled in the membrane of the endoplasmic reticulum of the one or more live cells. In certain embodiments, the protein is labeled in the rough endoplasmic reticulum of the one or more live cells.

In certain embodiments, individual protein movement within the cellular environment of the one or more cells is measured. In certain embodiments, individual protein movement within a subcellular compartment of the one or more cells is measured. In certain embodiments, individual protein movement within the nucleus of the one or more cells is measured. In certain embodiments, individual protein movement within the cytoplasm of the one or more live cells is measured. In certain embodiments, individual protein movement within the plasma membrane of the one or more live cells is measured. In certain embodiments, individual protein movement within the mitochondria of the one or more live cells is measured. In certain embodiments, individual protein movement within the outer membrane of the mitochondria of the one or more live cells is measured. In certain embodiments, individual protein movement within the inner membrane of the mitochondria of the one or more live cells is measured. In certain embodiments, individual protein movement within the mitochondrial matrix of the one or more live cells is measured. In certain embodiments, individual protein movement within the Golgi body of the one or more live cells is measured. In certain embodiments, individual protein movement within the lysosome of the one or more live cells is measured. In certain embodiments, individual protein movement within the endosomes of the one or more live cells is measured. In certain embodiments, individual protein movement within the endoplasmic reticulum of the one or more live cells is measured. In certain embodiments, individual protein movement within the membrane of the endoplasmic reticulum of the one or more live cells is measured. In certain embodiments, individual protein movement within the rough endoplasmic reticulum of the one or more live cells is measured. In certain embodiments, the measurements are in real time.

In certain embodiments, the one or more live cells are prepared for imaging, for example, by incubating at about 37° C. In certain embodiments, the one or more live cells are incubated, for example, in the presence of about 5% $CO_2$. In certain embodiments, the one or more live cells are incubated overnight, or for about 8-10 hours. In certain embodiments, the one or more live cells are prepared for imaging by incubating with a compound, for example, a photoactive fluorescent dye compound, described herein, at a concentration of about 1 nM. In certain embodiments, the one or more live cells are prepared for imaging by incubating with a compound, for example, a photoactive fluorescent dye compound, described herein, at a concentration of about 200 nM. In certain embodiments, the one or more live cells are prepared for imaging by incubating with a compound, for example, a photoactive fluorescent dye compound, described herein, at a concentration of between about 1 and about 200 nM. In certain embodiments, the one or more live cells are incubated with a compound, for example, a photoactive fluorescent dye compound, described herein, for about 45 minutes.

In certain embodiments, protein movement within the cellular environment is monitored via confocal microscopy. In certain embodiments, protein movement within the cellular environment is monitored via localization microscopy. In certain embodiments, protein movement within the cellular environment is monitored via super resolution microscopy. In certain embodiments, protein movement within the cellular environment is monitored via single-molecular localization microscopy ("SMLM"). In certain embodiments, protein movement within the cellular environment is monitored via photoactivation localization microscopy ("PALM"). In certain embodiments, protein movement within the cellular environment is monitored via stochastic optical reconstruction microscopy ("STORM").

In certain embodiments, the protein movement within the cellular environment is analyzed via a maximum likelihood estimator model to detect single-molecule fluorescence.

In certain embodiments, signal-to-noise ratio ("SNR") is used as a proxy for single-molecule brightness. In certain embodiments, SNR is analyzed via a log likelihood ratio test. In certain embodiments, the compound, for example, a photoactive fluorescent dye compound, described herein, demonstrates similar SNR to a commercially available photoactivatable fluorescent dye. In certain embodiments, the compound demonstrates similar SNR to a commercially available non-photoactivatable fluorescent dye.

In certain embodiments, labeling specificity is determined using microscopy, for example, confocal microscopy, localization microscopy, super resolution microscopy, SMLM, PALM, or STORM. In certain embodiments, labeling specificity is calculated by comparing the number of spots detected via microscopy, for example, localization microscopy, super resolution microscopy, SMLM, PALM, or STORM with a control sample. In certain embodiments, labeling specificity of the compounds described herein is higher than that of a commercially available photoactivatable fluorescent dye.

7. METHOD OF MAKING COMPOUNDS

The compounds of Formulas (I), (IB), (II), (III), (IV), (V), (VI), and (VIa) can be made using conventional organic syntheses and commercially available starting materials. By way of example and not limitation, compounds of Formulas (I), (IB), (II), (III), (IV), (V), (VI), and (VIa) can be prepared as outlined in Scheme 1 and Scheme 1a, shown below, as well as in the examples set forth herein. It should be noted that one skilled in the art would know how to modify the procedures set forth in the illustrative schemes and to arrive at the desired products.

Scheme 1

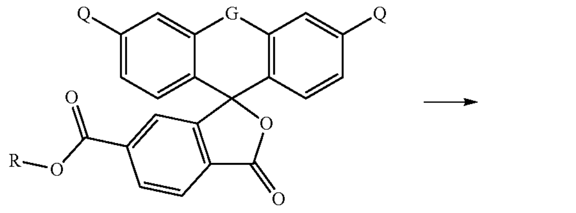

(C)

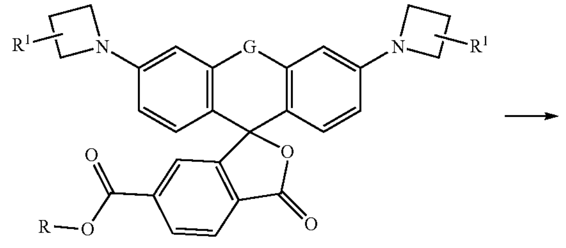

(D)

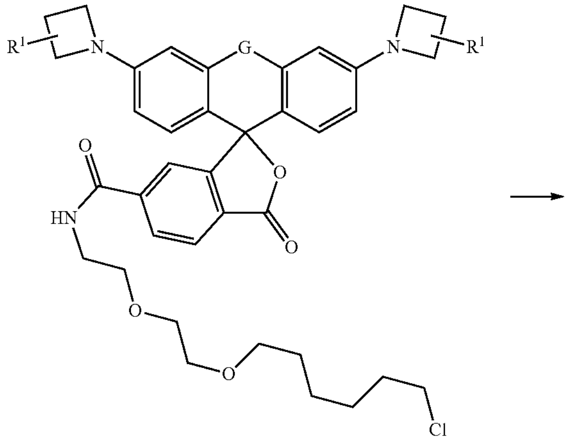

(E)

-continued

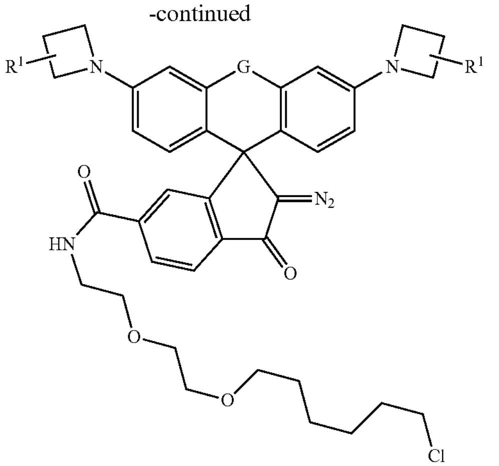

(IV)

As shown in Scheme 1, compounds of Formulas (I), (IB), (II), (III), (IV), (V), (VI), and (VIa) wherein R, G, and $R^1$ are as defined herein, can be prepared starting from an appropriately derivatized intermediate, wherein Q indicates a group capable of undergoing cross-coupling reaction, such as bromine or a triflate derivative, when treated with a suitable catalyst. Intermediate (C) may be prepared as described herein, for example, by converting 3',6'-dihydroxy-3-oxo-3H-spiro[isobenzofuran-1,9'-xanthene]-6-carboxylic acid into its corresponding triflate derivative by conventional organic syntheses methods. Intermediate (C) may also be prepared according to Grimm, et al., "A general method to improve fluorophores for live-cell and single-molecule microscopy," *Nat. Methods* 2015, 12, 244-250 (Grimm et al., 2015); Woodroofe et al., "Synthesis of isomerically pure carboxylate- and sulfonate-substituted xanthene fluorophores," *Tetrahedron* 2005, 61(12), 3097-3105 (Woodroofe et al., 2005); and Grimm et al., "Bright photoactivatable fluorophores for single-molecule imaging," *Nat. Methods* 2016, 13, 985-988 (Grimm et al., 2016). Alternatively, intermediate (C) can be prepared starting from 1,2,4-benzenetricarboxylic acid treated with 3-bromophenol under appropriate conditions. For example, in the preparation of compounds of Formula (IV), treatment of appropriately substituted intermediate (C), wherein G is O, with properly substituted azetidine and a palladium catalyst, such as $Pd_2(dba)_3$ in the presence of a ligand and a base, such as cesium carbonate, in a solvent, such as dioxane, and heating at temperatures ranging from about 25 to about 100° C., provided intermediate (D). Intermediate D is then treated with an acid, such as TFA, or, alternatively, with a base, such as Lithium hydroxideor trimethyltin hydroxide, at temperatures ranging from about 0 to about 25° C. and then coupled with an appropriate linker moiety under basic conditions to afford intermediate (E). Treatment of intermediate (E) with oxalyl chloride in a suitable solvent, such as dichloromethane, at a temperature from about 0 to about 25° C. and subsequent treatment with freshly prepared diazomethane in $Et_2O$ (see, e.g., F. Arndt, "Diazomethane," *Org. Synth.* 1935, 15, 3) at a temperature of about 0° C. afforded compounds of Formula (IV).

Alternatively, treatment of intermediate (E) with 1-Chloro-N,N,2-trimethylprop-1-en-1-amine in a suitable solvent at room temperature in a aprotic solvent in the presence of 4 Å molecular sieves, followed by treatment with trimethylsilyl diazomethane afforded compounds of formula (IV), and such synthetic method may be used in order to optimize the synthesis of particular compounds and is necessary for the synthesis of other compounds. Examples of the use of such synthetic method are set forth in the Example section.

Scheme 1a

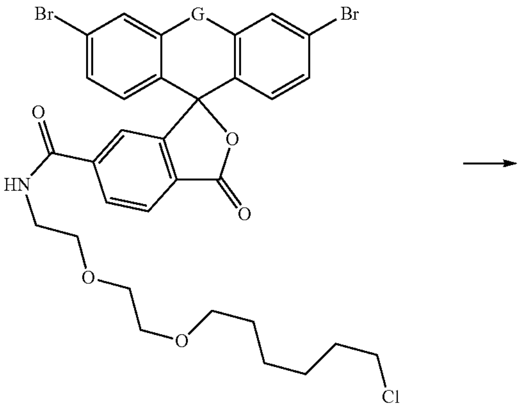

(D')

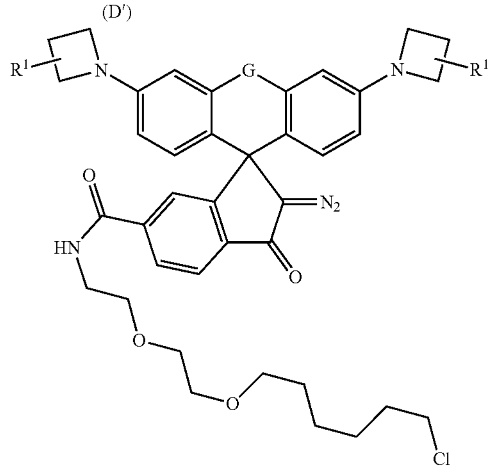

(IV) or (V)

As shown in Scheme 1a, compounds of Formulas (IV) and (V) wherein $R^1$ is as defined herein, can be prepared starting from intermediate (D') via a cross-coupling reaction, with properly substituted azetidine and a palladium catalyst, such as $Pd_2(dba)_3$ in the presence of a ligand and a base, such as cesium carbonate, in a solvent, such as dioxane, and heating at temperatures ranging from about 25 to about 100° C. Intermediate D' can be prepared from Intermediate B1 as described herein in the presence of a peptide coupling reagent such as T3P (Propanephosphonic acid anhydride) in a solvent.

8. METHOD OF MAKING LABELED PROTEINS

By way of example and not limitation, the labeled proteins described herein can be prepared as outlined in Scheme 2, shown below, as well as in the examples set forth herein. It should be noted that one skilled in the art would know how to modify the procedures set forth in the illustrative schemes and to arrive at the desired products.

Scheme 2

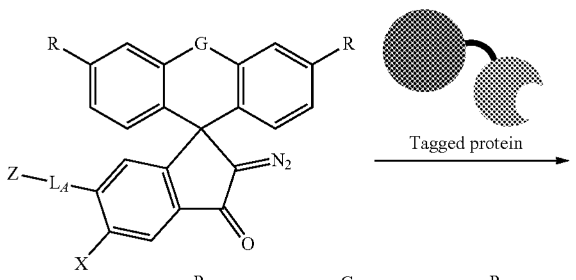

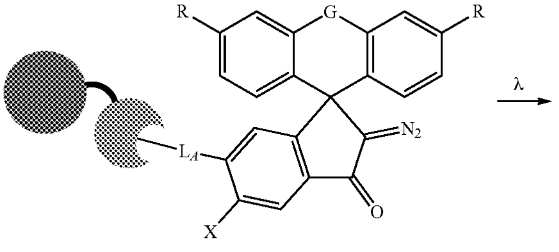

non-fluorescent

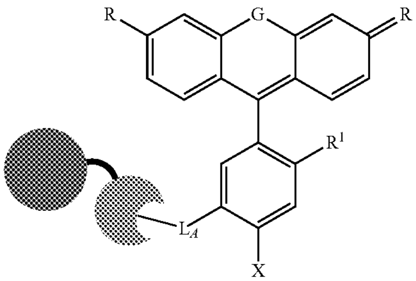

fluorescent

As shown in Scheme 2, compounds of Formulas (I), (IB), (II), (III), (IV), (V), (VI), and (VIa), wherein R, G, X, $L_A$ and Z are as defined herein, can be prepared by contacting a tagged protein described herein with a compound, for example, a photoactive fluorescent dye compound, described herein, resulting in the formation of a covalent bond between the tagged protein and the compound to form the non-fluorescent labeled protein. The non-fluorescent labeled protein is then treated with light (e.g., 405 nm light) causing the compound, and thus, the labeled protein, to become fluorescent. See also FIG. 2.

9. EXAMPLES

The following Examples are presented by way of illustration, not limitation. One skilled in the art can modify the procedures set forth in the illustrative examples to arrive at the desired products.

Abbreviations Used

| Abbreviation: | Meaning: |
|---|---|
| ACN | Acetonitrile |
| $CH_2Cl_2$ | Dichloromethane |
| $Cs_2CO_3$ | Cesium carbonate |
| $CDCl_3$ | Deuterated Chloroform |
| $CHCl_3$ | Chloroform |
| DEA | Diethylamine |

-continued

| Abbreviation: | Meaning: |
|---|---|
| DMAP | 4-Dimethylaminopyridine |
| DMF | Dimethylformamide |
| DMSO | Dimethylsulfoxide |
| DTT | Dithiothreitol |
| EDTA | Ethylenediaminetetraacetic acid |
| EtOAc | Ethyl acetate |
| $Et_2O$ | Diethylether |
| HCl | Hydrochloric acid |
| HPLC | High-Performance Liquid Chromatography |
| HEPES | 2-[4-(2-hydroxyethyl)piperazin-1-yl]ethanesulfonic acid |
| IPA | Isopropyl alcohol |
| KCl | Potassium chloride |
| LiOH | Lithium hydroxide |
| MeOH | Methanol |
| PBS | Phosphate-buffered saline |
| $Pd_2(dba)_3$ | Tris(dibenzylideneacetone)dipalladium(0) |
| RuPhos Pd G4 | (2-Dicyclohexylphosphino-2',6'-diisopropoxy-1,1'-biphenyl)[2-(2'-amino-1,1'-biphenyl)]palladium(II) methanesulfonate |
| SFC | Supercritical Fluid Chromatography |
| THF | Tetrahydrofuran |
| TFA | Trifluoroacetic acid |
| XPhos | 2-Dicyclohexylphosphino-2',4',6'-triisopropyl-1,1'-biphenyl |
| XPhos-Pd-G4 | 2-Dicyclohexylphosphino-2',4',6'-triisopropyl-1,1'-biphenyl-Palladium Generation 4 |
| T3P | Propanephosphonic acid anhydride |
| TBTU | 2-(1H-Benzotriazole-1-yl)-1,1,3,3-tetramethylaminium tetrafluoroborate |
| HOBT | 1-Hydroxybenzotriazole hydrate |

Intermediates

Intermediate A

Synthesis of tert-butyl 3-oxo-3',6'-bis(((trifluoromethyl)sulfonyl)oxy)-3H-spiro[isobenzofuran-1,9'-xanthene]-6-carboxylate Intermediate A

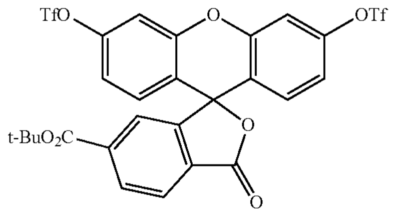

Step 1: Preparation of 3',6'-diacetoxy-3-oxo-3H-spiro[isobenzofuran-1,9'-xanthene]-6-carboxylic acid Compound A1

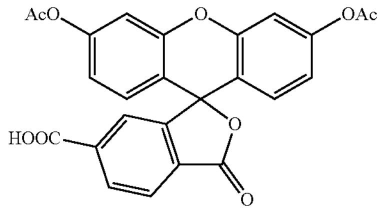

A solution of 3',6'-dihydroxy-3-oxo-3H-spiro[isobenzofuran-1,9'-xanthene]-6-carboxylic acid (5.0 g, 13.3 mmol) in acetic anhydride (25 mL) was stirred under reflux at 110° C. for 3 h. The mixture was diluted with water (50 mL) and extracted with ethyl acetate (2×50 mL). The organic layer was concentrated under reduced pressure and the residue was purified by silica gel column chromatography (eluent: 50-55% EtOAc in petroleum ether) to afford 3',6'-diacetoxy-3-oxo-3H-spiro[isobenzofuran-1,9'-xanthene]-6-carboxylic acid (3.7 g, 61% yield) of as a solid. $^1$H NMR: (400 MHz, CDCl3): δ 8.35 (d, 1H), 1.13 (d, 1H), 7.87 (s, 1H), 7.12 (s, 2H), 6.78-6.84 (dd, 4H), 2.31 (s, 6H) ppm. m/z=461.5 [M+H]+.

Step 2: Preparation of 6-(tert-butoxycarbonyl)-3-oxo-3H-spiro[isobenzofuran-1,9'-xanthene]-3',6'-diyl diacetate Compound A2

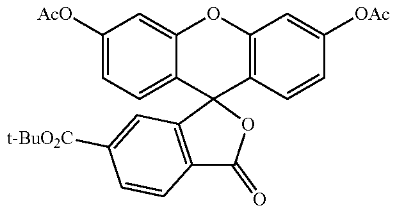

To a stirred solution of 3',6'-diacetoxy-3-oxo-3H-spiro[isobenzofuran-1,9'-xanthene]-6-carboxylic acid (3.7 g, 8.0 mmol) in toluene (14 mL) was added 1,1-di-tert-butoxy-N,N-dimethylmethanamine (9.8 g, 48.2 mmol) and the mixture was stirred under reflux for 1 h. The mixture was cooled to room temperature and concentrated under reduced pressure to afford 6-(tert-butoxycarbonyl)-3-oxo-3H-spiro[isobenzofuran-1,9'-xanthene]-3',6'-diyl diacetate (3.7 g, crude), as brownish solid, which was used in next step without further purification. m/z=517.5 [M+H]+.

Step 3: Preparation of tert-butyl 3',6'-dihydroxy-3-oxo-3H-spiro[isobenzofuran-1,9'-xanthene]-6-carboxylate Compound A3

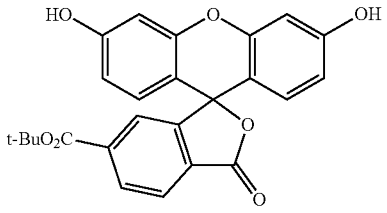

To a stirred solution of 6-(tert-butoxycarbonyl)-3-oxo-3H-spiro[isobenzofuran-1,9'-xanthene]-3',6'-diyl diacetate (3.7 g, 7.2 mmol) in THE (17 mL) and methanol (17 mL) was added sodium hydroxide (1 M, 10.2 mL, 10.2 mmol). The mixture was stirred for 12 h at room temperature and then concentrated under reduced pressure. The residue was diluted with water (50 mL) and acidified with aqueous citric acid (sat.). The aqueous layer was extracted with ethyl acetate (2×50 mL) and the combined organic layers were concentrated under reduced pressure. The residue was purified by silica gel column chromatography (eluent: 35% EtOAc in petroleum ether) to afford tert-butyl 3',6'-dihydroxy-3-oxo-3H-spiro[isobenzofuran-1,9'-xanthene]-6-carboxylate (2.8 g) as a solid. m/z=433.6 [M+H]+.

Step 4: Preparation of tert-butyl 3-oxo-3',6'-bis(((trifluoromethyl)sulfonyl)oxy)-3H-spiro[isobenzofuran-1,9'-xanthene]-6-carboxylate Compound A4

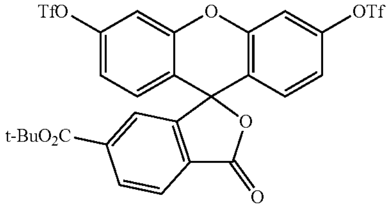

To a solution of tert-butyl 3',6'-dihydroxy-3-oxo-3H-spiro[isobenzofuran-1,9'-xanthene]-6-carboxylate (2.8 g, 6.5 mmol), in DMF (28 mL) at 0° C. was added N,N-diisopropylethylamine (4.5 mL, 25.9 mmol) followed by N-phenyl-O-((trifluoromethyl)sulfonyl)-N-(((trifluoromethyl)sulfonyl)oxy)hydroxylamine (5.5 g, 14.2 mmol). The mixture was stirred at room temperature for 4 h. The mixture was quenched with ice water (50 mL) and extracted with ethyl acetate (2×50 mL). The combined organic layers were washed with ice cold brine, then the organic layer was dried over anhydrous sodium sulfate and concentrated under reduced pressure. The residue was purified by silica gel column chromatography (eluent: 22-25% EtOAc in petroleum ether) to afford tert-butyl 3-oxo-3',6'-bis(((trifluoromethyl)sulfonyl)oxy)-3H-spiro[isobenzofuran-1,9'-xanthene]-6-carboxylate (2.0 g, 47% yield) as a solid. $^1$H NMR: (400 MHz, DMSO-$d_6$): δ 8.25 (d, 2H), 7.98 (s, 1H), 7.69 (s, 2H), 7.31-7.32 (d, 2H), 7.14-7.16 (d, 2H), 1.5 (s, 9H) ppm. m/z=697.5[M+H]+.

Intermediate B

Synthesis of methyl 3',6'-dibromo-3-oxo-3H-spiro[isobenzofuran-1,9'-xanthene]-6-carboxylate Intermediate B

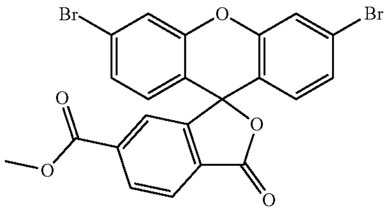

Step 1: Preparation of 3',6'-dibromo-3-oxo-3H-spiro[isobenzofuran-1,9'-xanthene]-6-carboxylate pyridinium salt Compound B1

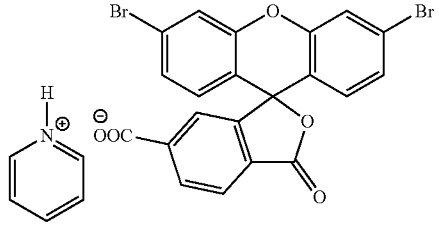

To a stirred solution 1,2,4-benzenetricarboxylic acid (50 g, 238 mmol) in methanesulfonic acid (250 mL) was added 3-bromophenol (86.4 g, 500 mmol). The mixture was stirred for 72 h at 140° C. After cooling to room temperature, the dark purple solution was poured into 200 mL of ice water and the slurry was stirred vigorously. The greenish yellow solid was collected by vacuum filtration and dried under suction. The solid was recrystallized from a mixture of 750 mL of acetic anhydride and 250 mL of pyridine, which provided a white solid. The white solid was recrystallized three additional times from the 2:1 mixture of acetic anhydride and pyridine to give 3',6'-dibromo-3-oxo-3H-spiro[isobenzofuran-1,9'-xanthene]-6-carboxylic acid pyridine salt (15.0 g, 12% yield) as powder. m/z=503.2 [M+H]+.

Step 2: Preparation of methyl 3',6'-dibromo-3-oxo-3H-spiro[isobenzofuran-1,9'-xanthene]-6-carboxylate Compound B2

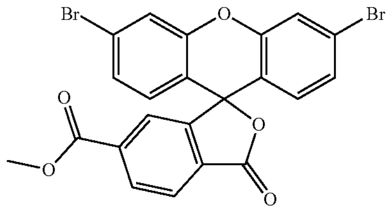

To a solution of 3',6'-dibromo-3-oxo-3H-spiro[isobenzofuran-1,9'-xanthene]-6-carboxylate pyridinium salt (10.0 g, 19.9 mmol) in MeOH (330 mL) was added $H_2SO_4$ (98%, 2.1 mL, 39.8 mmol) dropwise at room temperature. The mixture was stirred at 80° C. for 72 h. The mixture was cooled to room temperature and concentrated under reduced pressure. Saturated aqueous sodium bicarbonate (50 mL) was added until the reaction was basic (pH of >7) and then the aqueous solution was extracted with 10% IPA in $CHCl_3$ (2×100 mL). The combined organic layers were dried over anhydrous sodium sulfate and concentrated under reduced pressure. The residue was purified by silica gel column chromatography (eluent: 10% EtOAc in petroleum ether) to afford methyl 3',6'-dibromo-3-oxo-3H-spiro[isobenzofuran-1,9'-xanthene]-6-carboxylate (6.0 g, 58% yield) as a solid. m/z 517.12 [M+H]+.

Intermediate C

Synthesis of tert-butyl 3',6'-dibromo-3-oxo-3H-spiro[isobenzofuran-1,9'-xanthene]-6-carboxylate Intermediate C

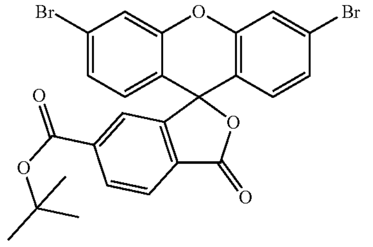

To a solution of 3',6'-dibromo-3-oxo-3H-spiro[isobenzofuran-1,9'-xanthene]-6-carboxylic acid pyridine salt (4.0 g, 8.0 mmol, Compound B1) in toluene (16 mL) was added 1,1-di-tert-butoxy-N,N-dimethylmethanamine (9.2 g, 47.2 mmol) and the mixture was stirred under reflux for 24 h. The mixture was concentrated under reduced pressure to afford tert-butyl 3',6'-dibromo-3-oxo-3H-spiro[isobenzofuran-1,9'-xanthene]-6-carboxylate as a brownish solid, which was used without further purification.

Intermediate D'

Synthesis of 3',6'-dibromo-N-(2-(2-((6-chlorohexyl)oxy)ethoxy)ethyl)-3-oxo-3H-spiro[isobenzofuran-1,9'-xanthene]-6-carboxamide Intermediate D'

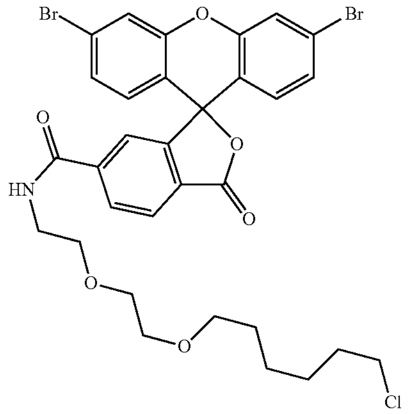

To a solution of 3',6'-dibromo-3-oxo-3H-spiro[isobenzofuran-1,9'-xanthene]-6-carboxylic acid pyridine salt (0.5 g, 1.0 mmol, Compound B1) and 2-(2-((6-chlorohexyl)oxy)ethoxy)ethan-1-amine (0.56 g, 2.5 mmol) in DMF (5.0 mL) at 0° C. was added N,N'-diisopropylethylamine (0.52 mL, 3.0 mmol). A solution of T3P (50% in ethyl acetate; 0.8 g, 2.5 mmol) was added drop wise at 0° C. The mixture was warmed to rt and stirred for 16 h. Ice cold water (50 mL) was added and the mixture was extraction with ethyl acetate (3×). The combined organic layers were washed with saturated aqueous sodium bicarbonate (2×) at 0° C. and brine (3×) at 0° C. The organic layer was dried over sodium sulfate and concentrated under reduced pressure. The reside was purified by silica gel column chromatography (eluent: 0-50% EtOAc in petroleum ether) to afford 3',6'-dibromo-N-(2-(2-((6-chlorohexyl)oxy)ethoxy)ethyl)-3-oxo-3H-spiro[isobenzofuran-1,9'-xanthene]-6-carboxamide (0.3 g, 42% yield) as an off white solid.

9.1 Example 1

Synthesis of dimethyl 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylate Compound 1

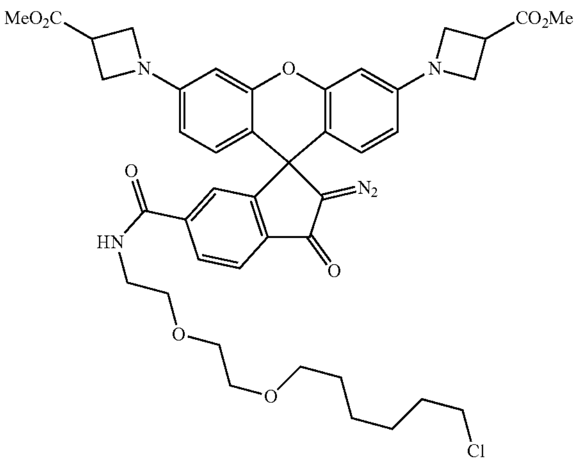

Step 1: Preparation of dimethyl 1,1'-(6-(tert-butoxycarbonyl)-3-oxo-3H-spiro[isobenzofuran-1,9'-xanthene]-3',6'-diyl)bis(azetidine-3-carboxylate Compound 1.1

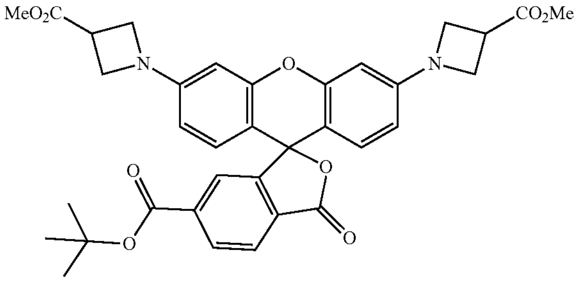

To a solution of tert-butyl 3-oxo-3',6'-bis(((trifluoromethyl)sulfonyl)oxy)-3H-spiro[isobenzofuran-1,9'-xanthene]-6-carboxylate (1.0 g, 1.4 mmol, Intermediate A) and methyl azetidine-3-carboxylate hydrochloride salt (0.55 g, 3.59 mmol) in dioxane (20 mL) was added $Cs_2CO_3$ (1.4 g, 4.3 mmol). The mixture was purged with argon gas for 15-20 min, then charged with $Pd_2(dba)_3$ (0.13 g, 0.14 mmol) and XPhos (0.14 g, 0.29 mmol). The mixture was stirred for 16 h at 100° C. The mixture was cooled to room temperature and filtered through pad of celite. The filtrate was diluted with water (50 mL) and extracted with ethyl acetate (2×50 mL). The combined organic layers were dried over anhydrous sodium sulfate and concentrated under reduced pressure. The residue was purified by silica gel column chromatography (eluent: 85% EtOAc in petroleum ether) to afford dimethyl 1,1'-(6-(tert-butoxycarbonyl)-3-oxo-3H-spiro[isobenzofuran-1,9'-xanthene]-3',6'-diyl)bis(azetidine-3-carboxylate) (0.35 g, 39% yield) as a solid. m/z=627.8 [M+H]+.

Step 2: Preparation of 3',6'-bis(3-(methoxycarbonyl)azetidin-1-yl)-3-oxo-3H-spiro[isobenzofuran-1,9'-xanthene]-6-carboxylic acid Compound 1.2

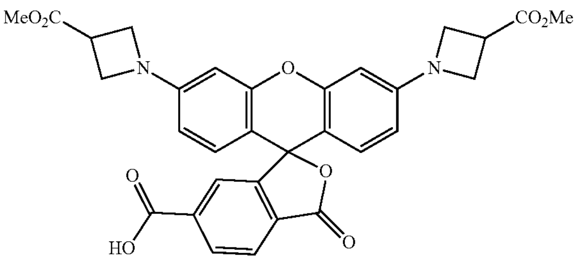

To a solution of dimethyl 1,1'-(6-(tert-butoxycarbonyl)-3-oxo-3H-spiro[isobenzofuran-1,9'-xanthene]-3',6'-diyl)bis(azetidine-3-carboxylate) (0.25 g, 0.40 mmol) in $CH_2Cl_2$ (2 mL) at 0° C. was added TFA (0.2 mL) drop wise. The mixture was stirred for 12 h at room temperature, then concentrated under reduced pressure. The residue was triturated with n-pentane, then diethyl ether to afford 3',6'-bis(3-(methoxycarbonyl)azetidin-1-yl)-3-oxo-3H-spiro[isobenzofuran-1,9'-xanthene]-6-carboxylic acid (180 mg, 79% yield) as a solid. m/z=571.9 [M+H]+.

Step 3: Preparation of dimethyl 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylate Compound 1.3

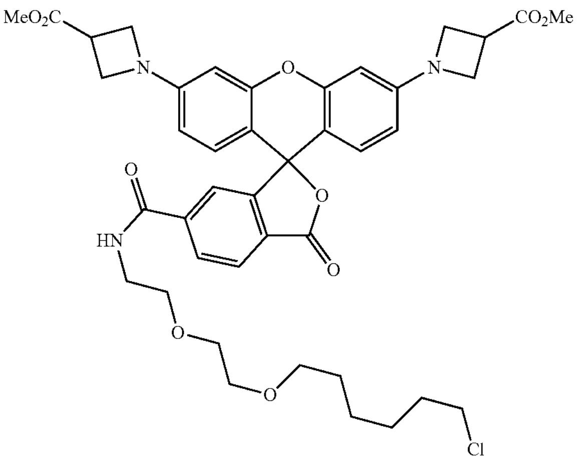

To a solution of 3',6'-bis(3-(methoxycarbonyl)azetidin-1-yl)-3-oxo-3H-spiro[isobenzofuran-1,9'-xanthene]-6-carboxylic acid (0.18 g, 0.35 mmol) in DMF (3.6 mL) at 0° C. was added triethylamine (0.27 mL, 1.9 mmol) followed by N,N'-Disuccinimidyl carbonate (0.18 g, 0.69 mmol) and DMAP (3.9 mg, 0.032 mmol). The mixture was stirred at 0° C. for 1 h. Then, a solution of 2-(2-((6-chlorohexyl)oxy)ethoxy) ethan-1-amine (0.17 g, 0.79 mmol) in DMF (0.8 mL) was added dropwise. The mixture was warmed to room temperature and stirred for 12 h. The mixture was diluted with ice cold water (20 mL) and extracted with ethyl acetate (2×20 mL). The combined organic layers were dried over anhydrous sodium sulfate and concentrated under reduced pressure. The residue was purified by silica gel column chromatography (eluent: 87% EtOAc in petroleum ether) to afford dimethyl 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylate) (0.18 g, 66% yield) as a solid. m/z 777.0[M+H]+.

Step 4: Preparation of dimethyl 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylate Compound 1.4

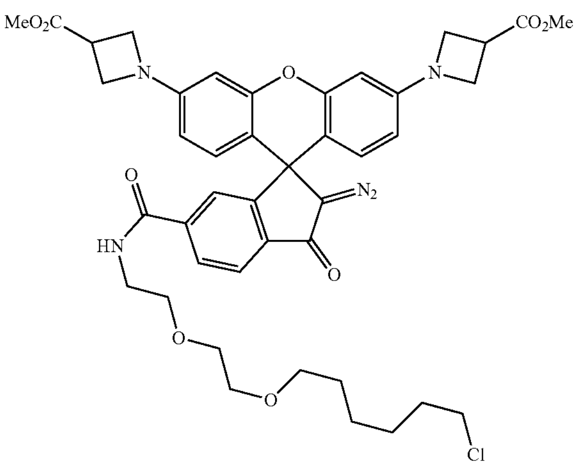

To a solution of dimethyl 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylate) (0.15 g, 0.20 mmol) in $CH_2Cl_2$ (6 mL) at 0° C. was added oxalyl chloride (2 M solution in $CH_2Cl_2$, 0.18 mL, 1.94 mmol). The mixture was warmed to room temperature and stirred for 30 min, followed by concentration under reduced pressure. The residue was dissolved in dry $CH_2Cl_2$ (20 mL) and freshly prepared diazomethane in $Et_2O$ (see, e.g., F. Arndt, "Diazomethane," Org. Synth. 1935, 15, 3) (~0.5 M, 5 mmol) was added at 0° C. and stirred for 30 min. The mixture was concentrated under reduced pressure and the residue was purified by silica gel column purification (eluent: 22% EtOAc in petroleum ether). The residue was further purified by chiral SFC (Chiralcel-OJ-3; mobile phase 30% MeOH in $CO_2$) to afford dimethyl 1,1'-(6-((2-(2-((6-chlorohexyl)oxy)ethoxy)ethyl)carbamoyl)-2-diazo-3-oxo-2, 3-dihydrospiro[indene-1,9'-xanthene]-3',6'-diyl)bis(azetidine-3-carboxylate) (0.03 g, 19% yield) as a solid. $^{1}H$ NMR (400 MHz, DMSO-$d_6$): δ 8.69 (t, J=5.6 Hz, 1H), 7.99-7.96 (m, 1H), 7.85 (d, J=8.0 Hz, 1H), 7.47 (s, 1H), 6.72 (d, J=8.4 Hz, 2H), 6.25 (d, J=2.4 Hz, 2H), 6.19-6.16 (m, 2H), 4.07-4.03 (m, 4H), 3.94-3.89 (m, 4H), 3.67 (s, 6H), 3.65-3.57 (m, 4H), 3.48-3.40 (m, 10H), 1.67-1.64 (m, 2H), 1.43-1.39 (m, 2H), 1.33-1.31 (m, 2H), 1.25-1.23 (m, 2H) ppm. m/z=800.3 [M+H]+.

9.2 Example 2

Synthesis of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid Compound 2

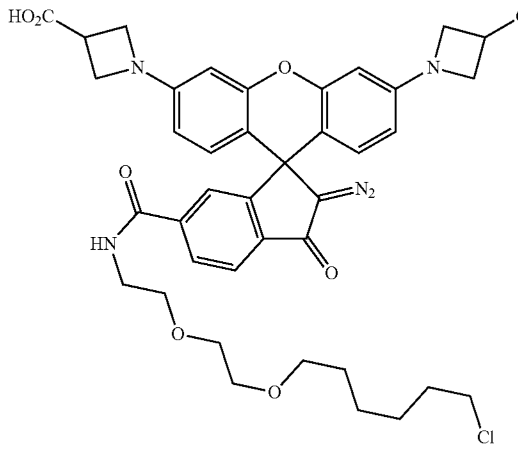

To a solution of dimethyl 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylate) (18 mg, 0.022 mmol, Example 1) in MeOH (0.2 mL) and THE (0.1 mL) at 0° C. was added a solution of LiOH (5 mg, 0.11 mmol) in water (0.1 mL). The mixture was stirred for 24 h at room temperature. The mixture was concentrated under reduced pressure, then the residue was purified using achiral SFC (YMC-PAK DIOL; mobile phase, 30% MeOH in $CO_2$) to afford 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid) (11 mg, 63%) as a solid. $^{1}H$ NMR (400 MHz, DMSO-$d_6$): δ 8.69 (t, J=8.0 Hz, 1H), 7.96 (d, J=8.0 Hz, 1H), 7.82 (d, J=8.0 Hz, 1H), 7.48 (s, 1H), 6.66 (d, J=8.8 Hz, 2H), 6.18-6.10 (m, 4H), 3.92-3.82 (m, 8H), 3.60 (t, J=13.2 Hz, 2H), 3.46-3.39 (m, 12H), 1.65 (t, J=14.8 Hz, 2H), 1.42-1.28 (m, 4H), 1.24-1.22 (m, 2H). m/z=770.23 [M+H]+.

9.3 Example 3

Synthesis of N-(2-(2-((6-chlorohexyl)oxy)ethoxy)ethyl)-2-diazo-3',6'-bis((R)-2-(methoxymethyl)azetidin-1-yl)-3-oxo-2,3-dihydrospiro[indene-1,9'-xanthene]-6-carboxamide Compound 3

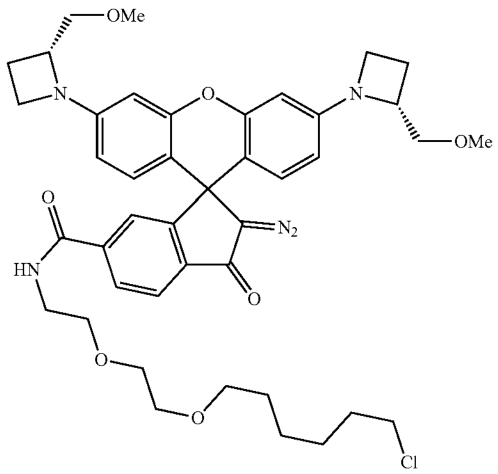

Step 1: Preparation of methyl 3',6'-bis((R)-2-(methoxymethyl)azetidin-1-yl)-3-oxo-3H-spiro[isobenzofuran-1,9'-xanthene]-6-carboxylate Compound 3.1

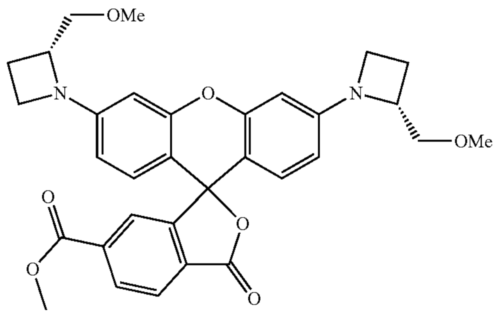

To a solution of methyl 3',6'-dibromo-3-oxo-3H-spiro[isobenzofuran-1,9'-xanthene]-6-carboxylate (0.50 g, 0.96 mmol, Intermediate B), (R)-2-(methoxymethyl)azetidine (0.24 g, 2.42 mmol) in 1,4-dioxane (10 mL) in a microwave vessel was added cesium carbonate (0.95 g, 2.9 mmol). The mixture was purged with argon gas for 15-20 min, then $Pd_2(dba)_3$ (0.09 g, 0.097 mmol) and RuPhos Pd G4 (0.14 g, 0.29 mmol) were added. The mixture was stirred for 2 h at 110° C. The mixture was filtered through celite, then the filtrate was diluted with water (50 mL), and extracted with EtOAc (2×50 mL). The combined organic layers were dried over anhydrous sodium sulfate and concentrated under reduced pressure. The residue was purified by silica gel column chromatography (eluent: 85% EtOAc in petroleum ether) to afford methyl 3',6'-bis((R)-2-(methoxymethyl)azetidin-1-yl)-3-oxo-3H-spiro[isobenzofuran-1,9'-xanthene]-6-carboxylate (0.17 g, 31% yield) as a solid. m/z 557.52 [M+H]+.

Step 2: Preparation of 3',6'-bis((R)-2-(methoxymethyl)azetidin-1-yl)-3-oxo-3H-spiro[isobenzofuran-1,9'-xanthene]-6-carboxylic acid Compound 3.2

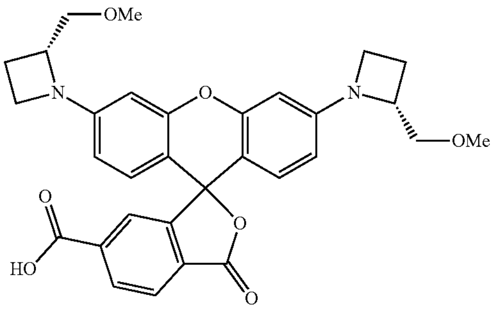

To a solution of methyl 3',6'-bis((R)-2-(methoxymethyl)azetidin-1-yl)-3-oxo-3H-spiro[isobenzofuran-1,9'-xanthene]-6-carboxylate (0.17 g, 0.30 mmol) in MeOH (1.0 mL) and THE (0.5 mL) at 0° C. was added a solution of LiOH (0.06 g, 1.53 mmol) in water (0.5 mL). The mixture was stirred for 24 h at room temperature. The mixture was concentrated under reduced pressure to half volume and then was diluted with water (5 mL) and extracted with EtOAc (10 mL). Aqueous layer was acidified with 1N HCl and extracted with 10% MeOH in $CH_2Cl_2$ (50 ml). The organic layer was dried over anhydrous sodium sulfate and concentrated under reduced pressure. The residue was purified by preparatory HPLC (C18, mobile phase, 20% ACN/water (0.05% formic acid) to afford 3',6'-bis((R)-2-(methoxymethyl)azetidin-1-yl)-3-oxo-3H-spiro[isobenzofuran-1,9'-xanthene]-6-carboxylic acid (0.12 g, 72% yield) as a solid. m/z=543.45 [M+H]+.

Step 3: Preparation of N-(2-(2-((6-chlorohexyl)oxy)ethoxy)ethyl)-3',6'-bis((R)-2-(methoxymethyl)azetidin-1-yl)-3-oxo-3H-spiro[isobenzofuran-1,9'-xanthene]-6-carboxamide Compound 3.3

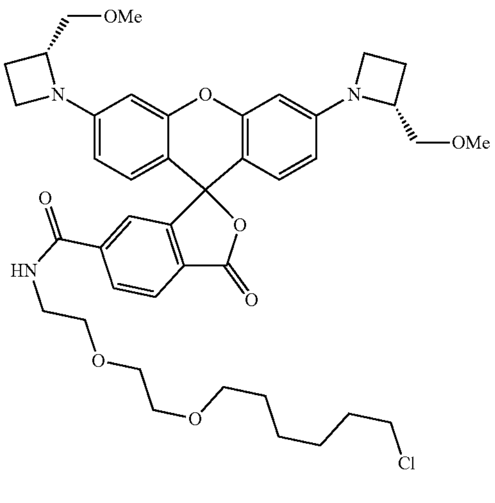

To a stirred solution of 3',6'-bis((R)-2-(methoxymethyl)azetidin-1-yl)-3-oxo-3H-spiro[isobenzofuran-1,9'-xanthene]-6-carboxylic acid (0.12 g, 0.22 mmol) in DMF (1.2 mL) at 0° C. was added N,N'-diisopropylethylamine (0.12 mL, 0.66 mmol) and 2-(2-((6-chlorohexyl)oxy)ethoxy)ethan-1-amine (0.099 g, 0.442 mmol) in DMF (0.1 mL) at 0° C. The mixture was stirred at 0° C. for 10 min and then propylphosphonic anhydride (50% in ethyl acetate; 0.18 g, 0.550 mmol) was added dropwise. The mixture was warmed to room temperature and stirred for 16 h. The mixture was diluted with ice cold water (20 mL) and extracted with ethyl acetate (2×20 mL). The combined organic layers were washed with brine, dried over anhydrous sodium sulfate and concentrated under reduced pressure. The residue was purified by silica gel column chromatography (eluent: 6% MeOH in $CH_2Cl_2$) to afford N-(2-(2-((6-chlorohexyl)oxy)ethoxy)ethyl)-3',6'-bis((R)-2-(methoxymethyl)azetidin-1-yl)-3-oxo-3H-spiro[isobenzofuran-1,9'-xanthene]-6-carboxamide (110 mg, 66% yield) as pink solid. m/z=749.14 [M+H]+.

Step 4: Preparation of N-(2-(2-((6-chlorohexyl)oxy)ethoxy)ethyl)-2-diazo-3',6'-bis((R)-2-(methoxymethyl)azetidin-1-yl)-3-oxo-2,3-dihydrospiro[indene-1,9'-xanthene]-6-carboxamide Compound 3.4

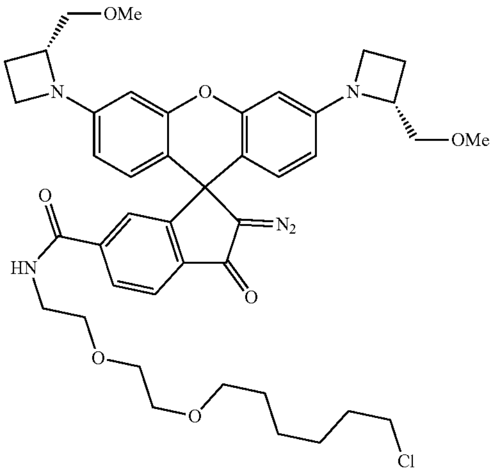

To a solution of N-(2-(2-((6-chlorohexyl)oxy)ethoxy)ethyl)-3',6'-bis((R)-2-(methoxymethyl)azetidin-1-yl)-3-oxo-3H-spiro[isobenzofuran-1,9'-xanthene]-6-carboxamide (0.09 g, 0.12 mmol) in $CH_2Cl_2$ (5 mL) at 0° C. was added oxalyl chloride (0.10 mL, 1.20 mmol). The mixture was warmed to room temperature and stirred at room temperature for 30 min. The mixture was concentrated with a stream of nitrogen gas. The residue was dissolved in dry $CH_2Cl_2$ (20 mL) and freshly prepared diazomethane (see, e.g., F. Arndt, "Diazomethane," *Org. Synth.* 1935, 15, 3) in $Et_2O$ (~0.5 M, 3 mmol) was added at 0° C. Mixture was stirred at 0° C. for 30 min then concentrated under reduced pressure. The residue was purified by flash column purification using neutral alumina (eluent: 0-10% Acetone in petroleum ether). The residue was further purified by achiral SFC (YMC PAK-DIOL; mobile phase, 25% MeOH in $CO_2$) to afford N-(2-(2-((6-chlorohexyl)oxy)ethoxy)ethyl)-2-diazo-3',6'-bis((R)-2-(methoxymethyl)azetidin-1-yl)-3-oxo-2,3-dihydrospiro[indene-1,9'-xanthene]-6-carboxamide (0.0032 g, 3%) as a solid. $^1$H NMR (400 MHz, DMSO-$d_6$): δ 8.69 (t, J=5.2 Hz, 1H), 7.98 (d, J=7.2 Hz, 1H), 7.84 (d, J=8.0 Hz, 1H), 7.46 (s, 1H), 6.68 (d, J=8.4 Hz, 2H), 6.38 (s, 2H), 6.29-6.27 (m, 2H), 4.17-4.16 (m, 2H), 3.84 (bs, 2H), 3.60-3.37 (m, 24H), 2.32-2.27 (m, 2H), 2.13-2.07 (m, 2H), 1.67-1.63 (m, 2H), 1.42-1.29 (m, 6H) ppm. m/z=772.7 [M+H]+.

9.4 Example 4

Synthesis of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylazetidine-3-carboxamide Compound 4

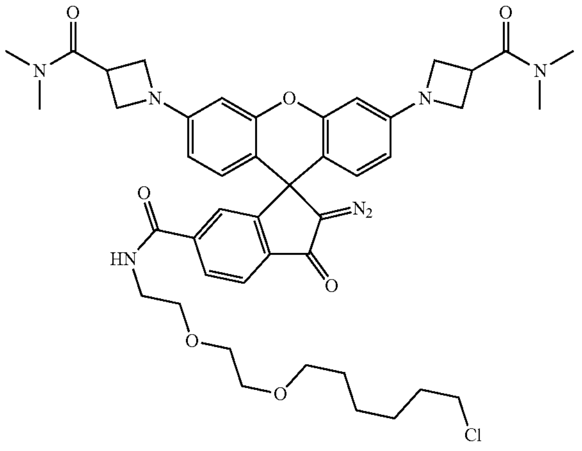

Step 1: Preparation of methyl 3',6'-bis(3-(dimethylcarbamoyl)azetidin-1-yl)-3-oxo-3H-spiro[isobenzofuran-1,9'-xanthene]-6-carboxylate

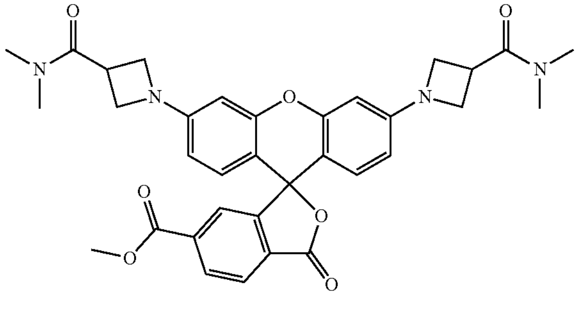

A mixture of methyl 3',6'-dibromo-3-oxo-3H-spiro[isobenzofuran-1,9'-xanthene]-6-carboxylate (1.0 g, 1.94 mmol, Intermediate B), N,N-dimethylazetidine-3-carboxamide hydrochloride (0.62 g, 4.84 mmol) and cesium carbonate (1.90 g, 5.810 mmol) in a microwave vessel was suspended in anhydrous 1,4-dioxane (10.0 mL). The vial was degassed with nitrogen for 15 min then $Pd_2(dba)_3$ (0.18 g, 0.19 mmol) and RuPhos Pd G4 (0.27 g, 0.50 mmol) were added. The mixture was stirred for 2 h at 110° C. The mixture was filtered through celite and washed with 10% MeOH in $CH_2Cl_2$ (100 mL). The filtrate was evaporated under reduced pressure and the residue was purified by silica gel column chromatography (eluent: 0-20% MeOH in $CH_2Cl_2$) to afford methyl 3',6'-bis(3-(dimethylcarbamoyl)azetidin-1-yl)-3-oxo-3H-spiro[isobenzofuran-1,9'-xanthene]-6-carboxylate (0.28 g, 23% yield) as a solid. m/z 612.0 [M+H]+.

Step 2: Preparation of 3',6'-bis(3-(dimethylcarbamoyl)azetidin-1-yl)-3-oxo-3H-spiro[isobenzofuran-1,9'-xanthene]-6-carboxylic acid

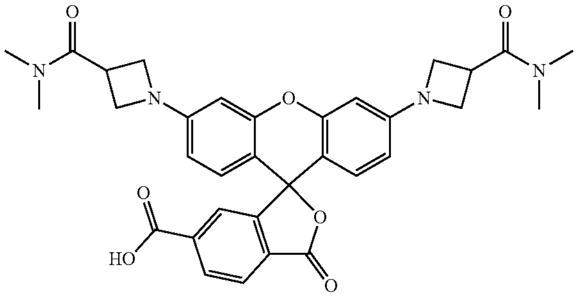

To a solution of methyl 3',6'-bis(3-(dimethylcarbamoyl)azetidin-1-yl)-3-oxo-3H-spiro[isobenzofuran-1,9'-xanthene]-6-carboxylate (0.28 g, 0.46 mmol) in THE (2.8 mL) at 0° C. was added trimethyltin hydroxide (0.5 g, 2.75 mmol). The mixture was warmed to room temperature and stirred for 2 h. Water (2 mL) was added then the mixture was cooled to 0° C. and acidified to pH 5 with 1N HCl. The aqueous layer was extracted with 10% isopropanol in chloroform (3×30 mL). The combined organic layers were dried over sodium sulfate and concentrated under reduced pressure. The residue was purified by preparatory HPLC (C18; mobile phase, 0-100% ACN/water (0.05% formic acid) to afford 3',6'-bis(3-(dimethylcarbamoyl)azetidin-1-yl)-3-oxo-3H-spiro[isobenzofuran-1,9'-xanthene]-6-carboxylic acid (0.23 g, 84% yield) as a solid. m/z 597.41 [M+H]+.

Step 3: Preparation of 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(N,N-dimethylazetidine-3-carboxamide Compound 4.3

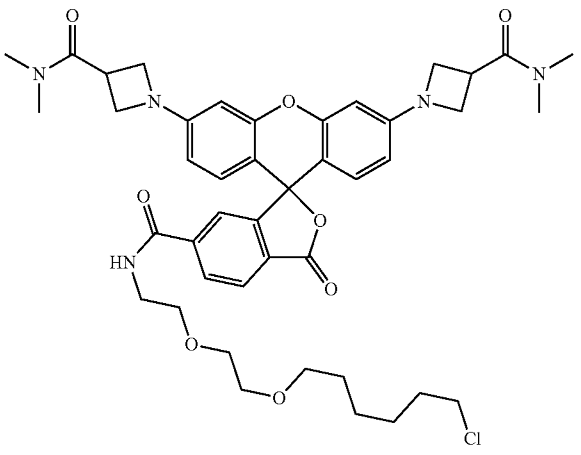

To a solution of 3',6'-bis(3-(dimethylcarbamoyl)azetidin-1-yl)-3-oxo-3H-spiro[isobenzofuran-1,9'-xanthene]-6-carboxylic acid (0.23 g, 0.39 mmol) and 2-(2-((6-chlorohexyl)oxy)ethoxy)ethan-1-amine (0.17 g, 0.77 mmol) in DMF (2.3 mL) at 0° C. and was added diisopropylethylamine (0.2 mL, 1.15 mmol). The mixture was stirred at 0° C. for 10 min and then propylphosphonic anhydride solution (50% in ethyl acetate; 0.3 g, 0.96 mmol) was added dropwise. The mixture was warmed to room temperature and stirred for 16 h. The mixture was diluted with ice cold water (10 mL) and extracted with ethyl acetate (2×20 mL). The combined organic layers were washed with brine (50 mL) and ice-cold water (30 mL). The organic layer was dried over anhydrous sodium sulfate and concentrate under reduced pressure. The residue was purified by silica gel column chromatography (eluent: 0-8% MeOH in $CH_2Cl_2$) to afford 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(N,N-dimethylazetidine-3-carboxamide) (0.20 g, 64% yield) as a solid. m/z 802.73[M+H]+.

Step 4: Preparation of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis (N,N-dimethylazetidine-3-carboxamide Compound 4.4

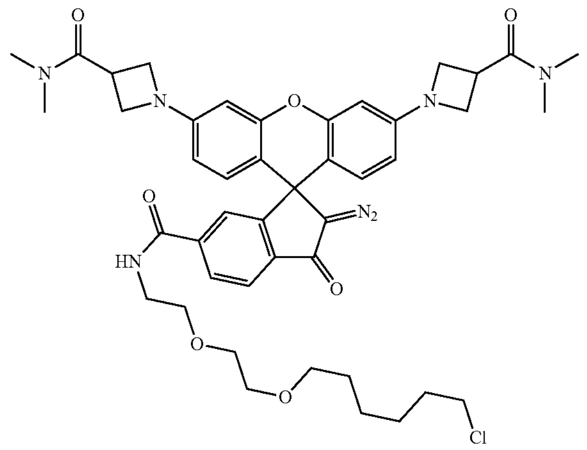

To a solution of 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(N,N-dimethylazetidine-3-carboxamide) (0.07 g, 0.087 mmol) in $CH_2Cl_2$ (4 mL) at 0° C. was added oxalyl chloride (0.07 mL, 0.872 mmol). The mixture was warmed to room temperature and stirred for 30 min. The mixture was concentrated under reduced pressure. The residue was dissolved in dry $CH_2C_2$ (20 mL) and freshly prepared diazomethane in $Et_2O$ (see, e.g., F. Arndt, "Diazomethane," Org. Synth. 1935, 15, 3) (~0.5 M, 2.2 mmol) was added at 0° C. Mixture was stirred at 0° C. for 30 min. The mixture was concentrated under reduced pressure and the residue was purified by flash column purification using neutral alumina (eluent: 0-5% MeOH in $CH_2Cl_2$). The residue was further purified by SFC (DCPAK P4VP; mobile phase, 45% (0.2% DEA in ACN) in $CO_2$) to afford 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylazetidine-3-carboxamide) (0.0052 g, 7% yield) as a solid. $^1$H NMR (400 MHz, DMSO-$d_6$): δ 8.70 (t, J=5.6 Hz, 1H), 7.99-7.96 (m, 1H), 7.83 (d, J=8.0 Hz, 1H), 7.47 (s, 1H), 6.70 (d, J=8.4 Hz, 2H), 6.22 (d, J=8.4 Hz, 2H), 6.17 (d, J=8.4 Hz, 2H), 4.04-4.01 (m, 4H), 3.91-3.81 (m, 6H), 3.60 (t, J=6.4 Hz, 2H), 3.46-3.39 (m, 8H), 3.32-3.28 (m, 2H), 2.88 (s, 6H), 2.83 (s, 6H), 1.67-1.63 (m, 2H), 1.42-1.28 (m, 4H), 1.24-1.22 (m, 2H) ppm. m/z=826.63 [M+H]+.

9.5 Example 5

Synthesis of 1,1'-(6-((4-(((2-amino-7H-purin-6-yl)oxy)methyl)benzyl)carbamoyl)-2-diazo-3-oxo-2,3-dihydrospiro[indene-1,9'-xanthene]-3',6'-diyl)bis(N,N-dimethylazetidine-3-carboxamide Compound 5

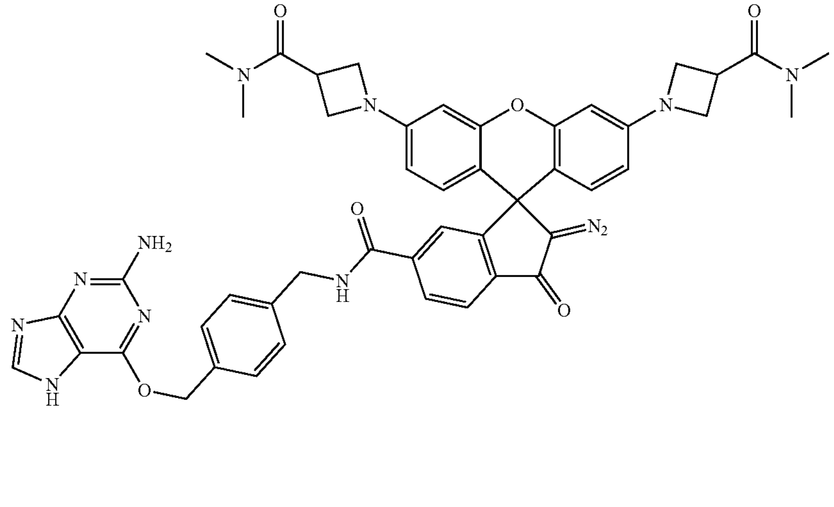

Step 1: Preparation of 2-diazo-3',6'-bis(3-(dimethylcarbamoyl)azetidin-1-yl)-3-oxo-2,3-dihydrospiro[indene-1,9'-xanthene]-6-carboxylic acid Compound 5.1

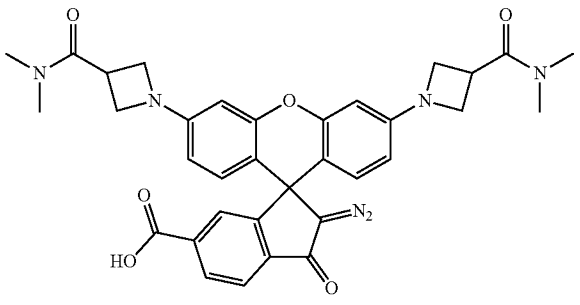

The title compound was prepared using similar procedure as Example 7, Steps 1-3 replacing azetidin-3-ol-hydrochloride with N,N-dimethylazetidine-3-carboxamide-hydrochloride in Step 1. The residue was purified by trituration with diethyl ether to afford 2-diazo-3',6'-bis(3-(dimethylcarbamoyl) azetidin-1-yl)-3-oxo-2,3-dihydrospiro[indene-1,9'-xanthene]-6-carboxylic acid as a brown solid.

Step 2: Preparation of 1,1'-(6-((4-(((2-amino-7H-purin-6-yl)oxy)methyl)benzyl)carbamoyl)-2-diazo-3-oxo-2,3-dihydrospiro[indene-1,9'-xanthene]-3',6'-diyl)bis(N,N-dimethylazetidine-3-carboxamide Compound 5.2

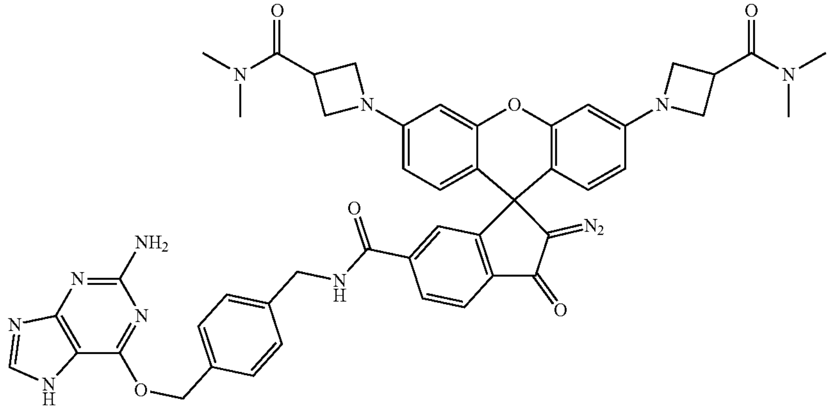

To a stirred solution of 3',6'-bis(3-(dimethylcarbamoyl) azetidin-1-yl)-3-oxo-3H-spiro[isobenzofuran-1,9'-xanthene]-6-carboxylic acid (0.05 g, 0.081 mmol, Compound 4.2) and 6-((4-(aminomethyl) benzyl)oxy)-7H-purin-2-amine (0.05 g, 0.161 mmol) in DMF (1 mL) was added diisopropylethylamine (0.06 g, 0.403 mmol) at 0° C. After 10 min propylphosphonic anhydride solution (50% in ethyl acetate; 0.22 g, 0.32 mmol) was added dropwise at 0° C. The mixture was warmed to rt and stirred at rt for 3 h. The mixture was concentrated and the residue was purified by preparatory HPLC (column: X-BRIDGE C8; mobile phase, 0-100% ACN in water) to afford the title compound (0.008 g, 12%) as a light brown solid. $^{1}$H NMR (400 MHz, DMSO-$d_6$): δ 9.21 (t, J=12.0 & 6.0 Hz, 1H), 8.21 (s, 1H), 8.02 (d, J=8.4 Hz, 1H), 7.85 (d, J=8.0 Hz, 1H), 7.50 (s, 1H), 7.44 (d, J=8 Hz, 2H), 7.27 (d, J=8.0 Hz, 2H), 6.70 (d, J=8.4 Hz, 4H), 6.21 (s, 2H), 6.16 (d, J=8.4 Hz, 2H), 5.46 (s, 2H), 4.45-4.35 (m, 2H), 4.06-4.01 (m, 4H), 3.91-3.81 (m, 6H), 2.88 (s, 6H), 2.83 (s, 6H) ppm. m/z=873.3 [M+H]+.

9.6 Example 6

Synthesis of Dimethyl 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl) (2R,2'R)-bis(azetidine-2-carboxylate Compound 6

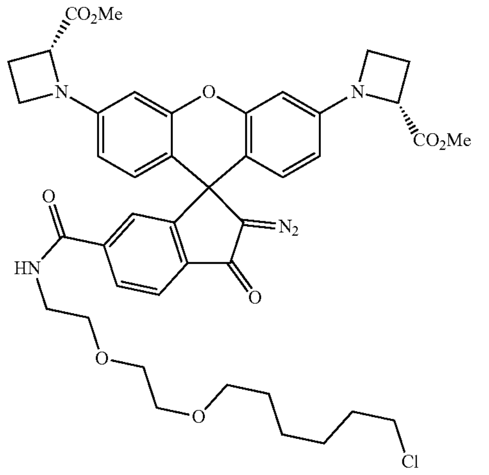

The title compound was prepared using similar procedure as Example 1, Steps 1-4, replacing methyl azetidine-3-carboxylate hydrochloride salt with methyl (R)-azetidine-2-carboxylate hydrochloride salt in Step 1 and replacing Intermediate A with Intermediate C in Step 1. The residue was purified by preparatory HPLC (column: XBridge C18; mobile phase: 0-100% ACN in water) to afford the title compound (0.0032 g, 16% yield) as a pale-yellow solid. $^1$H NMR (400 MHz, DMSO-$d_6$): δ 8.71-8.69 (m, 1H), 7.96 (d, J=8.4 Hz, 1H), 7.85 (d, J=8 Hz, 1H), 7.44 (d, J=4.8 Hz, 1H), 6.72 (d, J=8.8 Hz, 2H), 6.28 (dd, J=3.2 Hz, 2H), 6.24-6.21 (m, 2H), 4.68-4.63 (m, 2H), 3.89-3.81 (m, 2H), 3.71-3.67 (m, 8H), 3.61-3.57 (m, 2H), 3.48-3.40 (m, 6H), 3.31-3.29 (m, 4H), 2.53-2.48 (m, 4H), 1.67-1.64 (m, 2H), 1.41-1.20 (m, 6H) ppm. m/z=800.6 [M+H]+.

9.7 Example 7

Synthesis of N-(2-(2-((6-chlorohexyl)oxy)ethoxy)ethyl)-2-diazo-3',6'-bis(3-hydroxyazetidin-1-yl)-3-oxo-2,3-dihydrospiro[indene-1,9'-xanthene]-6-carboxamide Compound 7

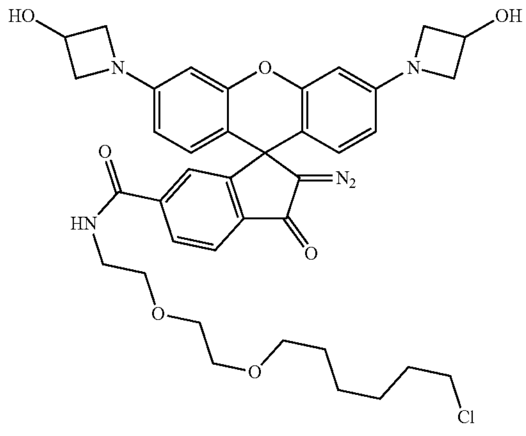

Step 1: Preparation of methyl 3',6'-bis(3-hydroxyazetidin-1-yl)-3-oxo-3H-spiro[isobenzofuran-1,9'-xanthene]-6-carboxylate Compound 7.1

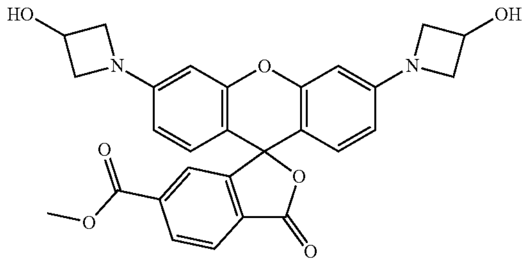

To a stirred solution of methyl 3',6'-dibromo-3-oxo-3H-spiro[isobenzofuran-1,9'-xanthene]-6-carboxylate (Intermediate B, 2.0 g, 3.88 mmol) and azetidin-3-ol-hydrochloride (1.06 g, 9.69 mmol) in 1,4-dioxane (40 mL) was added cesium carbonate (6.31 g, 19.38 mmol) at rt. The mixture was purged with argon for 20 min then $Pd_2(dba)_3$ (0.35 g, 0.38 mmol) and Xphos (0.55 g, 1.16 mmol) were added. The mixture was purged with argon for 10 min and heated to 120° C. for 16 h. The mixture was cooled to rt and filtered through celite. The celite was washed with MeOH and the solution was concentrated under reduced pressure. The residue was purified by reverse phase column chromatography (column C-18 column; eluent: with 0-20% ACN/water in (0.1% formic acid)) to afford methyl 3',6'-bis(3-hydroxyazetidin-1-yl)-3-oxo-3H-spiro[isobenzofuran-1,9'-xanthene]-6-carboxylate (0.90 g, 47% yield)) as a violet solid.

Step 2: Preparation of methyl 2-diazo-3',6'-bis(3-hydroxyazetidin-1-yl)-3-oxo-2,3-dihydrospiro [indene-1,9'-xanthene]-6-carboxylate Compound 7.2

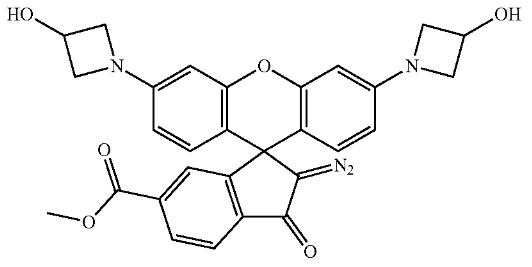

To a stirred solution of methyl 3',6'-bis(3-hydroxyazetidin-1-yl)-3-oxo-3H-spiro[isobenzofuran-1,9'-xanthene]-6-carboxylate (0.2 g, 0.4 mmol) in DCM (20 mL) at 0° C. was added oxalyl chloride (1 g, 8 mmol) dropwise. The mixture was warmed to rt and stirred at rt for 60 min. The mixture was concentrated under reduced pressure. The residue was dissolved in dry DCM (100 mL) and freshly prepared diazomethane in $Et_2O$ (~0.5 M, 100 mmol) was added at 0° C. dropwise. The mixture was stirred at 0° C. for 15 min and then warmed to rt. The mixture was stirred at rt for 15 min. The mixture was concentrated under reduced pressure. The residue was purified by silica gel column chromatography (eluent: 50-100% ethyl acetate in petroleum ether). The residue was further purified by SFC (column: YMC PACK DIOL-120; mobile phase: 20% MeOH in $CO_2$) to afford methyl-2-diazo-3',6'-bis(3-hydroxyazetidin-1-yl)-3-oxo-2,3-dihydrospiro[indene-1,9'-xanthene]-6-carboxylate (0.055 g, 7% yield) as a light brown solid.

Step 3: Preparation of 2-diazo-3',6'-bis(3-hydroxyazetidin-1-yl)-3-oxo-2,3-dihydrospiro[indene-1,9'-xanthene]-6-carboxylic acid Compound 7.3

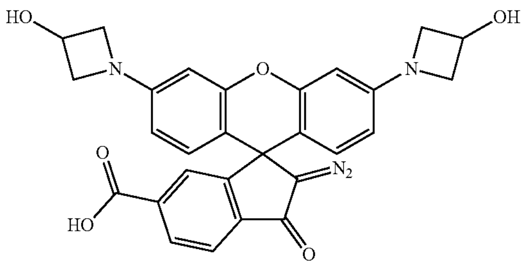

To a stirred solution of methyl-2-diazo-3',6'-bis(3-hydroxyazetidin-1-yl)-3-oxo-2,3-dihydrospiro[indene-1,9'-xanthene]-6-carboxylate (0.05 g, 0.095 mmol) in THE (1.0 mL), MeOH (0.5 mL) and water (0.5 mL) was added lithium hydroxide monohydrate (8 mg, 0.19 mmol) at 0° C. The mixture was stirred for 1 h at rt. The mixture was concentrated under reduced pressure and the reside was triturated with $Et_2O$ to afford 2-diazo-3',6'-bis(3-hydroxyazetidin-1-yl)-3-oxo-2,3-dihydrospiro[indene-1,9'-xanthene]-6-carboxylic acid (0.048 g, 98% yield) as a brown solid.

Step 4: Preparation of N-(2-(2-((6-chlorohexyl)oxy)ethoxy)ethyl)-2-diazo-3',6'-bis(3-hydroxyazetidin-1-yl)-3-oxo-2,3-dihydrospiro[indene-1,9'-xanthene]-6-carboxamide Compound 7.4

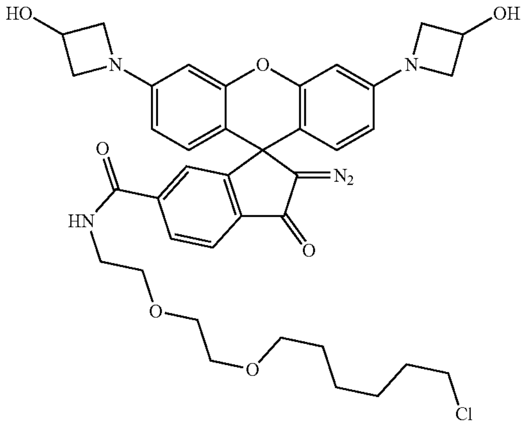

To a stirred solution of 2-diazo-3',6'-bis(3-hydroxyazetidin-1-yl)-3-oxo-2,3-dihydrospiro[indene-1,9'-xanthene]-6-carboxylic acid (0.048 g, 0.094 mmol) and 2-(2-((6-chlorohexyl)oxy)ethoxy)ethan-1-amine (0.053 g, 0.24 mmol) in DMF (1 mL) was added N,N'-diisopropylethylamine (0.05 g, 0.38 mmol) at 0° C. The mixture was stirred at 0° C. for 10 min, then propanephosphonic acid anhydride (50% in ethyl acetate; 0.18 g, 0.282 mmol) was added drop wise at 0° C. The mixture was warmed to rt and stirred for 2 h at rt. The mixture was concentrated under reduced pressure and purified by preparatory HPLC (column: XSELECT-C18; mobile phase 0-100% ACN in water) to afford N-(2-(2-((6-chlorohexyl)oxy)ethoxy)ethyl)-2-diazo-3',6'-bis(3-hydroxyazetidin-1-yl)-3-oxo-2,3-dihydrospiro [indene-1,9'-xanthene]-6-carboxamide (5 mg, 7% yield) as a light brown solid. $^1H$ NMR (400 MHz, DMSO-$d_6$): δ 8.68 (t, J=5.6 Hz, 1H), 7.96 (d, J=8.4 Hz, 1H), 7.83 (d, J=8.0 Hz, 1H), 7.46 (s, 1H), 6.68 (d, J=8.8 Hz, 2H), 6.19 (s, 2H), 6.14 (d, J=8.4 Hz, 2H), 5.60 (d, J=6.8 Hz, 2H), 4.57-4.52 (m, 2H), 4.09-4.05 (m, 4H), 3.61-3.41 (m, 16H) 1.68-1.62 (m, 2H), 1.43-1.37 (m, 2H), 1.37-1.30 (m, 2H), 1.30-1.23 (m, 2H) ppm. m/z=716.7[M+H]+.

9.8 Example 8

Synthesis of 3',6'-di(azetidin-1-yl)-N-(2-(2-((6-chlorohexyl)oxy)ethoxy)ethyl)-2-diazo-N-methyl-3-oxo-2,3-dihydrospiro[indene-1,9'-xanthene]-6-carboxamide Compound 8

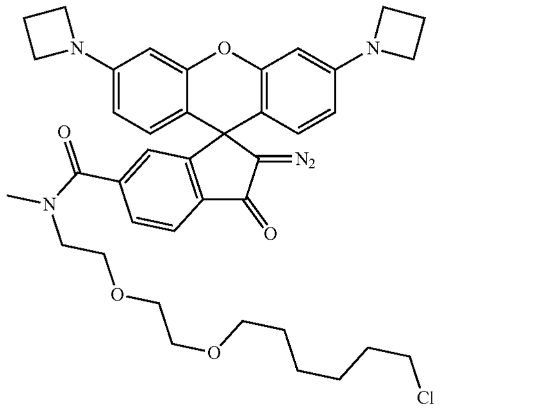

Step 1: Preparation of tert-butyl (2-(2-((6-chlorohexyl)oxy)ethoxy)ethyl)carbamate Compound 8.1

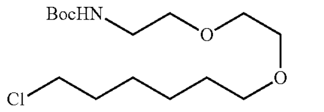

To a stirred solution of tert-butyl (2-(2-hydroxyethoxy)ethyl)carbamate (5.0 g, 24.4 mmol) in THE (35 mL) and DMF (18 mL) at 0° C. was added NaH (1.17 g, 60% in mineral oil, 29.2 mmol). The mixture was stirred at 0° C. for 30 min, then 6-chloro-1-iodohexane (8.4 g, 34.1 mmol) was added. The mixture was warmed to rt and stirred at rt for 30 min. A solution of saturated $NH_4Cl$ was added and the mixture was extracted with EtOAc (3×50 mL). The combined organic layers were washed with water and brine. The mixture was dried over $Na_2SO_4$ and concentrated under reduced pressure. The residue was purified by silica gel column chromatography (eluent: in 30% ethyl acetate in petroleum ether) to afford tert-butyl (2-(2-((6-chlorohexyl)oxy)ethoxy)ethyl)carbamate (2.6 g, 33% yield) as colorless oil.

Step 2: Preparation of tert-butyl (2-(2-((6-chlorohexyl)oxy)ethoxy)ethyl)(methyl)carbamate Compound 8.2

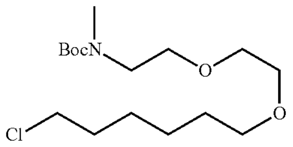

To a stirred solution of tert-butyl (2-(2-((6-chlorohexyl)oxy)ethoxy)ethyl)carbamate (3.0 g, 9.3 mmol) and methyl iodide (2.3 mL, 46.3 mmol) in DMF (50 mL) at 0° C. was added sodium hydride (60% dispersion in mineral oil; 0.93 g, 23.2 mmol). The mixture was warmed to rt and stirred at rt for 3 h. An aqueous solution of saturated $NH_4Cl$ (50 mL) was added and the mixture was extracted with ethyl acetate (3×50 mL). The combined organic layers were dried over $Na_2SO_4$ and concentrated under reduced pressure. The residue was purified by silica gel column chromatography (eluent: 5-10%, ethyl acetate in petroleum ether) to afford tert-butyl (2-(2-((6-chlorohexyl)oxy)ethoxy)ethyl)(methyl)carbamate (2.3 g, 45% yield) as a pale yellow oil.

Step 3: Preparation of 2-(2-((6-chlorohexyl)oxy)ethoxy)-N-methylethan-1-amine trifluoroacetate Compound 8.3

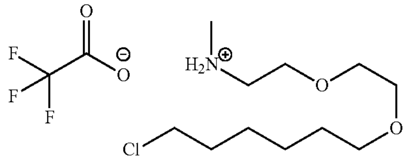

To a stirred solution of tert-butyl (2-(2-((6-chlorohexyl)oxy)ethoxy)ethyl)(methyl)carbamate (2.2 g, 6.5 mmol) in DCM (22 mL) at 0° C. was added trifluoroacetic acid (1.0 mL, 13.0 mmol). The mixture was warmed to rt and stirred at rt for 2 h. The mixture was concentrated under reduced pressure. The residue was triturated with $Et_2O$ to afford the title compound as a yellowish oil.

Step 4: Preparation of 3',6'-di(azetidin-1-yl)-2-diazo-3-oxo-2,3-dihydrospiro[indene-1,9'-xanthene]-6-carboxylic acid Compound 8.4

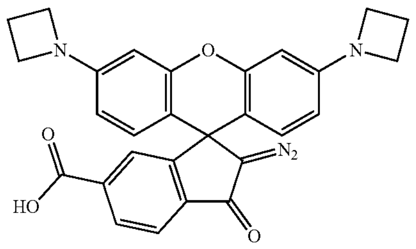

The title compound was prepared using similar procedure as Example 7, replacing azetidin-3-ol-hydrochloride with azetidine hydrochloride in Step 1. The residue was purified by silica gel column chromatography (eluent: 0-8% MeOH in DCM). The residue was further purified by preparatory HPLC (column: C18 RP; mobile phase: 0-100% ACN in water) to afford 3',6'-di(azetidin-1-yl)-2-diazo-3-oxo-2,3-dihydrospiro[indene-1,9'-xanthene]-6-carboxylic acid as a solid.

Step 5: Preparation of 3',6'-di(azetidin-1-yl)-N-(2-(2-((6-chlorohexyl)oxy)ethoxy)ethyl)-2-diazo-N-methyl-3-oxo-2,3-dihydrospiro[indene-1,9'-xanthene]-6-carboxamide Compound 8.5

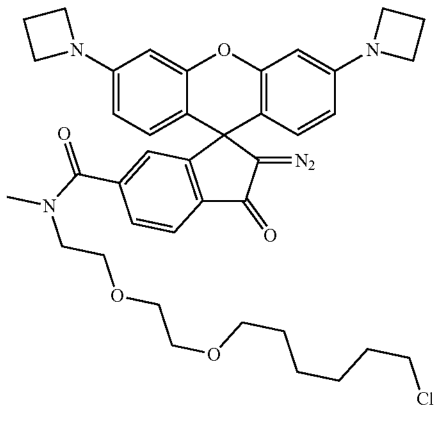

To a stirred solution of 3',6'-di(azetidin-1-yl)-2-diazo-3-oxo-2,3-dihydrospiro[indene-1,9'-xanthene]-6-carboxylic acid (0.06 g, 0.12 mmol) 2-(2-((6-chlorohexyl)oxy)ethoxy)-N-methylethan-1-amine trifluoroacetate (0.088 g, 0.25 mmol) in DMF (1 mL) was added N,N'-diisopropylethylamine (0.1 mL, 0.62 mmol) at 0° C. The mixture was stirred at 0° C. for 10 min and then propanephosphonic acid anhydride (T3P) (50% in ethyl acetate; 0.22 g, 0.38 mmol) was added drop wise at 0° C. The mixture was warmed to rt and stirred at rt for 4 h. The mixture was concentrated under reduced pressure and the residue was purified by preparatory HPLC (column: X-BRIDGE-C18; mobile phase: 0-100% water in ACN) to afford 3',6'-di(azetidin-1- yl)-N-(2-(2-((6-chlorohexyl)oxy)ethoxy)ethyl)-2-diazo-N-methyl-3-oxo-2,3-dihydrospiro[indene-1,9'-xanthene]-6-carboxamide (0.02 g, 22% yield) as a pale brown solid. 1H NMR (400 MHz, DMSO-d6): δ 7.81-7.76 (m, 1H), 7.49 (d, J=8.0 Hz, 1H), 6.99-6.94 (m, 1H), 6.71 (d, J=8.4 Hz, 2H), 6.14-6.11 (m, 4H), 3.83 (t, J=7.2 Hz, 8H), 3.60-3.41 (m, 6H), 3.26-3.12 (m, 6H), 2.87 (s, 3H), 2.32-2.25 (m, 4H), 1.67-1.62 (m, 2H), 1.43-1.29 (m, 6H) ppm. m/z=698.7 [M+H]+.

9.9 Example 9

Synthesis of N-(2-(2-((6-chlorohexyl)oxy)ethoxy)ethyl)-2-diazo-3',6'-bis(3-(morpholine-4-carbonyl)azetidin-1-yl)-3-oxo-2,3-dihydrospiro[indene-1,9'-xanthene]-6-carboxamide Compound 9

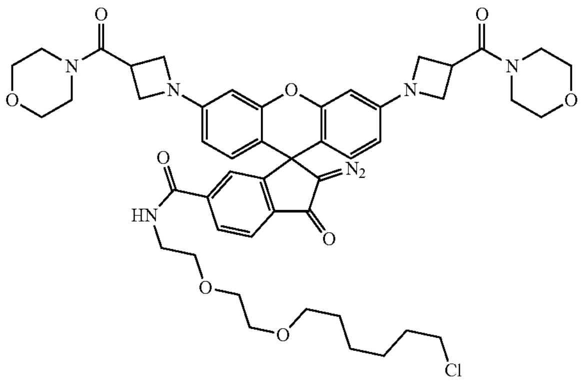

Step 1: Preparation of 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylic acid Compound 9.1

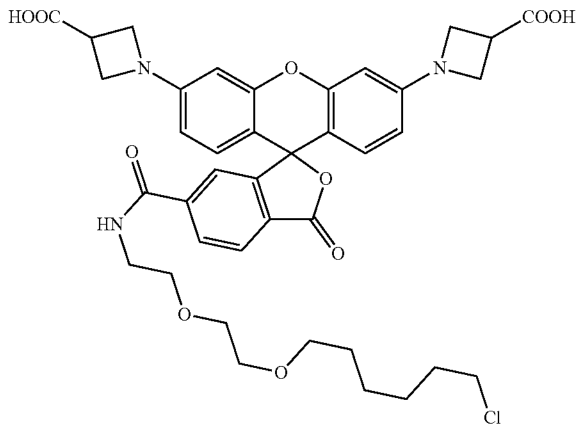

To a solution of dimethyl 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylate) (0.35 g, 0.45 mmol, Compound 1.3) in MeOH (0.35 mL) and THE (0.7 mL) at 0° C. was added a solution of lithium hydroxide monohydrate (0.021 g, 0.50 mmol) in water (0.35 mL). The mixture was stirred for 2 h at rt. The mixture was concentrated to give the desired product as a pink solid, which was used without further purification.

Step 2: Preparation of N-(2-(2-((6-chlorohexyl)oxy)ethoxy)ethyl)-3',6'-bis(3-(morpholine-4-carbonyl)azetidin-1-yl)-3-oxo-3H-spiro[isobenzofuran-1,9'-xanthene]-6-carboxamide Compound 9.2

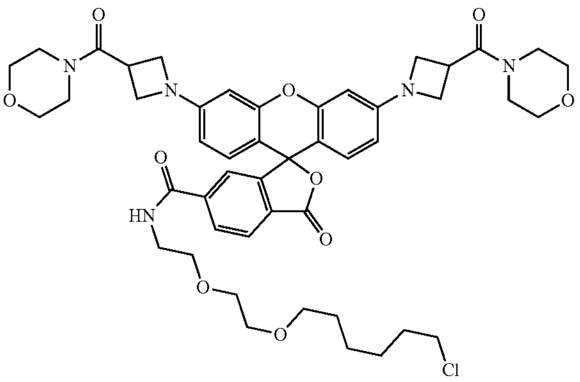

To a solution of 1,1'-(6-((2-(2-((6-chlorohexyl)oxy)ethoxy)ethyl)carbamoyl)-3-oxo-3H-spiro[isobenzofuran-1,9'-xanthene]-3',6'-diyl)bis(azetidine-3-carboxylic acid) (0.25 g, 0.33 mmol) in DMF (5 mL) at 0° C. was added N,N-diisopropylethylamine (0.6 mL, 3.3 mmol) followed by T3P (50% in ethyl acetate, 0.64 g, 1.0 mmol). The mixture was stirred at 0° C. for 1 h, then a solution of morpholine (0.145 g, 1.666 mmol) in DMF (1 mL) was added dropwise. The mixture was warmed to rt and stirred at rt for 12 h. The mixture was diluted with ice cold water (20 mL) and extracted with ethyl acetate (2×). The combined organic layers were dried over $Na_2SO_4$ and concentrated under reduced pressure. The residue was purified by preparatory HPLC (column: C18; mobile phase: 32% ACN in water) to afford the N-(2-(2-((6-chlorohexyl)oxy)ethoxy)ethyl)-3',6'-bis(3-(morpholine-4-carbonyl)azetidin-1-yl)-3-oxo-3H-spiro[isobenzofuran-1,9'-xanthene]-6-carboxamide (0.18 g, 61% yield) as a solid.

Step 3: Preparation of N-(2-(2-((6-chlorohexyl)oxy)ethoxy)ethyl)-2-diazo-3',6'-bis(3-(morpholine-4-carbonyl)azetidin-1-yl)-3-oxo-2,3-dihydrospiro[indene-1,9'-xanthene]-6-carboxamide Compound 9.3

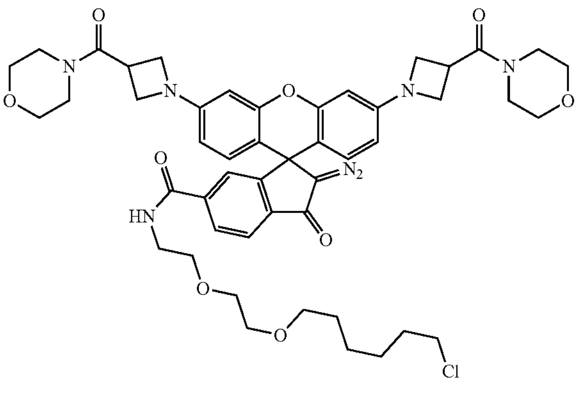

To a solution of N-(2-(2-((6-chlorohexyl)oxy)ethoxy)ethyl)-3',6'-bis(3-(morpholine-4-carbonyl)azetidin-1-yl)-3- oxo-3H-spiro[isobenzofuran-1,9'-xanthene]-6-carboxamide (0.18 g, 0.20 mmol) in DCM (3.6 mL) at 0° C. was added oxalyl chloride (1.015 mL, 2.0 mmol, 2M solution in DCM). The mixture was warmed to rt and stirred at rt for 1 h. Then the mixture was concentrated under reduced pressure. The residue was dissolved in DCM (20 mL) and added freshly prepared diazomethane in $Et_2O$ (~0.5M, 50 mmol) at 0° C. under nitrogen. The mixture was stirred at 0° C. for 30 min and then concentrated. The reside was purified by silica gel column chromatography (eluent: 85% EtOAc in petroleum ether). The residue was further purified by preparatory HPLC (column: XBridge C18; mobile phase 0-100% ACN in water) to afford N-(2-(2-((6-chlorohexyl)oxy)ethoxy)ethyl)-2-diazo-3',6'-bis(3-(morpholine-4-carbonyl)azetidin-1-yl)-3-oxo-2,3-dihydrospiro[indene-1,9'-xanthene]-6-carboxamide (0.014 g, 7.6% yield) as a solid. $^1$H NMR (400 MHz, DMSO-$d_6$): δ 8.68 (dd, J=5.6 Hz, 1H), 7.98 (d, J=1.6 Hz, 1H), 7.96 (d, J=1.6 Hz, 1H), 7.47 (s, 1H), 6.70 (d, J=8.8 Hz, 2H), 6.22 (d, J=2.0 Hz, 2H), 6.16 (dd, J=2.4 Hz, 2H), 4.04-3.82 (m, 10H), 3.38-3.33 (m, 28H), 1.65 (m, 2H), 1.42-1.22 (m, 6H) ppm. m/z=910.8[M+H]+.

9.10 Example 10

Synthesis of N-(2-(2-((6-chlorohexyl)oxy)ethoxy)ethyl)-2-diazo-3-oxo-3',6'-bis(3-(pyrrolidine-1-carbonyl)azetidin-1-yl)-2,3-dihydrospiro[indene-1,9'-xanthene]-6-carboxamide Compound 10

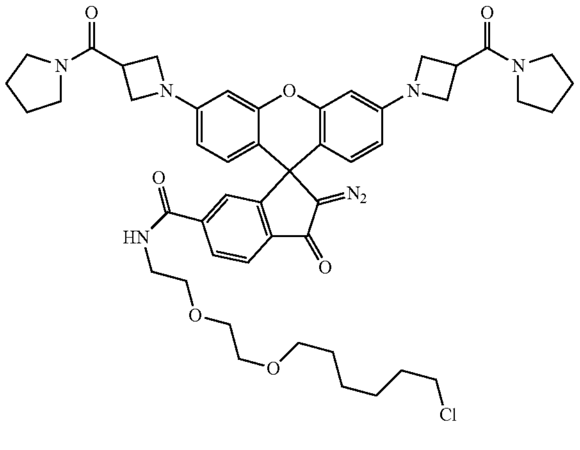

To a stirred solution of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid) (0.03 g, 0.039 mmol, Compound 2) in DMF (0.6 mL) at 0° C. and added N,N-diisopropylethylamine (0.07 mL, 0.39 mmol). Then a solution of T3P (50% in ethyl acetate, 0.058 g, 0.117 mmol) was added at 0° C. and mixture was stirred at 0° C. for 1 h. Then a solution of pyrrolidine (0.011 g, 0.16 mmol) in DMF (0.1 mL) was added. The mixture was warmed to rt and stirred at rt for 12 h. The mixture was concentrated under reduced pressure. The residue was purified by preparatory HPLC (column: Sunfire C18 Mobile phase A: 0-100% ACN in water) to afford N-(2-(2-((6-chlorohexyl)oxy)ethoxy)ethyl)-2-diazo-3-oxo-3',6'-bis(3-(pyrrolidine-1-carbonyl)azetidin-1-yl)-2,3-dihydrospiro[indene-1,9'-xanthene]-6-carboxamide (0.004 g, 11.72% yield) as a pale yellow solid. $^1$H NMR (400 MHz, DMSO-$d_6$): δ 7.95 (dd, J=1.2 Hz, 1H), 7.86 (d, J=8.0 Hz, 1H), 7.43 (s 1H), 6.70 (d, J=8.4 Hz, 1H), 6.25-6.20 (m, 4H), 4.02-3.91 (m, 4H), 3.89-3.85 (m, 4H), 3.75-3.73 (m, 2H), 3.57-3.54 (m, 2H), 3.48-3.19 (m, 20H), 1.89-1.86 (m, 4H), 1.80-1.77 (m, 4H), 1.62-1.61 (m, 2H), 1.38-1.18 (m, 6H) ppm. m/z=878.9 [M+H]+.

9.11 Example 11

Synthesis of N-(2-(2-((6-chlorohexyl)oxy)ethoxy)ethyl)-2-diazo-3',6'-bis(3-(4-methylpiperazine-1-carbonyl)azetidin-1-yl)-3-oxo-2,3-dihydrospiro[indene-1,9'-xanthene]-6-carboxamide Compound 11

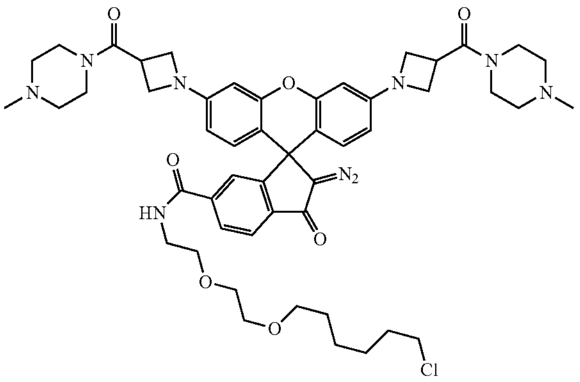

To a solution of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid) (0.045 g, 0.058 mmol, Compound 2) in DMF (0.9 mL) at 0° C. was added N,N-diisopropylethylamine (0.065 mL, 0.35 mmol) followed by T3P (50% in ethyl acetate 0.074 g, 0.117 mmol). The mixture was stirred at 0° C. for 1 h. Then a solution of N-methylpiperazine (0.015 g, 0.146 mmol) in DMF (0.1 mL) was added drop wise. The mixture was warmed to rt and stirred at rt for 12 h. The mixture was concentrated under reduced pressure. The residue was purified by preparatory HPLC (column: X-SELECT C18; mobile phase: 0-100% acetonitrile with 10 mM ammonium acetate in water) to afford N-(2-(2-((6-chlorohexyl)oxy)ethoxy)ethyl)-2-diazo-3',6'-bis(3-(4-methylpiperazine-1-carbonyl)azetidin-1-yl)-3-oxo-2,3-dihydrospiro[indene-1,9'-xanthene]-6-carboxamide (5.2 mg, 9.5% yield) as a solid. $^1$H NMR (400 MHz, DMSO-$d_6$): δ 8.69 (t, 1H), 7.97 (d, J=8.0 Hz, 1H), 7.83 (d, J=8.0 Hz, 1H), 7.47 (s, 1H), 6.69 (d, J=8.4 Hz, 2H), 6.22 (d, J=2 Hz, 2H), 6.16 (d, J=6.8 Hz, 2H), 4.06-4.01 (m, 4H), 3.92-3.79 (m, 6H), 3.42-3.29 (m, 20H), 2.35-2.20 (m, 8H), 2.17 (s, 6H), 1.69-1.63 (m, 2H), 1.42-1.20 (m, 6H) ppm. m/z=936.7 [M+H]+.

9.12 Example 12

Synthesis of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N-methylazetidine-3-carboxamide Compound 12

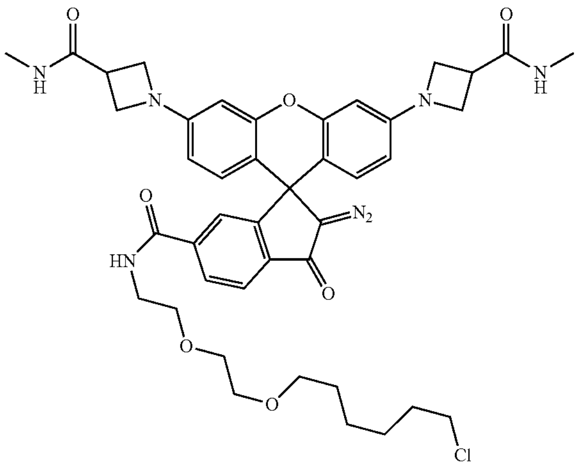

The title compound was prepared using similar procedure as Example 11, replacing N-methylpiperazine with methylamine (2 M in THF). The residue was purified by preparatory HPLC (column: X SELECT-C18; mobile phase: 0-100% ACN in water) to afford the title compound. $^1$H NMR (400 MHz, DMSO-$d_6$): δ 8.70 (t, J=5.2 Hz, 1H), 7.98-7.92 (m, 3H), 7.83 (d, J=8.0 Hz, 1H), 7.48 (s 1H), 6.68 (d, J=8.4 Hz, 2H), 6.21 (d, J=8.4 Hz, 2H), 6.14 (dd, J=2.0 Hz and 2.4 Hz, 2H), 3.97-3.95 (m, 4H), 3.85-3.80 (m, 4H), 3.58 (t, J=6.4 Hz, 2H), 3.47-3.28 (m, 12H), 2.60-2.49 (m, 6H), 1.67-1.63 (m, 2H), 1.42-1.23 (m, 6H) ppm. m/z=798.8 [M+H]+.

9.13 Example 13

Synthesis of N-(2-(2-((6-chlorohexyl)oxy)ethoxy)ethyl)-2-diazo-3',6'-bis(3-(dimethylamino)azetidin-1-yl)-3-oxo-2,3-dihydrospiro[indene-1,9'-xanthene]-6-carboxamide Compound 13

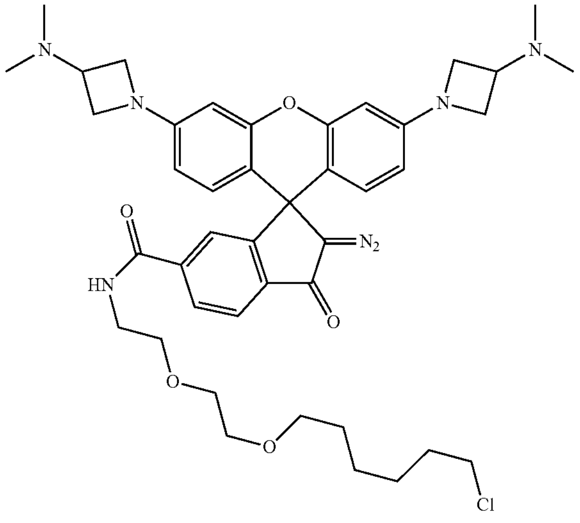

The title compound was prepare using a similar procedures as Example 7, replacing methyl 3',6'-dibromo-3-oxo-3H-spiro[isobenzofuran-1,9'-xanthene]-6-carboxylate, Intermediate B, and azetidin-3-ol-hydrochloride with 3',6'-dibromo-N-(2-(2-((6-chlorohexyl)oxy)ethoxy)ethyl)-3-oxo-3H-spiro[isobenzofuran-1,9'-xanthene]-6-carboxamide, Intermediate D' and N,N-dimethylazetidin-3-amine hydrochloride in Step 1. The residue was purified by silica gel column chromatography (eluent: 50-100% ethyl acetate in petroleum ether). The residue was further purified by SFC to afford N-(2-(2-((6-chlorohexyl)oxy)ethoxy)ethyl)-2-diazo-3',6'-bis(3-(dimethylamino)azetidin-1-yl)-3-oxo-2,3-dihydrospiro[indene-1,9'-xanthene]-6-carboxamide as a pale-yellow solid. $^1$H NMR (400 MHz, DMSO-$d_6$): δ 8.68 (br s, 1H), 7.96 (d, J=8.4 Hz, 1H), 7.98 (d, J=8.0 Hz, 1H), 7.48 (d, J=8.0 Hz, 1H) 6.69 (d, J=8.8 Hz, 2H), 6.19 (d, J=2.4 Hz, 2H), 6.15 (d, J=8.8 Hz, 2H), 3.90-3.87 (m, 4H), 3.61-3.57 (m, 6H), 3.47-3.39 (m, 10H), 3.18-3.15 (m, 2H), 2.09 (s, 12H), 1.67-1.62 (m, 2H), 1.42-1.39 (m, 2H), 1.32-1.30 (m, 2H), 1.26-1.23 (m, 2H) ppm. m/z=770.7[M+H]+.

9.14 Example 14

Synthesis of (2S,2'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylazetidine-2-carboxamide Compound 14

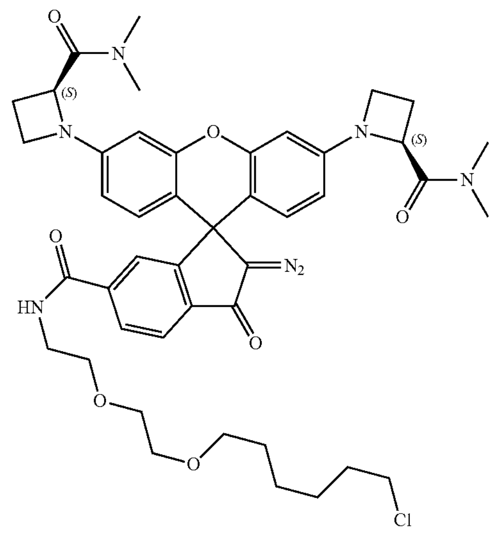

The title compound was prepared using a similar procedures as Example 7, replacing methyl 3',6'-dibromo-3-oxo-3H-spiro[isobenzofuran-1,9'-xanthene]-6-carboxylate, Intermediate B, and azetidin-3-ol-hydrochloride with 3',6'-dibromo-N-(2-(2-((6-chlorohexyl)oxy)ethoxy)ethyl)-3-oxo-3H-spiro[isobenzofuran-1,9'-xanthene]-6-carboxamide, Intermediate D' and (S)—N,N-dimethylazetidine-2-carboxamide hydrochloride in Step 1. The residue was purified by silica gel column chromatography (eluent: 90% ethyl acetate in petroleum ether). The residue was further purified by preparatory HPLC (column: X-BRIDGE C18; mobile phase: 0-100% ACN in water) to afford 2S,2'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis (N,N-dimethylazetidine-2-carboxamide) as an off-white solid. $^1$H NMR (400 MHz, DMSO-$d_6$): δ 8.70 (s, 1H), 7.98-795 (m, 1H), 7.85 (d, J=8.0 Hz, 1H), 7.48-7.41 (m, 1H), 6.67 (dd, J=3.2 Hz & 8.8 Hz, 2H), 6.14-6.10 (m, 4H), 4.81 (d, J=8.0 Hz, 2H), 3.81-3.29 (m, 16H), 2.91-2.87 (m, 12H), 2.63-2.58 (m, 2H), 2.31-2.26 (m, 2H), 1.68-1.65 (m, 2H), 1.44-1.40 (m, 2H), 1.35-1.31 (m, 2H), 1.26-1.23 (m, 2H) ppm. m/z=826.3 [M+H]+.

9.15 Example 15

Synthesis of N-(2-(2-((6-chlorohexyl)oxy)ethoxy)ethyl)-2-diazo-3',6'-bis((R)-2-(hydroxymethyl)azetidin-1-yl)-3-oxo-2,3-dihydrospiro[indene-1,9'-xanthene]-6-carboxamide Compound 15

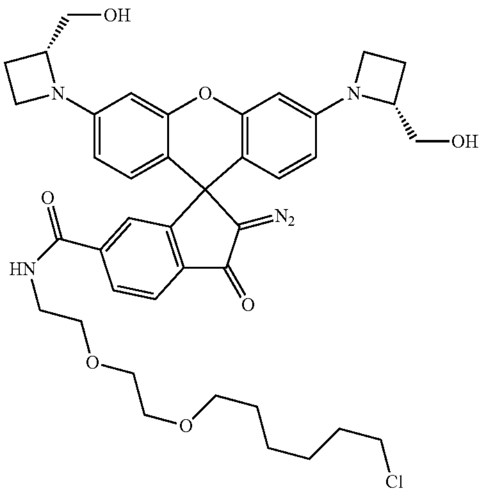

The title compound was prepared using a similar procedures as Example 7, replacing methyl 3',6'-dibromo-3-oxo-3H-spiro[isobenzofuran-1,9'-xanthene]-6-carboxylate, Intermediate B, and azetidin-3-ol-hydrochloride with 3',6'-dibromo-N-(2-(2-((6-chlorohexyl)oxy)ethoxy)ethyl)-3-oxo-3H-spiro[isobenzofuran-1,9'-xanthene]-6-carboxamide, Intermediate D' and (R)-azetidin-2-ylmethanol hydrochloride. The residue was purified by silica gel column chromatography (eluent: 90% ethyl acetate in petroleum ether). The residue was further purified by preparatory HPLC (column: X-BRIDGE C18; mobile phase: 0-100% ACN in water) to afford N-(2-(2-((6-chlorohexyl)oxy)ethoxy)ethyl)-2-diazo-3',6'-bis((R)-2-(hydroxymethyl)azetidin-1-yl)-3-oxo-2,3-dihydrospiro[indene-1,9'-xanthene]-6-carboxamide as a pale-yellow solid. $^1$H NMR (400 MHz, DMSO-$d_6$): δ 8.69 (s, 1H), 7.96 (d, J=8.0 Hz, 1H), 7.83 (d, J=8.0 Hz, 1H), 7.45 (s, 1H), 6.66 (d, J=8.4 Hz, 2H), 6.45 (d, J=6.0 Hz, 2H), 6.28-6.24 (m, 2H), 4.96 (d, J=3.2 Hz, 2H), 4.0-4.02 (m, 2H), 3.88-3.80 (m, 2H), 3.60-3.45 (m, 18H), 2.10-2.08 (m, 2H), 2.10-2.07 (m, 2H), 1.67-1.64 (m, 2H), 1.43-1.39 (m, 2H), 1.38-1.20 (m, 4H) ppm. m/z=744.8 [M+H]+.

9.16 Example 16

Synthesis of (3S,3'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylpyrrolidine-3-carboxamide Compound 16

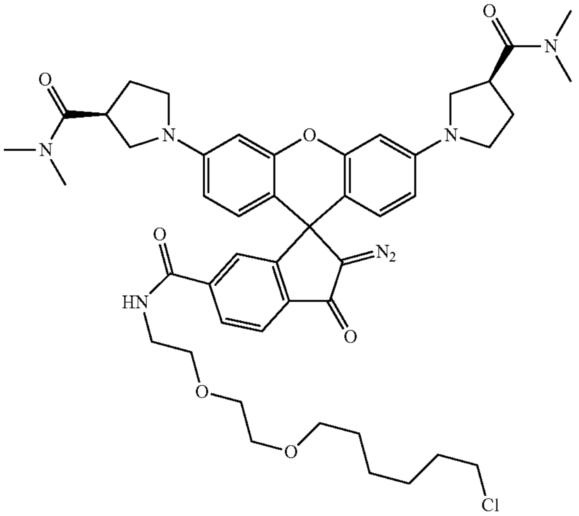

The title compound was prepared using a similar procedures as Example 7, replacing methyl 3',6'-dibromo-3-oxo-3H-spiro[isobenzofuran-1,9'-xanthene]-6-carboxylate, Intermediate B, and azetidin-3-ol-hydrochloride with 3',6'-dibromo-N-(2-(2-((6-chlorohexyl)oxy)ethoxy)ethyl)-3-oxo-3H-spiro[isobenzofuran-1,9'-xanthene]-6-carboxamide, Intermediate D' and (S)—N,N-dimethylpyrrolidine-3-carboxamide. The residue was purified by silica gel column chromatography (eluent: 50-100% ethyl acetate in petroleum ether). The residue was further purified by preparatory HPLC (column: X-BRIDGE C18; mobile phase: 0-100% ACN in water) to afford (3S,3'S)-1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(N,N-dimethylpyrrolidine-3-carboxamide) as a solid. $^1$H NMR (400 MHz, DMSO-$d_6$): δ 8.67 (t, J=5.6 Hz, 1H), 7.96 (d, J=8.0 Hz, 1H), 7.83 (d, J=8.0 Hz, 1H), 7.46 (s, 1H), 6.67 (d, J=8.0 Hz 2H), 6.29-6.26 (m, 4H), 3.57 (t, J=6.8 Hz, 2H), 3.51-3.39 (m, 10H), 3.31-3.25 (m, 10H), 3.06 (s, 6H), 2.84 (s, 6H), 2.17-2.16 (m, 2H), 2.07-2.05 (m, 2H), 1.67-1.63 (m, 2H), 1.42-1.22 (m, 6H) ppm. m/z=854.9[M+H]+.

9.17 Example 17

Synthesis of 3',6'-di(3-oxa-6-azabicyclo[3.1.1]heptan-6-yl)-N-(2-(2-((6-chlorohexyl)oxy)ethoxy)ethyl)-2-diazo-3-oxo-2,3-dihydrospiro[indene-1,9'-xanthene]-6-carboxamide Compound 17

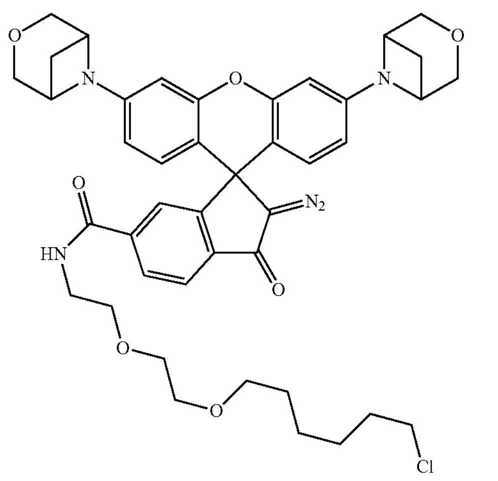

Step 1: Preparation of methyl 3',6'-di(3-oxa-6-azabicyclo[3.1.1]heptan-6-yl)-3-oxo-3H-spiro[isobenzofuran-1,9'-xanthene]-6-carboxylate Compound 17.1

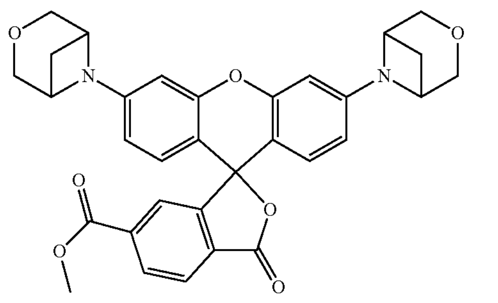

To a stirred solution of methyl 3',6'-dibromo-3-oxo-3H-spiro[isobenzofuran-1,9'-xanthene]-6-carboxylate (Intermediate-B) (0.5 g, 0.969 mmol) and 3-oxa-6-azabicyclo[3.1.1]heptane 4-methylbenzene-1-sulfonate (0.657 g, 2.422 mmol) in 1,4-dioxane (10 mL) in a dried sealed tube was added cesium carbonate (1.578 g, 4.844 mmol) at rt and the reaction mixture was purged with argon gas for 20 min. Then XPhos-Pd-G4 (0.083 g, 0.097 mmol) was added at rt. The reaction mixture was again purged with argon gas for 10 min. and stirred at 100° C. for 12 h. The reaction was monitored by TLC and LCMS. After completion of reaction, the mixture was filtered through Celite and washed with ethyl acetate. The filtrate was diluted with water (30 mL), extracted with ethyl acetate (30 mL×2), and the combined organic layers were dried over anhydrous sodium sulfate and concentrated under reduced pressure. The crude was purified by flash chromatography using silica gel in 0-100% ethyl acetate in pet ether, the desired product was eluted in 90-95% ethyl acetate in pet ether to afford methyl 3',6'-di(3-oxa-6-azabicyclo[3.1.1]heptan-6-yl)-3-oxo-3H-spiro[isobenzofuran-1,9'-xanthene]-6-carboxylate (0.35 g, 65% yield) as a pink solid. m/z 553.51 ($M+H^+$). Step 2: Preparation of 3',6'-di(3-oxa-6-azabicyclo[3.1.1]heptan-6-yl)-3-oxo-3H-spiro[isobenzofuran-1,9'-xanthene]-6-carboxylic acid Compound 17.2

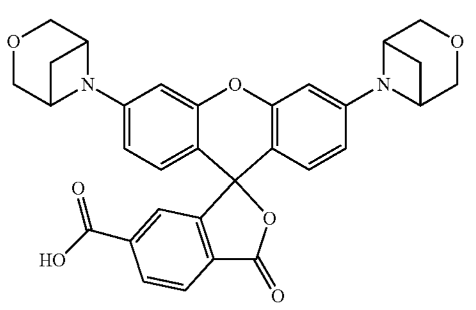

To a stirred solution of methyl 3',6'-di(3-oxa-6-azabicyclo[3.1.1]heptan-6-yl)-3-oxo-3H-spiro[isobenzofuran-1,9'-xanthene]-6-carboxylate (Compound 17.1) (0.35 g, 0.633 mmol) in THF (8.0 mL) and $MeOH:H_2O$ (1:1) (8.0 mL) was added lithium hydroxide monohydrate (0.053 g, 1.266 mmol) portion wise at 0° C. The reaction mixture was stirred for 12 h at rt. The reaction was monitored by TLC and LCMS. After completion of reaction, the mixture was concentrated under reduced pressure and diluted with water (2 mL), then acidified by using 1N HCl (pH~2). The precipitate formed was filtered and dried under high vacuum. The dried solids were washed with diethyl ether to afford 3',6'-di(3-oxa-6-azabicyclo[3.1.1]heptan-6-yl)-3-oxo-3H-spiro[isobenzofuran-1,9'-xanthene]-6-carboxylic acid (0.25 g, 70% yield) as a pink solid. m/z 539.36 [M+H]+.

Step 3: Preparation of 3',6'-di(3-oxa-6-azabicyclo[3.1.1]heptan-6-yl)-N-(2-(2-((6-chlorohexyl)oxy)ethoxy)ethyl)-3-oxo-3H-spiro[isobenzofuran-1,9'-xanthene]-6-carboxamide Compound 17.3

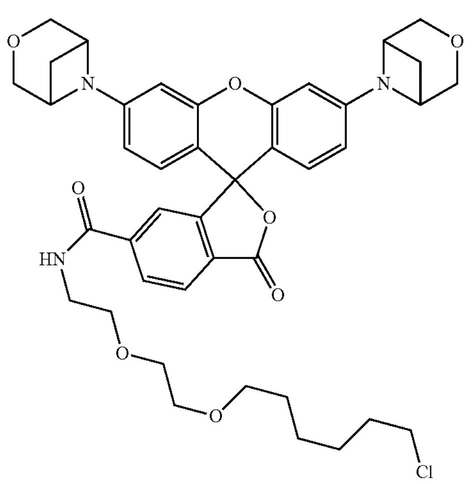

To a stirred solution of 3',6'-di(3-oxa-6-azabicyclo[3.1.1]heptan-6-yl)-3-oxo-3H-spiro[isobenzofuran-1,9'-xanthene]-6-carboxylic acid (Compound 17.2) (0.250 g, 0.464 mmol) and 2-(2-((6-chlorohexyl)oxy)ethoxy)ethan-1-amine (0.259 g, 1.160 mmol) in DMF (5 mL) was added N,N'-diisopropylethylamine (0.4 mL, 2.321 mmol) at 0° C. After 10 min, propanephosphonic acid anhydride (T3P) (50% in ethyl acetate; 0.886 g, 1.392 mmol) was added drop wise at 0° C. The reaction mixture was stirred for 12 h at rt. The reaction was monitored by TLC and LCMS. After completion of reaction, the reaction mixture was directly evaporated to remove DMF solvent and then it was purified by reverse phase column purification using C18 column, in 0-100% acetonitrile in water, the desired product was eluted in 22% acetonitrile in water to afford 3',6'-di(3-oxa-6-azabicyclo[3.1.1]heptan-6-yl)-N-(2-(2-((6-chlorohexyl)oxy)ethoxy)ethyl)-3-oxo-3H-spiro[isobenzofuran-1,9'-xanthene]-6-carboxamide (0.097 g, 28% yield) as pink solid.

Step 4: Preparation of 3',6'-di(3-oxa-6-azabicyclo[3.1.1]heptan-6-yl)-N-(2-(2-((6-chlorohexyl)oxy)ethoxy)ethyl)-2-diazo-3-oxo-2,3-dihydrospiro[indene-1,9'-xanthene]-6-carboxamide Compound 17.4

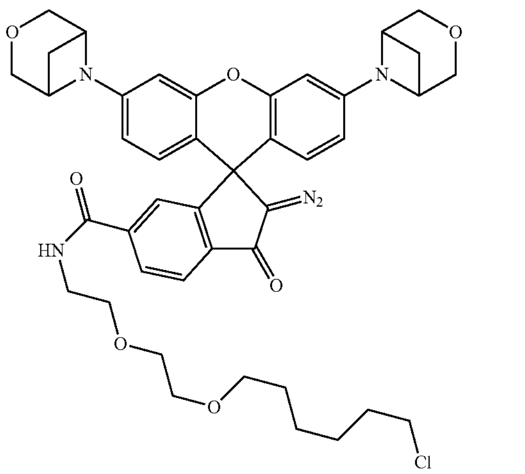

Method A. To a solution of 3',6'-di(3-oxa-6-azabicyclo[3.1.1]heptan-6-yl)-N-(2-(2-((6-chlorohexyl)oxy)ethoxy)ethyl)-3-oxo-3H-spiro[isobenzofuran-1,9'-xanthene]-6-carboxamide (compound 17.3) (29 mg, 0.039 mmol) in dry $CH_2Cl_2$ (1 mL), was added 4 Å powdered molecular sieves (15 mg) under argon. 1-Chloro-N,N,2-trimethylprop-1-en-1-amine (20.6 μL, 0.156 mmol) was then added via syringe and the mixture was stirred at rt for 45 min. N,N-Diisopropylethylamine (27 μL, 0.156 mmol) was added, followed by $TMSCHN_2$ (2M in hexanes, 78 μL, 0.156 mmol). After stirring for 2.5 hours at rt, the mixture was filtered and concentrated. The residue was purified by reverse phase flash chromatography (0-100% ACN in water). The residue was purified a second time via reverse phase flash chromatography (30-100% ACN in water). A third purification was performed using a pipette column packed with basic alumina and eluted with 50-100% EtOAc in toluene. The fractions containing product were concentrated, redissolved in dioxane and dried on the lyophilizer to yield a solid (1.7 mg, 6%). $^1$H NMR (400 MHz, Pyr) δ 9.39 (t, J=5.7 Hz, 1H), 8.40 (d, J=8.0 Hz, 1H), 8.32 (s, 1H), 8.13 (d, J=8.0 Hz, 1H), 7.02 (d, J=8.5 Hz, 2H), 6.52 (d, J=2.2 Hz, 2H), 6.35 (dd, J=8.5, 2.2 Hz, 2H), 4.37 (dd, J=22.3, 10.6 Hz, 4H), 4.19 (d, J=6.0 Hz, 4H), 3.70-3.60 (m, 8H), 3.55-3.47 (m, 6H), 3.35 (t, J=6.5 Hz, 2H), 2.65-2.60 (m, 2H), 1.82 (d, J=8.0 Hz, 2H), 1.65-1.58 (m, 2H), 1.51-1.45 (m, 2H), 1.35-1.19 (m, 4H). m/z=768.2 [M+H$^+$].

Method B. To a solution of 3',6'-di(3-oxa-6-azabicyclo[3.1.1]heptan-6-yl)-N-(2-(2-((6-chlorohexyl)oxy)ethoxy)ethyl)-3-oxo-3H-spiro[isobenzofuran-1,9'-xanthene]-6-carboxamide (compound 17.3) (29 mg, 0.039 mmol) in dry $CH_2Cl_2$ (1 mL), was added 4 Å powdered molecular sieves (15 mg) under argon. 1-Chloro-N,N,2-trimethylprop-1-en-1-amine (20.6 μL, 0.156 mmol) was then added via syringe and the mixture was stirred at rt for 45 min. N,N-Diisopropylethylamine (27 μL, 0.156 mmol) was added, followed by $TMSCHN_2$ (2M in hexanes, 78 μL, 0.156 mmol). After stirring for 2.5 hours at rt, the mixture was filtered and concentrated. The residue was purified by reverse phase flash chromatography (0-100% ACN in water). The residue was further purified by reverse phase flash chromatography (30-100% ACN in water). The residue was further purified by flash chromatography using basic alumina (eluent: 50-100% EtOAc in toluene) to afford the title compound as a solid (1.7 mg, 6%). $^1$H NMR (400 MHz, pyridine-d5) δ 9.39 (t, J=5.7 Hz, 1H), 8.40 (d, J=8.0 Hz, 1H), 8.32 (s, 1H), 8.13 (d, J=8.0 Hz, 1H), 7.02 (d, J=8.5 Hz, 2H), 6.52 (d, J=2.2 Hz, 2H), 6.35 (dd, J=8.5, 2.2 Hz, 2H), 4.37 (dd, J=22.3, 10.6 Hz, 4H), 4.19 (d, J=6.0 Hz, 4H), 3.70-3.60 (m, 8H), 3.55-3.47 (m, 6H), 3.35 (t, J=6.5 Hz, 2H), 2.65-2.60 (m, 2H), 1.82 (d, J=8.0 Hz, 2H), 1.65-1.58 (m, 2H), 1.51-1.45 (m, 2H), 1.35-1.19 (m, 4H). m/z=768.2 [M+H]+.

9.18 Example 18

Synthesis of N-(2-(2-((6-chlorohexyl)oxy)ethoxy)ethyl)-2-diazo-3',6'-bis(3-methyl-3,6-diazabicyclo[3.1.1]heptan-6-yl)-3-oxo-2,3-dihydrospiro[indene-1,9'-xanthene]-6-carboxamide Compound 18

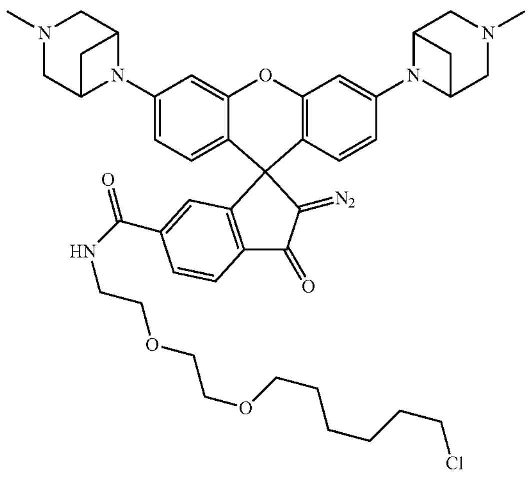

Step 1: Preparation of methyl 3',6'-bis(3-methyl-3,6-diazabicyclo[3.1.1]heptan-6-yl)-3-oxo-3H-spiro[isobenzofuran-1,9'-xanthene]-6-carboxylate Compound 18.1

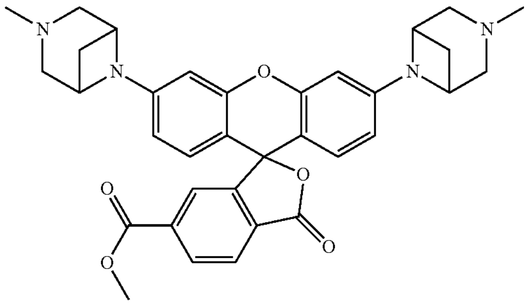

To a stirred solution of methyl 3',6'-dibromo-3-oxo-3H-spiro[isobenzofuran-1,9'-xanthene]-6-carboxylate (Intermediate-B) (0.5 g, 0.969 mmol) and 3-methyl-3,6-diazabicyclo[3.1.1]heptane dihydrochloride (0.447 g, 2.422 mmol) in 1,4-dioxane (10 mL) in a dried sealed tube was added $Cs_2CO_3$ (3.156 g, 9.687 mmol) at rt and the mixture was purged with argon gas for 20 min. Then $Pd_2(dba)_3$ (0.089 g, 0.097 mmol) and RuPhos (0.135 g, 0.291 mmol) were added at rt. The mixture was again purged with argon gas for 10 min. and stirred at 110° C. for 16 h. The reaction was monitored by TLC and LCMS. After completion of the reaction, the mixture was filtered through Celite, washed with methanol (100 mL) and concentrated. The residue was purified by silica gel chromatography eluting with (1% MeOH in DCM to 5% ammonia in DCM) to afford methyl 3',6'-bis(3-methyl-3,6-diazabicyclo[3.1.1]heptan-6-yl)-3-oxo-3H-spiro[isobenzofuran-1,9'-xanthene]-6-carboxylate (0.20 g, 35.68% yield)) as a pink solid. m/z 579.58 [M+H]+.

Step 2: Preparation of 3',6'-bis(3-methyl-3,6-diazabicyclo[3.1.1]heptan-6-yl)-3-oxo-3H-spiro[isobenzofuran-1,9'-xanthene]-6-carboxylic acid Compound 18.2

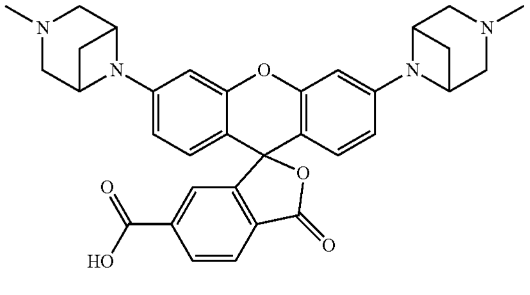

To a stirred solution of methyl 3',6'-bis(3-methyl-3,6-diazabicyclo[3.1.1]heptan-6-yl)-3-oxo-3H-spiro[isobenzofuran-1,9'-xanthene]-6-carboxylate (Compound 18.1) (0.2 g, 0.346 mmol) in THF (2.0 mL) and MeOH:$H_2O$ (1:1) (2.0 mL) was added lithium hydroxide monohydrate (0.072 g, 1.728 mmol) portion wise at 0° C. The mixture was stirred for 12 h at rt. The reaction was monitored by TLC and LCMS. After completion of the reaction, the organic solvent was removed under reduced pressure and the remaining crude material was diluted with water (2 mL), and the mixture was acidified using conc. HCl to pH ~2. The solid precipitated, and then was filtered and dried under vacuum. The residue was purified by C18 reverse phase column chromatography (eluent: ACN in water (0.05% formic acid)) to afford 3',6'-bis(3-methyl-3,6-diazabicyclo[3.1.1]heptan-6-yl)-3-oxo-3H-spiro[isobenzofuran-1,9'-xanthene]-6-carboxylic acid (0.14 g, 72% yield) as a pink solid. m/z 565.43 ($M+H^+$).

Step 3: Preparation of N-(2-(2-((6-chlorohexyl)oxy)ethoxy)ethyl)-3',6'-bis(3-methyl-3,6-diazabicyclo[3.1.1]heptan-6-yl)-3-oxo-3H-spiro[isobenzofuran-1,9'-xanthene]-6-carboxamide Compound 18.3

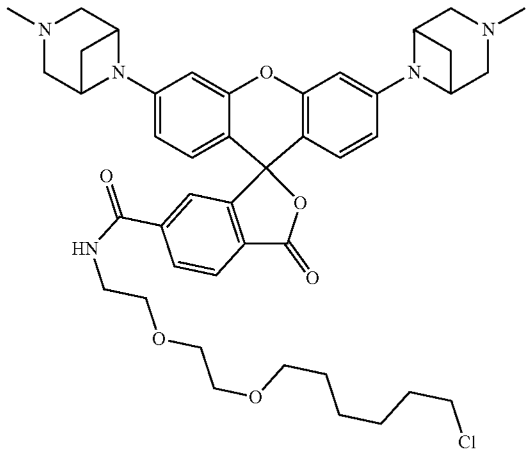

To a stirred solution of 3',6'-bis(3-methyl-3,6-diazabicyclo[3.1.1]heptan-6-yl)-3-oxo-3H-spiro[isobenzofuran-1,9'-xanthene]-6-carboxylic acid (Compound 18.2) (0.14 g, 0.248 mmol) and 2-(2-((6-chlorohexyl)oxy)ethoxy)ethan-1-amine (0.139 g, 0.620 mmol) in DMF (2 mL) was added N,N'-diisopropylethylamine (0.216 mL, 1.240 mmol) at 0° C. After 10 min, propanephosphonic acid anhydride (T3P) (50% in ethyl acetate; 0.237 g, 0.744 mmol) was added drop wise at 0° C. The reaction mixture was stirred for 16 h at rt. The reaction was monitored by TLC and LCMS. After completion of reaction, the reaction mixture was directly evaporated to remove DMF solvent and then it was purified by reverse phase column purification using C18 column in 0-100% acetonitrile in water, the desired product was eluted in 15% acetonitrile in water to afford N-(2-(2-((6-chlorohexyl)oxy)ethoxy)ethyl)-3',6'-bis(3-methyl-3,6-diazabicyclo[3.1.1]heptan-6-yl)-3-oxo-3H-spiro[isobenzofuran-1,9'-xanthene]-6-carboxamide (0.110 g, 56% yield) as a pink solid.

Compound 18.4

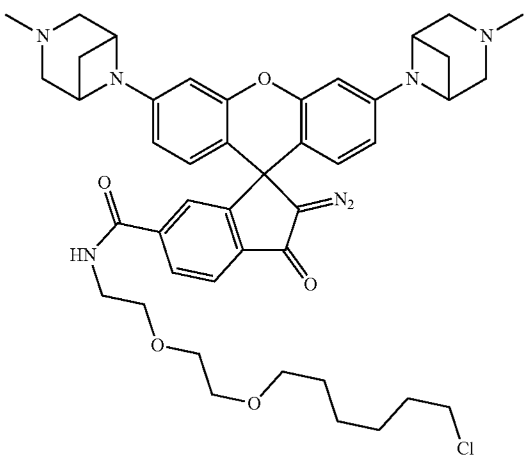

Method A. To a solution of N-(2-(2-((6-chlorohexyl)oxy) ethoxy)ethyl)-3',6'-bis(3-methyl-3,6-diazabicyclo[3.1.1] heptan-6-yl)-3-oxo-3H-spiro[isobenzofuran-1,9'-xanthene]-6-carboxamide (Compound 18.3) (10 mg, 0.013 mmol) in dry $CH_2Cl_2$ (350 μL), was added 4 Å powdered molecular sieves (5 mg) under argon. 1-Chloro-N,N,2-trimethylprop-1-en-1-amine (6.9 μL, 0.052 mmol) was then added via syringe and the mixture was stirred at rt for 45 min. N,N-Diisopropylethyl amine (9 μL, 0.052 mmol) was added, followed by $TMSCHN_2$ (2M in hexanes, 26 μL, 0.052 mmol). After stirring for 2.5 hours at rt, the mixture was filtered and concentrated. The residue was purified by reverse phase flash chromatography (10-100% ACN in water). The residue was purified a second time using a pipette column packed with basic alumina and eluted with 10% MeOH in $CH_2Cl_2$. The fractions containing product were concentrated, redissolved in dioxane and dried on the lyophilizer to yield a solid (1.4 mg, 13%). $^1$H NMR (400 MHz, Pyr) δ 9.42 (t, J=5.6 Hz, 1H), 8.35 (dd, J=8.0, 1.5 Hz, 1H), 8.25 (d, J=1.5 Hz, 1H), 8.10 (d, J=8.0 Hz, 1H), 6.98 (d, J=8.5 Hz, 2H), 6.47 (d, J=2.2 Hz, 2H), 6.27 (dd, J=8.5, 2.2 Hz, 2H), 4.28-4.11 (m, 4H), 3.75-3.67 (m, 4H), 3.61-3.44 (m, 6H), 3.35 (t, J=6.5 Hz, 2H), 3.05 (t, J=11.7 Hz, 4H), 2.71-2.64 (m, 4H), 2.43 (q, J=6.3 Hz, 2H), 2.04 (s, 6H), 2.02 (d, J=7.4 Hz, 2H), 1.65-1.57 (m, 2H), 1.51-1.45 (m, 2H), 1.45-1.14 (m, 4H). m/z=794.2 $[M+H^+]$.

Method B. To a solution of N-(2-(2-((6-chlorohexyl)oxy) ethoxy)ethyl)-3',6'-bis(3-methyl-3,6-diazabicyclo[3.1.1] heptan-6-yl)-3-oxo-3H-spiro[isobenzofuran-1,9'-xanthene]-6-carboxamide (Compound 18.3) (10 mg, 0.013 mmol) in dry $CH_2Cl_2$ (350 μL), was added 4 Å powdered molecular sieves (5 mg) under argon. 1-Chloro-N,N,2-trimethylprop-1-en-1-amine (6.9 μL, 0.052 mmol) was then added via syringe and the mixture was stirred at rt for 45 min. N,N-Diisopropylethylamine (9 μL, 0.052 mmol) was added, followed by $TMSCHN_2$ (2M in hexanes, 26 μL, 0.052 mmol). After stirring for 2.5 hours at rt, the mixture was filtered and concentrated. The residue was purified by reverse phase flash chromatography (10-100% ACN in water). The residue was further purified by flash chromatography using basic alumina (eluent: 10% MeOH in $CH_2Cl_2$) to afford the title compounds as a solid (1.4 mg, 13%). $^1$H NMR (400 MHz, pyridine-d5) δ 9.42 (t, J=5.6 Hz, 1H), 8.35 (dd, J=8.0, 1.5 Hz, 1H), 8.25 (d, J=1.5 Hz, 1H), 8.10 (d, J=8.0 Hz, 1H), 6.98 (d, J=8.5 Hz, 2H), 6.47 (d, J=2.2 Hz, 2H), 6.27 (dd, J=8.5, 2.2 Hz, 2H), 4.28-4.11 (m, 4H), 3.75-3.67 (m, 4H), 3.61-3.44 (m, 6H), 3.35 (t, J=6.5 Hz, 2H), 3.05 (t, J=11.7 Hz, 4H), 2.71-2.64 (m, 4H), 2.43 (q, J=6.3 Hz, 2H), 2.04 (s, 6H), 2.02 (d, J=7.4 Hz, 2H), 1.65-1.57 (m, 2H), 1.51-1.45 (m, 2H), 1.45-1.14 (m, 4H). m/z=794.2 [M+H]+.

9.19 Example 19

Synthesis of 1,1'-(6'-((2-(2-((6-chlorohexyl)oxy) ethoxy)ethyl)carbamoyl)-5,5-dimethyl-3'-oxo-3'H, 5H-spiro[dibenzo[b,e]siline-10,1'-isobenzofuran]-3, 7-diyl)bis(N,N-dimethylazetidine-3-carboxamide Compound 19

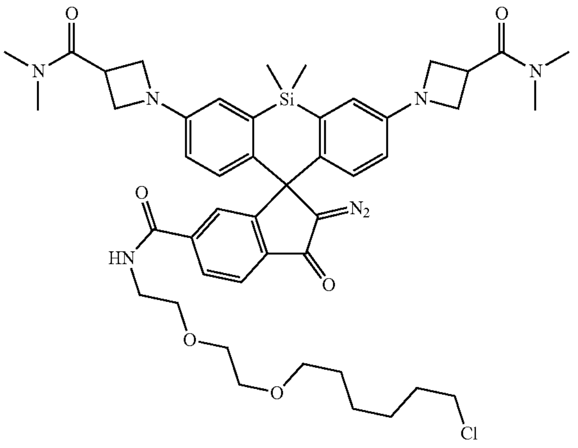

Step 1: Preparation of tert-butyl 5,5-dimethyl-3'-oxo-3,7-bis((triisopropylsilyl)oxy)-3'H,5H-spiro [dibenzo[b,e]siline-10,1'-isobenzofuran]-6'-carboxylate Compound 19.1

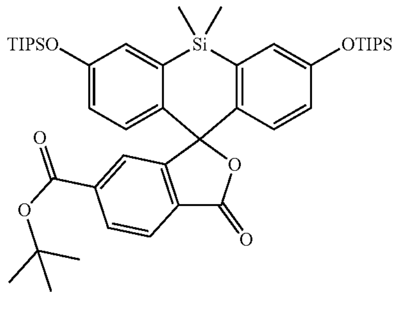

A solution of 1,4-di-tert-butyl 2-bromobenzene-1,4-dicarboxylate (1.53 g, 4.29 mmol, WO2018046753A1) in 2:1 anhydrous THF/pentane (15 ml) was cooled to −100° C. in a diethyl ether/liquid nitrogen bath. The solution was sparged with Ar (g) for 10 min before n-BuLi (2.5M in hexanes, 1.75 mL, 1.72 mmol) was added dropwise along the wall of the flask. The solution was allowed to stir at −100° C. for 10 minutes during which the solution became purple and then brown. A solution of 5,5-Dimethyl-3,7-bis ((triisopropylsilyl)oxy)dibenzo[b,e]silin-10(5H)-one (1.0 g, 1.72 mmol, WO2018046753A1) in THF (5 mL) was added dropwise along the wall of the flask and allowed to stir at −78° C. in a dry ice/acetone bath for 10 minutes. The mixture was then allowed to warm to room temperature, stirring for 2.5 hours. The mixture was adsorbed onto celite and purified by flash chromatography using a silica gel column (25-50% $CH_2Cl_2$ in hexanes) to afford the title compound as a crystalline solid (436 mg, 32%). $^1$H NMR (400 MHz, $CDCl_3$) δ 7.92 (dd, J=8.0, 1.3 Hz, 1H), 7.78 (d, J=8.0 Hz, 1H), 7.63 (s, 1H), 6.98 (d, J=2.7 Hz, 2H), 6.74 (d, J=8.7 Hz, 2H), 6.56 (dd, J=8.7, 2.7 Hz, 2H), 1.35 (s, 9H), 1.07 (sept, J=6.9 Hz, 6H), 0.90 (d, J=7.3 Hz, 36H), 0.46 (s, 3H), 0.38 (s, 3H).

Step 2: Preparation of tert-butyl 3,7-dihydroxy-5,5-dimethyl-3'-oxo-3'H,5H-spiro[dibenzo[b,e]siline-10,1'-isobenzofuran]-6'-carboxylate Compound 19.2

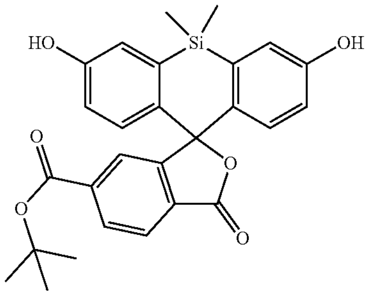

tert-butyl 5,5-dimethyl-3'-oxo-3,7-bis((triisopropylsilyl)oxy)-3'H,5H-spiro[dibenzo[b,e]siline-10,1'-isobenzofuran]-6'-carboxylate (216 mg, 0.274 mmol) was dissolved in THE (2.16 mL) and cooled to 0° C. To the solution as added TBAF (1M in THF, 1.1 mL, 0.274 mmol). The solution color turned dark purple. After 30 minutes, 12 sat. $NH_4Cl$ was added. The solution color turned pale orange. The mixture was extracted with ethyl acetate (3×50 mL), organic layers were combined, preabsorbed onto silica gel and purified by flash chromatography (eluent: 0-10% ethyl acetate in DCM) to afford the title compound as a translucent film (126 mg, 97%). m/z=475.1 [M+2H]+.

Step 3: Preparation of tert-butyl 5,5-dimethyl-3'-oxo-3,7-bis(((trifluoromethyl)sulfonyl)oxy)-3'H,5H-spiro[dibenzo[b,e]siline-10,1'-isobenzofuran]-6'-carboxylate Compound 19.3

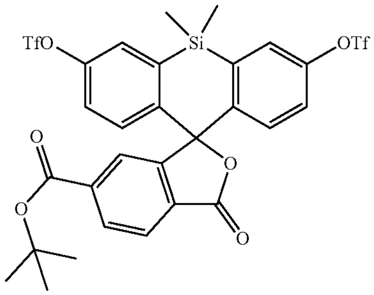

tert-Butyl 3,7-dihydroxy-5,5-dimethyl-3'-oxo-3'H,5H-spiro[dibenzo[b,e]siline-10,1'-isobenzofuran]-6'-carboxylate (263 mg, 0.554 mmol) and N-phenylbistriflamide (792 mg, 2.22 mmol) were suspended in THE (12 mL). N,N-Disopropylethylamine (579 μL, 3.33 mmol) was added slowly to the mixture. The resulting mixture was sealed and heated to 60° C. overnight. The mixture was cooled to room temperature, absorbed onto celite, and purified by silica gel flash chromatography (eluent: 0-8% MeOH in DCM) to afford the title compound as a white foam (341 mg, 83%). m/z=739.1 [M+H]+.

Step 4: Preparation of tert-butyl 3,7-bis(3-(dimethylcarbamoyl)azetidin-1-yl)-5,5-dimethyl-3'-oxo-3'H,5H-spiro[dibenzo[b,e]siline-10,1'-isobenzofuran]-6'-carboxylate Compound 19.4

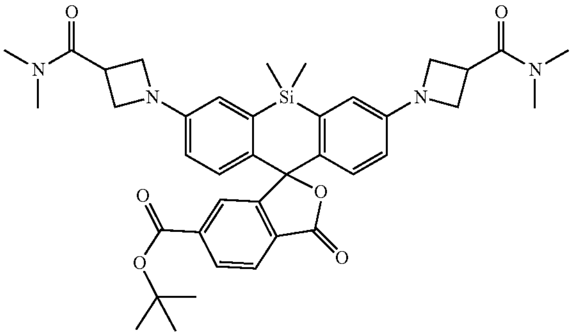

An oven dried one dram vial was charged with N,N-dimethylazetidine-3-carboxamide hydrochloride (61.9 mg, 0.308 mmol), $Cs_2CO_3$ and dioxane (1.23 mL). Tert-butyl 5,5-dimethyl-3'-oxo-3,7-bis(((trifluoromethyl)sulfonyl)oxy)-3'H,5H-spiro[dibenzo[b,e]siline-10,1'-isobenzofuran]-6'-carboxylate (91 mg, 0.123 mmol) and XPhos (17.6 mg, 0.037 mmol) were added. The mixture was sparged with Ar for 5 min. Then, $Pd_2dba_3$ (11.3 mg, 0.012 mmol) was added. The vial was sealed and heated to 100° C. overnight. The mixture was cooled to room temperature, diluted with MeOH, absorbed onto silica gel, and purified by flash chromatography (eluent: 2-20% MeOH in $CH_2Cl_2$) to afford the title compound as an orange-brown solid (81 mg, 95%) m/z=695.4 [M+H]+.

Step 5: Preparation of 3,7-bis(3-(dimethylcarbamoyl)azetidin-1-yl)-5,5-dimethyl-3'-oxo-3'H,5H-spiro[dibenzo[b,e]siline-10,1'-isobenzofuran]-6'-carboxylic acid Compound 19.5

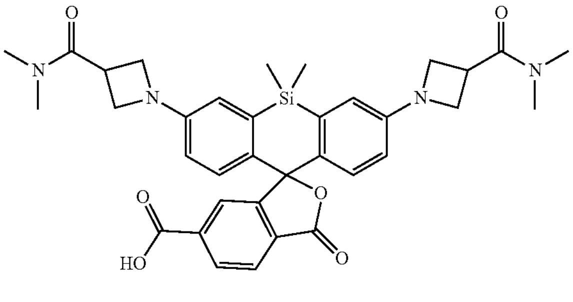

A solution of tert-butyl 3,7-bis(3-(dimethylcarbamoyl) azetidin-1-yl)-5,5-dimethyl-3'-oxo-3'H,5H-spiro[dibenzo[b, e]siline-10,1'-isobenzofuran]-6'-carboxylate (70 mg, 0.101 mmol) in $CH_2Cl_2$ (3.73 mL) was cooled to 0° C. Then trifluoroacetic acid (0.750 mL) was added dropwise. The solution color changed from yellow to green to dark red. The mixture was allowed to warm to room temperature and stir overnight. The dark green mixture was then concentrated to afford the title compound which was used directly in the next step without further purification. m/z=639.3 [M+H]+.

Step 6. Preparation of 1,1'-(6'-((2-(2-((6-chloro-hexyl)oxy)ethoxy)ethyl)carbamoyl)-5,5-dimethyl-3'-oxo-3'H,5H-spiro[dibenzo[b,e]siline-10,1'-isobenzo-furan]-3,7-diyl)bis(N,N-dimethylazetidine-3-carboxamide Compound 19.6

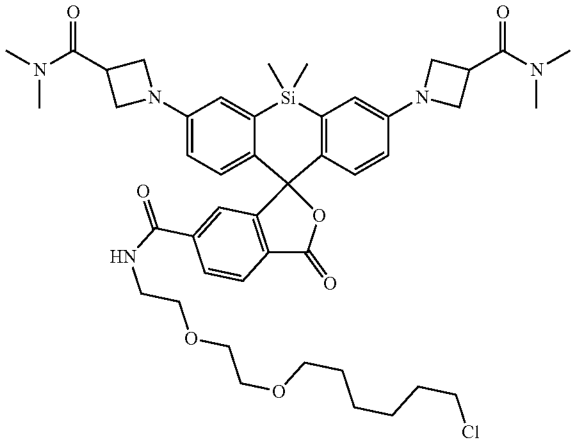

To a solution of 3,7-bis(3-(dimethylcarbamoyl)azetidin-1-yl)-5,5-dimethyl-3'-oxo-3'H,5H-spiro[dibenzo[b,e]siline-10,1'-isobenzofuran]-6'-carboxylic acid (16 mg, 0.025 mmol) in DMF (0.764 mL) was added TBTU (9.65 mg, 0.030 mmol), HOBT (5.75 mg, 0.030 mmol), and N,N-diisopropylethylamine (8.73 μL, 0.050 mmol). The solution turned from dark blue to light green to pale brown. 1-[2-(2-Aminoethoxy)ethoxy]-6-chlorohexane (7.82 mg, 0.030 mmol) was then added and the mixture was allowed to stir at room temperature overnight. The mixture was concentrated and the blue-green film was diluted with DMSO, and filtered. The mixture was purified by reverse phase preparatory HPLC (10-100% ACN/water (0.05% formic acid)) to afford the title compound as a pale green solid (4 mg, 19%) m/z=844.4 [M+H]+.

Step 7. Preparation of 1,1'-(6'-((2-(2-((6-chloro-hexyl)oxy)ethoxy)ethyl)carbamoyl)-2'-diazo-5,5-dimethyl-3'-oxo-2',3'-dihydro-5H-spiro[dibenzo[b,e]siline-10,1'-indene]-3,7-diyl)bis(N,N-dimethylazetidine-3-carboxamide Compound 19.7

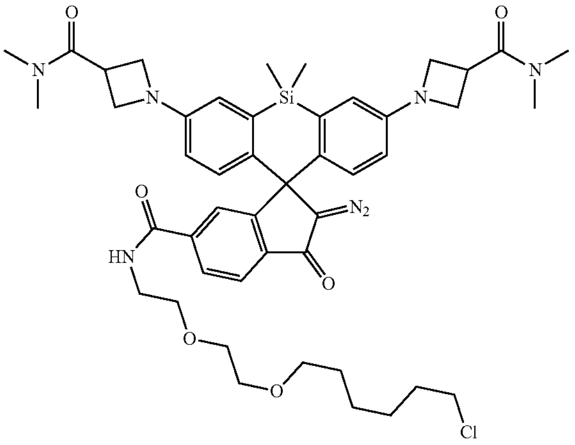

To a solution of 1,1'-(6'-((2-(2-((6-chlorohexyl)oxy)ethoxy)ethyl)carbamoyl)-5,5-dimethyl-3'-oxo-3'H,5H-spiro[dibenzo[b,e]siline-10,1'-isobenzofuran]-3,7-diyl)bis(N,N-dimethylazetidine-3-carboxamide) (7 mg, 8.29 μmol) in 1:1 $CH_2Cl_2$/ACN (2 mL) in an oven dried vial, was added 1-chloro-N,N,2-trimethylprop-1-en-1-amine (4.39 μL, 33.2 μmol). The solution colored turned deep blue. The mixture was stirred for 5 minutes, then $TMSCHN_2$ (2M in $Et_2O$, 16.6 μL, 33.2 μmol) and N,N-diisopropylethylamine (5.78 μL, 33.2 μmol) were added dropwise. The mixture was stirred for 30 mins at room temperature. The mixture was concentrated. The residue was purified by reverse phase preparative HPLC (10-100% can/water (0.1% formic acid)) to afford the title compound as a solid (0.5 mg, 7%). m/z=868.4 [M+H]+.

9.20 Example 20

Synthesis of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxamide Compound 20

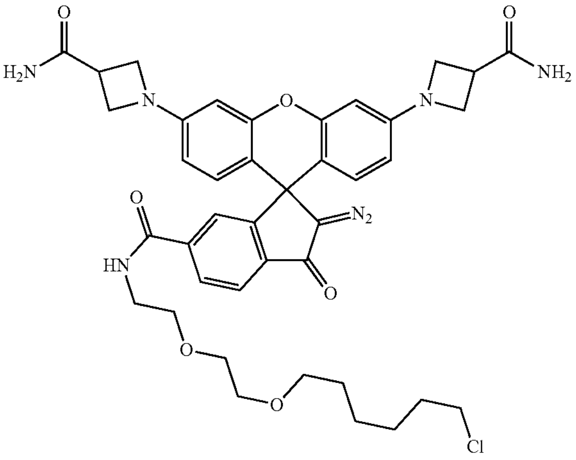

To a stirred solution of 1,1'-(6-((2-(2-((6-chlorohexyl)oxy)ethoxy)ethyl)carbamoyl)-2-diazo-3-oxo-2,3-dihydrospiro[indene-1,9'-xanthene]-3',6'-diyl)bis(azetidine-3-carboxylic acid) (0.040 g, 0.052 mmol, Example 2) in DMF (1 mL) at 0° C. was added N,N'-diisopropylethylamine (0.054 mL, 0.311 mmol) followed by T3P (50% in ethyl acetate, 0.132 g, 0.207 mmol). The mixture was stirred at 0° C. for 1 h, then ammonium bicarbonate (0.041 g, 0.518 mmol) was added. The mixture was warmed to room temperature and stirred at room temperature for 12 h, then ice cold water (10 mL) was added and the mixture was extracted with ethyl acetate (10 mL×2). The combined organic layers were dried over anhydrous sodium sulphate and concentrated under reduced pressure. The residue was purified by preparatory HPLC (C18; mobile phase, 0-100% ACN in water) to afford the title compound (0.0052 g, 13% yield) as pale-yellow solid. $^1$H NMR (400 MHz, DMSO-$d_6$): δ 8.69 (t, J=5.6 Hz, 1H), 7.97 (dd, J=1.6 Hz and 8.0 Hz, 1H), 7.83 (d, J=8.0 Hz, 1H), 7.47 (d, J=8.4 Hz, 1H), 7.46 (s, 2H), 6.99 (s, 2H), 6.68 (d, J=8.8 Hz, 2H), 6.21 (d, J=2.4 Hz, 2H), 6.14 (dd, J=2.0 Hz and 8.4 Hz, 2H), 3.97-3.95 (m, 4H), 3.85-3.80 (m, 4H), 3.60-3.57 (m, 2H), 3.47-3.34 (m, 10H), 1.67-1.63 (m, 2H), 1.67-1.63 (m, 2H), 1.40-1.38 (m, 2H), 1.24-1.23 (m, 4H) ppm. m/z 770.72 $[M+H]^+$.

9.21 Example 21

Synthesis of 3',6'-di(azetidin-1-yl)-6-((2-(2-((6-chlorohexyl)oxy)ethoxy)ethyl)amino)-3H-spiro[isobenzofuran-1,9'-xanthen]-3-one Compound 21

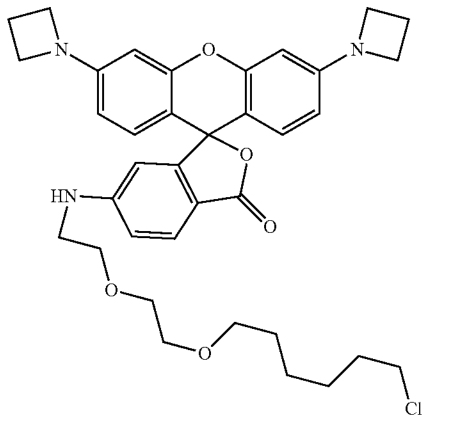

Step 1: Preparation of 2-((6-chlorohexyl) oxy) ethan-1-ol

Compound 21.1

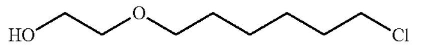

To a solution of ethane-1,2-diol (5 g, 80.5 mmol) in DMF (50 mL) at 0° C. under nitrogen was added NaH (60% in mineral oil) (3.86 g, 161.10 mmol) followed by 1-chloro-6-iodohexane (19.85 g, 80.55 mmol). The mixture was stirred at room temperature for 2 h. Mixture was then poured into ice water (500 mL) and extracted with EtOAc (2×100 mL). Organic layers were combined, dried over $Na_2SO_4$ and concentrated. The residue was purified by flash chromatography (eluent: 45% EtOAc in petroleum ether) to afford the title compound as a colorless oil (2 g, 13%).

Step 2: tert-butyl 3-(2-((6-chlorohexyl)oxy)ethoxy)propanoate

Compound 21.2

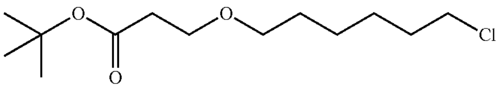

To a solution of 2-((6-chlorohexyl) oxy) ethan-1-ol (2.5 g, 13.9 mmol) in ACN (25 mL) was added N-benzyl-trimethylammonium hydroxide in $H_2O$ (0.277 g, 4.16 mmol) at room temperature over 10 minutes. Then, tert-butyl acrylate (8.9 g, 69.4 mmol) was added dropwise. The resulting solution was stirred for 16 h at room temperature, then concentrated. The resulting mixture was poured into ice water (50 mL), extracted with EtOAc (2×50 mL). The combined organic layers were dried over $Na_2SO_4$ and concentrated. The residue was purified by flash chromatography (eluent: 45% EtOAc in petroleum ether) to afford the title compound as a colorless oil (3 g, 70%).

Step 3: 3-(2-((6-chlorohexyl) oxy) ethoxy) propanal

Compound 21.3

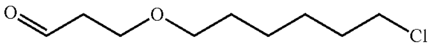

To a solution of tert-butyl 3-(2-((6-chlorohexyl) oxy) ethoxy) propanoate (0.5 g, 1.623 mmol) in −78° C. anhydrous THE (5 mL) was added DIBAL-H (1M in THF, 3.2 mL, 3.247 mmol) over 20 min. Resulting solution was allowed to stir at −78° C. for 1 h. Resulting mixture was quenched with a Rochelle's salt solution and extracted with EtOAc (2×30 mL). Organic fractions were combined, dried over $Na_2SO_4$, and concentrated. The residue was purified by flash chromatography (eluent: 45% EtOAc in petroleum ether) to afford the title compound as a colorless oil (0.2 g, 52%).

Step 4: Preparation of tert-butyl (3',6'-dibromo-3-oxo-3H-spiro[isobenzofuran-1,9'-xanthen]-6-yl)carbamate Compound 21.4

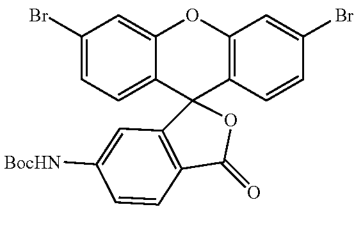

To a solution of pyridinium 3',6'-dibromo-3-oxo-3H-spiro[isobenzofuran-1,9'-xanthene]-6-carboxylate (25 g, 49.8 mmol, Compound B1) in THE (250 mL) was added triethylamine (23 mL, 174.3 mmol) and diphenylphosphoryl azide (14.8 mL, 64.72 mmol) at 0° C. The mixture was stirred at 0° C. for 30 minutes. The solution was slowly allowed to warm to room temperature and stirred for 16 h. The mixture was diluted with water and extracted with ethyl acetate. The organic layers were washed with $NaHCO_3$ and brine, dried with $Na_2SO_4$, and concentrated. The residue was suspended in tBuOH (500 mL) and stirred at 95° C. for 12 h. The mixture was cooled to room temperature, diluted with water (250 mL) and extracted with ethyl acetate (2×1 L). The combined organic layers were washed with $NaHCO_3$ solution and brine, then dried over $Na_2SO_4$, filtered and concentrated. The residue was purified by flash chromatography (eluent: 2-20% EtOAc in petroleum ether) to afford the title compound as an off-white solid. m/z=574.32 [M+H]+.

Step 5: Preparation of tert-butyl (3',6'-di(azetidin-1-yl)-3-oxo-3H-spiro[isobenzofuran-1,9'-xanthen]-6-yl)carbamate Compound 21.5

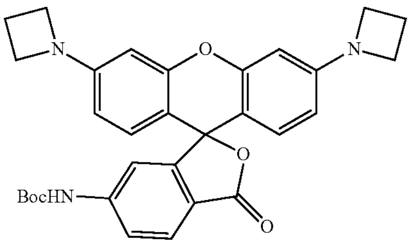

To a solution of tert-butyl (3',6'-dibromo-3-oxo-3H-spiro[isobenzofuran-1,9'-xanthen]-6-yl)carbamate (3.5 g, 6.13 mmol) and azetidine (1.4 g, 24.52 mmol) in 1,4-dioxane (70 mL), was added cesium carbonate (9.9 g, 30.65 mmol). The mixture was sparged with Ar for 15 min. Then $Pd_2(dba)_3$ (2.80 g, 3.06 mmol) followed by XPhos (0.87 g, 1.83 mmol) were added and the mixture was heated to 110° C. for 16 h. The mixture was cooled to room temperature, filtered through a celite pad and concentrated. The residue was purified by reverse phase C-18 chromatography (eluent: 0-100% ACN in water) to afford the title compound (1.4 g, 43%) as a dark pink solid m/z=574.32 [M+H]+.

Step 6: Preparation of 6-amino-3',6'-di(azetidin-1-yl)-3H-spiro[isobenzofuran-1,9'-xanthen]-3-one Compound 21.6

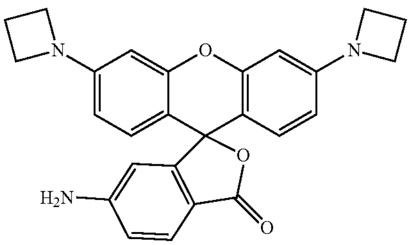

To a solution of tert-butyl (3',6'-di(azetidin-1-yl)-3-oxo-3H-spiro[isobenzofuran-1,9'-xanthen]-6-yl)carbamate (1.0 g, 1.90 mmol) in $CH_2Cl_2$ (10 mL) was added TFA (5 mL) at 0° C. and allowed to stir at room temperature for 6 h. The resulting solution was concentrated, quenched with saturated $NaHCO_3$ (40 mL), and extracted with 10% MeOH in $CH_2Cl_2$ (3×30 mL). The combined organic layers were dried over $Na_2SO_4$, and concentrated. The residue was purified by reverse phase C-18 column chromatography (eluent: 0-100% ACN in water) to afford the title compound (0.2 g, 25%) as a purple solid. m/z=426.35 [M+H]+.

Step 7: 3',6'-di(azetidin-1-yl)-6-((3-(2-((6-chlorohexyl)oxy)ethoxy)propyl)amino)-3H-spiro[isobenzofuran-1,9'-xanthen]-3-one Compound 21.7

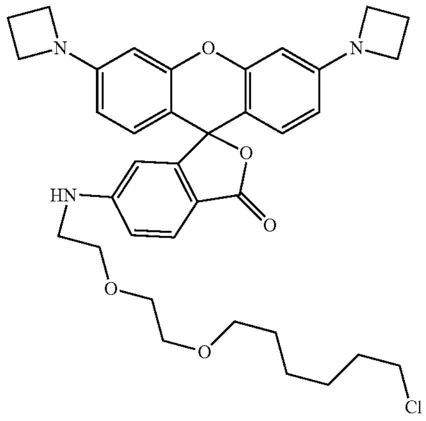

To a solution of 6-amino-3',6'-di(azetidin-1-yl)-3H-spiro[isobenzofuran-1,9'-xanthen]-3-one (0.2 g, 0.471 mmol) and 3-(2-((6-chlorohexyl) oxy)ethoxy)propanal (0.11 g, 0.471 mmol, Compound 21.3) in dichloroethane (2 mL) was added 2-3 drops acetic acid at room temperature. The resulting solution as stirred for 2 h. Then, sodium triacetoxyborohydride (0.199 g, 0.941 mmol) was added portion wise over 20 min at 0° C. The resulting mixture was stirred at room temperature for 2 h, then quenched with ice water and extracted by 10% MeOH in $CH_2Cl_2$ (2×25 mL). The organic layers were combined, dried over $Na_2SO_4$, and concentrated. The residue was purified by reverse phase column chromatography (eluent: 0-100% ACN in water) to afford the title compound (0.1 g, 32%) as a pink solid. m/z 646.50 [M+H]+.

Step 8: 3',6'-di(azetidin-1-yl)-6-((3-(2-((6-chlorohexyl)oxy)ethoxy)propyl)amino)-3H-spiro[isobenzofuran-1,9'-xanthen]-3-one Compound 21.8

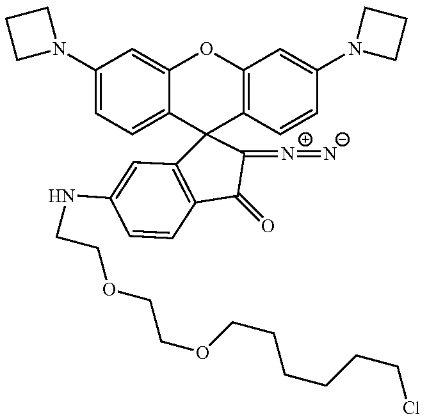

To a solution of 3',6'-di(azetidin-1-yl)-6-((3-(2-((6-chlorohexyl) oxy) ethoxy) propyl) amino)-3H-spiro[isobenzofuran-1,9'-xanthen]-3-one (0.1 g, 0.155 mmol) in $CH_2C_2$ (5 mL) at 0° C. under nitrogen atmosphere was added a solution of freshly distilled thionyl chloride (0.058 mL, 0.774 mmol) in $CH_2Cl_2$ (0.025 mL). The resulting solution was warm to room temperature for 30 min and then concentrated. The residue was diluted with in anhydrous $CH_2C_2$ (0.025 mL) then freshly prepared diazomethane in $Et_2O$ (10 mL, >25 eq) was added. The mixture was stirred at 0° C. for 30 min. The mixture was concentrated and the residue was purified by preparative reverse phase HPLC (eluent: 0-100% ACN in water) to afford the title compound (5 mg, 4.82%) as a brown gum. $^1H$ NMR (400 MHz, DMSO-$d_6$): δ 7.45 (d, J=8.8 Hz, 1H), 6.70-6.62 (m, 4H), 6.16-6.10 (m, 4H), 6.01 (s, 1H), 3.83-3.80 (m, 8H), 3.58 (t, J=6.4 Hz, 2H), 3.39-3.38 (m, 8H), 3.00-2.95 (m, 2H), 2.32-2.27 (m, 4H), 1.68-1.63 (m, 4H), 1.46-1.42 (m, 6H), ppm. m/z 668.37 $[M-H]^-$.

9.22 Example 22

Synthesis of 3-(2-((6-chlorohexyl)oxy)ethoxy)-N-(3',6'-di(azetidin-1-yl)-2-diazo-3-oxo-2,3-dihydrospiro[indene-1,9'-xanthen]-6-yl)propanamide Compound 22

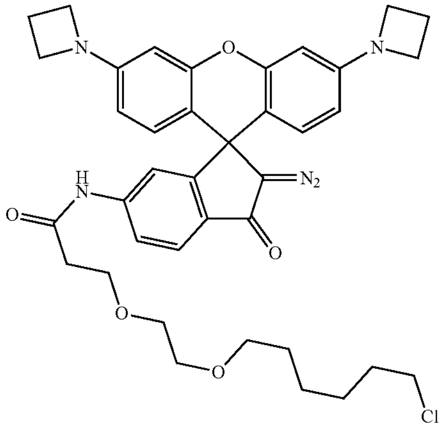

Step 1: Synthesis of 3-(2-((6-chlorohexyl)oxy)ethoxy)propanoic acid

Compound 22.1

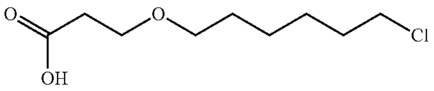

To a solution of tert-butyl 3-(2-((6-chlorohexyl)oxy)ethoxy)propanoate (Compound 21.2, 0.6 g, 1.947 mmol) in $CH_2Cl_2$ (12.0 mL) at 0° C. under Ar (g) atmosphere was added hydrochloric acid 4M in dioxane (12 mL) dropwise. Resulting mixture was allowed to room temperature and stirred for 4 h. Mixture was then concentrated to afford 3-(2-((6-chlorohexyl)oxy)ethoxy)propanoic acid (0.45 g; crude) as off-white solid. m/z 284.1 $[M+H]^+$.

Step 2. Synthesis of 3-(2-((6-chlorohexyl)oxy)ethoxy)-N-(3',6'-di(azetidin-1-yl)-3-oxo-3H-spiro[isobenzofuran-1,9'-xanthen]-6-yl)propanamide Compound 22.2

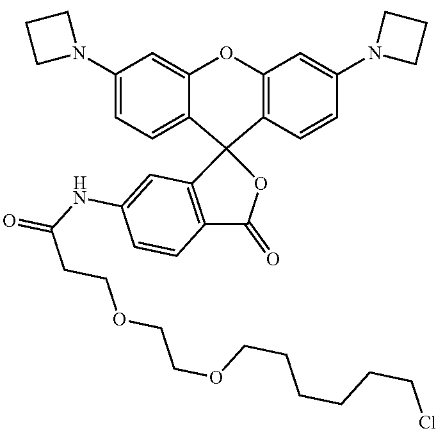

To a solution of 6-amino-3',6'-di(azetidin-1-yl)-3H-spiro[isobenzofuran-1,9'-xanthen]-3-one (Compound 21.6, 0.3 g, 0.705 mmol) and 3-(2-((6-chlorohexyl)oxy)ethoxy)propanoic acid (0.2 g, 0.705 mmol) in $CH_2Cl_2$ (15 mL) was added n-methylimidazole (0.28 mL, 3.53 mmol) dropwise at 0° C., followed by methanesulfonyl chloride (0.082 mL, 1.06 mmol). Mixture was allowed to room temperature and stirred for 1 h. The mixture was then concentrated and was purified by reverse phase HPLC (eluent: 0-100% acetonitrile in (10 mM ammonium acetate in water)) to afford the title compound (0.17 g; 36% yield) as pink solid. m/z 660.31 $[M+H]^+$.

Step 3: 3-(2-((6-chlorohexyl)oxy)ethoxy)-N-(3',6'-di(azetidin-1-yl)-2-diazo-3-oxo-2,3-dihydrospiro[indene-1,9'-xanthen]-6-yl)propanamide Compound 22.3

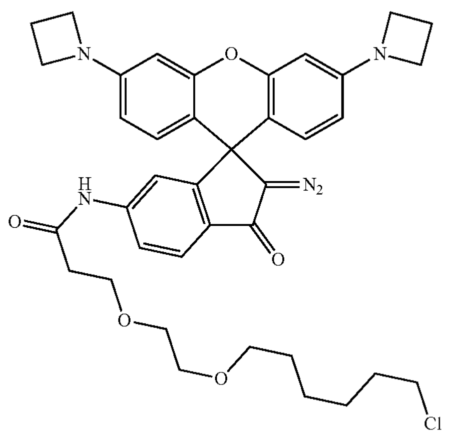

To a solution of N-(3'-(azetidin-1-yl)-6'-cyclobutyl-3-oxo-3H-spiro[isobenzofuran-1,9'-xanthen]-6-yl)-3-(2-((6-chlorohexyl)oxy)ethoxy)propanamide (0.15 g, 0.228 mmol) in $CH_2C_2$ (30 mL) at 0° C. under argon atmosphere was added oxalyl chloride (0.2 mL, 2.28 mmol) drop. The mixture was warm room temperature and stirred for 1 h. Freshly prepared diazomethane (~30 mL, >25 eq) was then added drop wise at 0° C. The mixture was stirred for 1 h. Resulting solution was then concentrated and purified by reverse phase preparative HPLC (eluent: 0-100% ACN in water) to afford Example 22 (0.012 g, 8%) as a pale brown solid. NMR (400 MHz, DMSO-d6): δ 10.2 (s, 1H), 7.70-7.63 (m, 2H), 7.37 (d, J=1.2 Hz, 1H), 6.70 (d, J=8.4 Hz, 2H), 6.15-6.11 (m, 4H), 3.82-3.80 (m, 8H), 3.62-3.56 (m, 4H), 3.45-3.38 (m, 4H), 3.31-3.27 (m, 2H), 2.47-2.45 (m, 2H), 2.33-2.27 (m, 4H), 1.66-1.63 (m, 2H), 1.41-1.30 (m, 4H), 1.25-1.20 (m, 2H) m/z 684.5 $[M+H]^+$.

9.23 Example 23

Synthesis of (E)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one and (Z)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one Compound 23

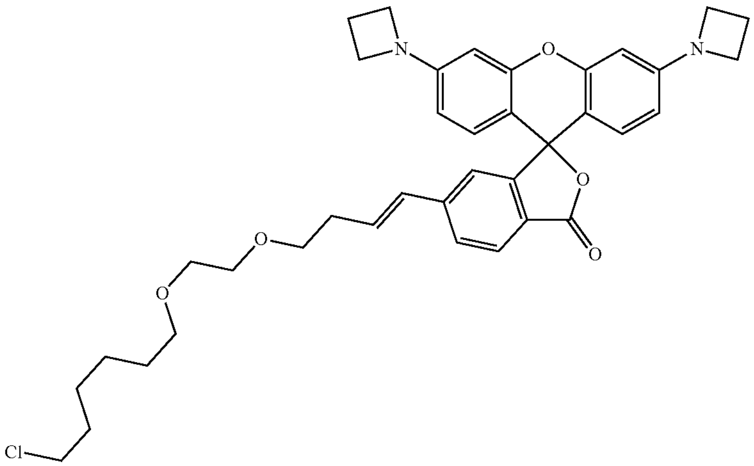

&

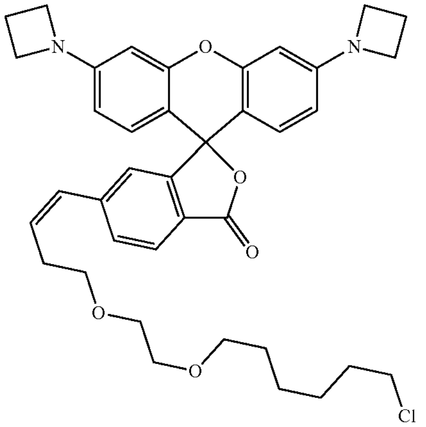

Step 1: Preparation of 2-((6-chlorohexyl)oxy)ethan-1-ol

Compound 23.1

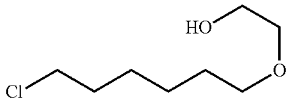

To a stirred solution of ethane-1,2-diol (5.0 g, 80.55 mmol) in DMF (50 mL) was added sodium hydride 60% (6.44 g, 161.11 mmol) at −10° C. and the mixture was stirred at −10° C. for 15 min. The mixture was added 1-chloro-6-iodohexane (19.86 g, 80.55 mmol) at −10° C., then mixture was warmed to room temperature and stirred at room temperature for 2 h. Then to the mixture was added ice water (0.5 L) and the mixture was extracted with ethyl acetate (2×500 mL). The combined organic layers were washed with brine solution and dried over sodium sulphate, and concentrated. The residue was purified by silica gel column chromatography (eluent: 0-20% ethyl acetate with petroleum ether) to afford the title compound (0.9 g, 6%) as pale yellow liquid.

Step 2: Preparation of 2-((6-chlorohexyl)oxy)ethyl methanesulfonate

Compound 23.2

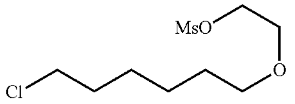

To a stirred solution of 2-((6-chlorohexyl)oxy)ethan-1-ol (1.5 g, 8.302 mmol) in dichloromethane (15.0 mL) at 0° C. was added triethylamine (1.4 mL, 9.963 mmol), followed by methanesulfonyl chloride (1.05 g, 9.133 mmol). The mixture was warmed to room temperature and stirred at room temperature for 1 h. Then ice water (50 mL) was added and the mixture was extracted with dichloromethane (2×50 mL). The combined organic layers were washed with brine, dried over sodium sulphate and concentrated to afford the title compound (1.5 g, 70%) as pale yellow liquid which was used in the next step without further purification.

Step 3: Preparation of 1-(2-(but-3-yn-1-yloxy)ethoxy)-6-chlorohexane

Compound 23.3

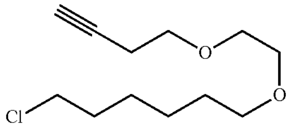

To a stirred solution of but-3-yn-1-ol (0.8 g, 11.41 mmol, Compound 23.2) in DMF (8.0 mL) at 0° C. was added sodium hydride 60% (0.457 g, 11.41 mmol) and the mixture was stirred at 0° C. for 30 min. Then 2-((6-chlorohexyl)oxy)ethyl methanesulfonate (1.48 g, 5.71 mmol) was added. The mixture was warmed to room temperature and stirred at room temperature for 16 h. Then ice water (80 mL) was added and the mixture was extracted with ethyl acetate (80 mL). The combined organic layers were washed with brine, dried over sodium sulfate and then concentrated. The residue was purified by silica gel column chromatography (eluent: 0-15% ethyl acetate with petroleum ether) to afford the title compound as colorless liquid.

Step 4: Preparation of 3',6'-di(azetidin-1-yl)-6-iodo-3H-spiro[isobenzofuran-1,9'-xanthen]-3-one Compound 23.4

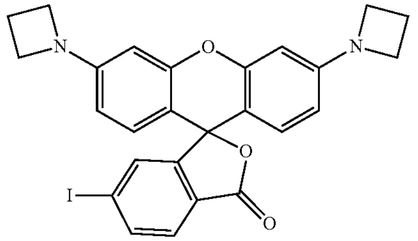

To a stirred solution of 6-amino-3',6'-di(azetidin-1-yl)-3H-spiro[isobenzofuran-1,9'-xanthen]-3-one (2.5 g, 5.88 mmol, Compound 21.6) in ACN (10 mL) at 0° C. was added CuI (0.67 g, 3.52 mmol) and tBuONO (0.57 mL, 4.70 mmol). The mixture was stirred at 50° C. for 2 h. Then a solution of sodium thiosulphate in water was added and the mixture was extracted with 10% MeOH in DCM (3×80 mL). The combined organic layers were dried over $Na_2SO_4$, and then concentrated. The residue was purified by preparatory HPLC (mobile phase 0-100% ACN in water) to afford the title compound (1.0 g, 31%) as purple solid.

Step 5: Preparation of 3',6'-di(azetidin-1-yl)-6-(4-(2-((6-chlorohexyl)oxy)ethoxy)but-1-yn-1-yl)-3H-spiro[isobenzofuran-1,9'-xanthen]-3-one Compound 23.5

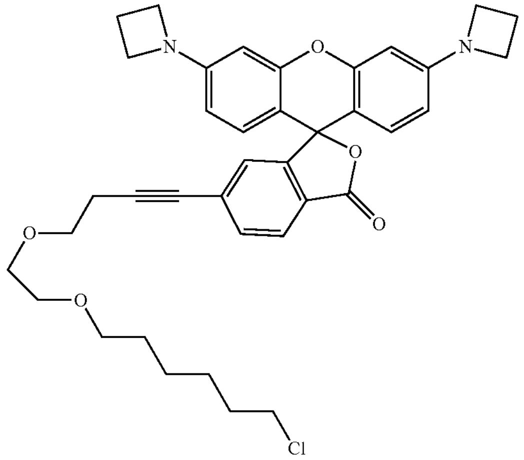

To a stirred solution of 1-(2-(but-3-yn-1-yloxy)ethoxy)-6-chlorohexane (0.15 g, 0.644 mmol, Compound 23.3) and 3',6'-di(azetidin-1-yl)-6-iodo-3H-spiro[isobenzofuran-1,9'-xanthen]-3-one (0.346 g, 0.644 mmol, Compound 23.4) in DMF (4.5 mL) was added triethylamine (4.5 mL), copper iodide (0.012 g, 0.064 mmol), and bis(triphenylphosphine) palladium(II) chloride (0.045 g, 0.064 mmol). The mixture was stirred at room temperature for 2 h. Then the mixture was concentrated under reduced pressure. The residue was purified by reverse phase column elution with 50-60% acetonitrile with 10 mM of ammonium bicarbonate in water) to afford the title compound (0.12 g; 24%) as pink solid.

Step 6: Preparation of (E)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one and (Z)-3',6'-di(azetidin-1-yl)-6-(4-(2-((6-chlorohexyl)oxy)ethoxy)but-1-en-1-yl)-3H-spiro[isobenzofuran-1,9'-xanthen]-3-one Compound 23.6

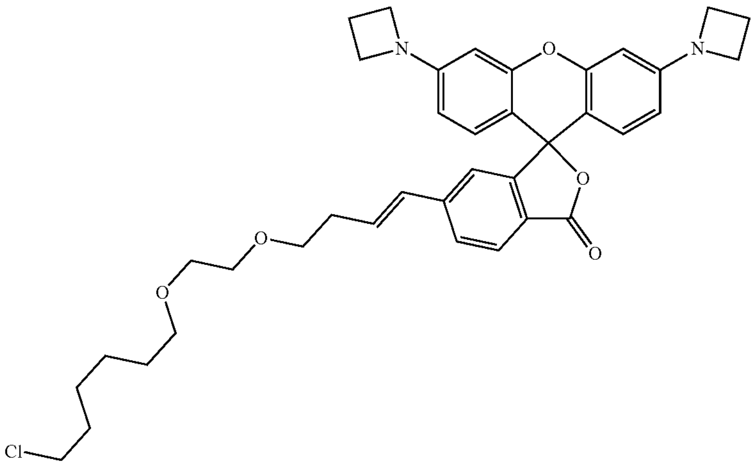

&

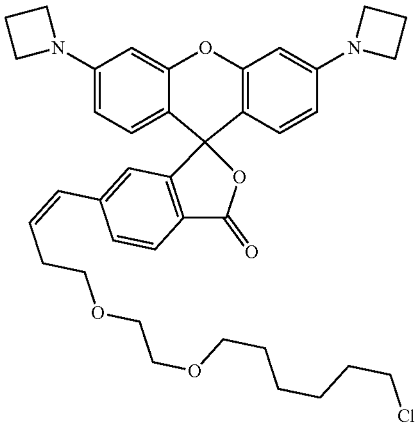

To a stirred solution of 3',6'-di(azetidin-1-yl)-6-(4-(2-((6-chlorohexyl)oxy)ethoxy)but-1-yn-1-yl)-3H-spiro[isobenzofuran-1,9'-xanthen]-3-one (0.1 g, 0.156 mmol) in ethanol (10.0 mL) was added 10% Palladium on carbon with 50% wet (0.1 g). The mixture was stirred at room temperature under hydrogen for 12 h. Then the mixture was filtered through celite and concentrated. The residue was purified by reverse phase column (elution with 50-80% acetonitrile with 10 mM of ammonium bicarbonate in water) to afford the title compounds as the first eluting mixture (0.025 g; 24% yield).

Step 7: Preparation of (E)-3',6'-di(azetidin-1-yl)-6-(4-(2-((6-chlorohexyl)oxy)ethoxy)but-1-en-1-yl)-2-diazospiro[indene-1,9'-xanthen]-3(2H)-one and (Z)-3',6'-di(azetidin-1-yl)-6-(4-(2-((6-chlorohexyl)oxy)ethoxy)but-1-en-1-yl)-2-diazospiro[indene-1,9'-xanthen]-3(2H)-one To a stirred solution of 3',6'-di(azetidin-1-yl)-6-(4-(2-((6-chlorohexyl)oxy)ethoxy)but-1-en-1-yl)-3H-spiro[isobenzofuran-1,9'-xanthen]-3-one (E:Z mixture) (0.02 g, 0.031 mmol, Compound 23.6) in dichloromethane (4.0 mL) at 0° C. was added oxalyl chloride (0.03 mL, 0.31 mmol) under argon atmosphere, then the mixture was warmed to room temperature and stirred for 1 h. Then the mixture was concentrated and backfilled under argon. Freshly prepared diazomethane in diethyl ether solution (4.0 mL) was added to the residue at 0° C. and the mixture was stirred for 1 h. Then the mixture was concentrated and the residue was purified by preparatory HPLC (C18; mobile phase: 0-100% ACN/water) to afford the title compounds (0.0022 g, 10%) as brown gum. m/z 667.5 [M+H]$^+$.

Compound 23.7

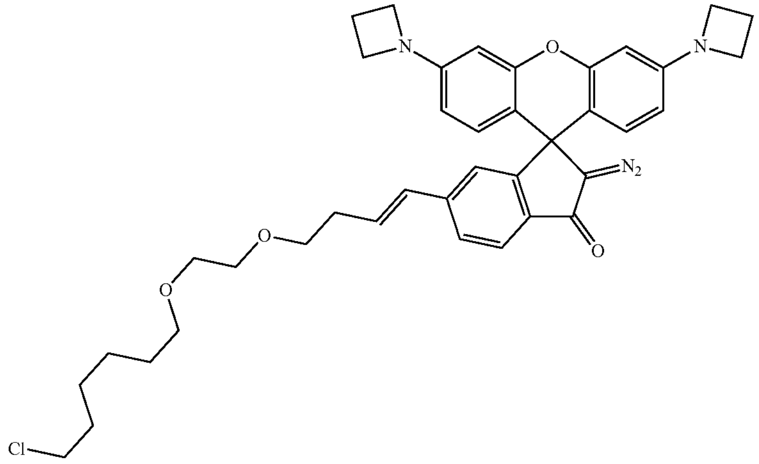

&

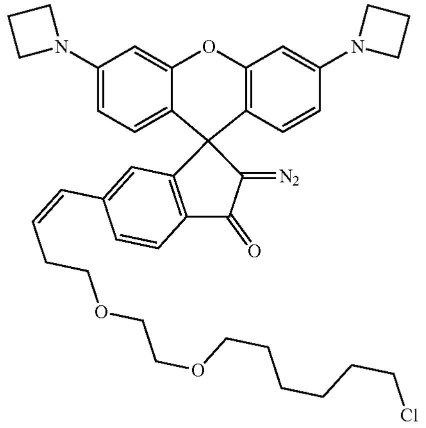

9.24 Example 24

Synthesis of 3',6'-di(azetidin-1-yl)-6-(4-(2-((6-chlorohexyl)oxy)ethoxy)butyl)-2-diazospiro[indene-1,9'-xanthen]-3 (2H)-one Compound 24

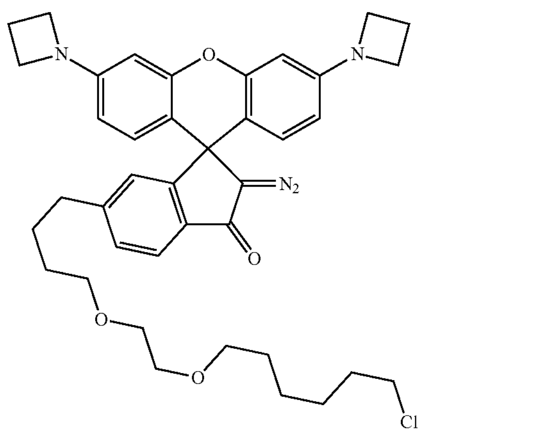

Step 1: Preparation of 3',6'-di(azetidin-1-yl)-6-(4-(2-((6-chlorohexyl)oxy)ethoxy)butyl)-3H-spiro[isobenzofuran-1,9'-xanthen]-3-one Compound 24.1

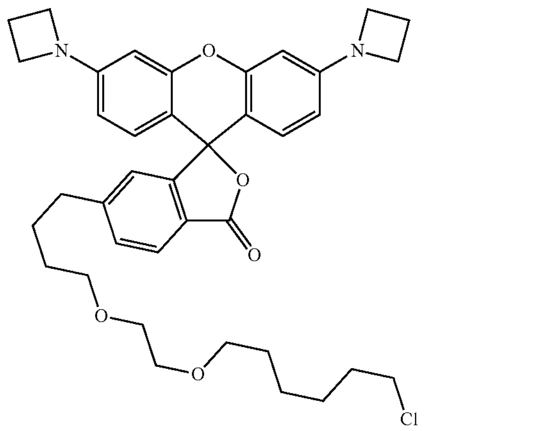

Further elution of the reverse phase column of Compound 23, Step 6 afforded the title compound (0.02 g; 20% yield) as pink solid.

Step 2: Preparation of 3',6'-di(azetidin-1-yl)-6-(4-(2-((6-chlorohexyl)oxy)ethoxy)butyl)-2-diazospiro[indene-1,9'-xanthen]-3(2H)-one Compound 24.2

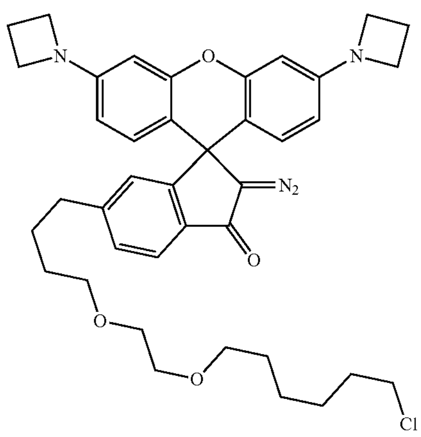

To a stirred solution of 3',6'-di(azetidin-1-yl)-6-(4-(2-((6-chlorohexyl)oxy)ethoxy)butyl)-3H-spiro[isobenzofuran-1,9'-xanthen]-3-one (0.02 g, 0.031 mmol) in dichloromethane (4.0 mL) at 0° C. was added oxalyl chloride (0.03 mL, 0.31 mmol) under argon atmosphere. The mixture was warmed to room temperature and stirred at room temperature for 1 h, then the mixture was concentrated under argon atmosphere. Freshly prepared diazomethane in diethyl ether solution (4.0 mL) was added to the residue at 0° C. and the mixture was stirred at 0° C. for 1 h, then the mixture was concentrated. The residue was purified by preparatory HPLC (C18; mobile phase, 0-100% ACN in water) to afford the title compound (0.025 g, 12%) as brown gum. $^1$HNMR (400 MHz, DMSO-d6): δ 7.67 (d, J=8.0 Hz, 1H), 7.35 (d, J=8.0 Hz, 1H), 6.81 (s, 1H), 6.64 (d, J=8.4 Hz, 2H), 6.14 (dd, J=2.0 Hz, 2.0 Hz, 4H), 3.83 (t, J=7.2 Hz, 8H), 3.59 (t, J=6.8 Hz, 2H), 3.38-3.31 (m, 8H), 2.57-2.53 (m, 2H), 2.32-2.27 (m, 4H), 1.67-1.63 (m, 2H), 1.48-1.31 (m, 10H) ppm. m/z 669.5 [M+H]+.

9.25 Example 25: Kinetic Solubility in PBS at 7.4

190 μL of buffer solution (PBS, pH 7.4) was added to wells on a 96-well Millipore Solubility filter plate. Then 10 μL of test compound in DMSO (10 mM) were added to give final concentration of 500 μM.

The filter plate was shaken for 1.5 hours at room temperature in the dark and samples were filtered via a vacuum system into a fresh 96-well plate. Samples were diluted to 500 μM (highest concentration) in DMSO and further diluted (1:10) to provide three-point calibration curve. Absorbance was measured using HPLC/UV analysis at 220 nm, 254 nm, and 280 nm. Data was reported as an average of three runs per test compound and is shown in Table 1 below.

TABLE 1

| Kinetic solubility values | |
|---|---|
| Example # | Ksol (μM) |
| 1 | 58.4 |
| 2 | 481 |
| 3 | 39.5 |
| 4 | 3.69 |

9.26 Example 26: Passive Permeability

MDCK-MDR1 cells were plated into 96-well Millipore Millicell-96 plates at 7,500 cells/75 μL/well and incubated for three days at 37° C. with 5% $CO_2$. Then cells were washed with Hank's Balanced Salt Solution (HBSS) with 5 mM HEPES for 30 minutes. A solution of the test compound in DMSO (10 mM) was added to HBSS buffer with 10 μM GF-120918, to give a final DMSO concentration of 0.2% and test compound concentration of 5 μM. Transport plates were incubated at 37° C. for one hour in a humidified incubator with 5% $CO_2$. Samples were taken from the apical and basolateral compartments after one hour and analyzed by liquid chromatography with tandem mass spectrometry (LC/MS/MS, AB Sciex API 4000 instrument, coupled to a Shimadzu LC-20AD LC Pump system). Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

Apparent permeability (Papp, A2B) values were calculated using the following equation:

$$Papp=(dQ/dt)/A/C0$$

where dQ/dt is the initial rate of amount of test compound transported across cell monolayer, A is the surface area of the filter membrane, and C0 is the initial concentration of the test compound, calculated for each direction using a 4-point calibration curve by LC/MS/MS. Data is reported as an average of two runs and is shown in Table 2 below.

TABLE 2

| Passive permeability values | |
|---|---|
| Example # | Papp, A2B (×10−6 cm/s) |
| 1 | <0.1 |
| 2 | 0.49 |
| 3 | <0.1 |
| 4 | 4 |

9.27 Example 27: Protein Labeling with Photoactivatable Dye

60 μM 6×His-tagged HaloTag protein (expressed and purified from pH6HTC His6HaloTag T7 vector from Promega) was incubated with 200 μM dye compound in a 200 μL solution (50 mM HEPES pH 7.4, 150 mM NaCl, 0.01% NP40 alternative, 0.5 mM EDTA, 1 mM DTT and 2% DMSO) at room temperature for 30 min, then at 4° C. for 18 hr. Solution was illuminated with the centre of a 6× beam-expanded 405 nm laser (365 mW) for 5 min. The solution was filtered through 2 mL 7K MWCO Zeba Spin Desalting Column (Thermo Scientific) (prebalanced with 25 mM HEPES pH 7.6, 100 mM KCl, 0.1 mM EDTA, 12.5 mM $MgCl_2$, 1 mM DTT and 10% glycerol) twice. Labelled protein conjugate in the supernatant was analysed SDS-PAGE protein gel.

9.28 Example 28: Halo-Protein Specificity

Wild-type (WT) U2OS cells or U2OS cells ectopically expressing a histone H2B-HaloTag fusion under the control of a CMV promoter (H2B) were plated at 6000 cell/50 μL/well in a glass-bottomed 384-well plate and incubated at 37° C. and 5% $CO_2$ overnight. The following day the cells were incubated with PA-JF549 or Examples 1-4 at a range of concentrations between 200 nM and 1 nM for 45 minutes. After incubation, cells were washed three times with PBS and finally the media replaced with phenol-free media for imaging. Samples were imaged on a Nikon Ti2 microscope with fiber-optic coupled illumination source. 561 nm light (approx. 500 mW at the coverslip) was used to stimulate emission of the fluorophore. Images were collected every 10 msec for 5 seconds per field of view and pulses of ascending intensity 405 nm light (between 0 and 12 mW at the coverslip) were used to photoactivate dye molecules. Approximately 20 fields of view were collected per cell-line/dye compound/concentration set.

All frames from each field of view were analyzed using a maximum likelihood estimator model to detect single molecule fluorescence emissions within an image with sub-pixel precision. For each dye compound, a linear regression was used to determine the relationship between the concentration of dye compound and the number of fluorescence spots detected on the microscope, where in WT cells the ideal dye would have no correlation between compound concentration and number of slots measured. The Specificity Factor was calculated as the ratio of the slope of the compound in question relative to the slope calculated for PA-$JF_{549}$ and is shown in Table 3 below.

TABLE 3

| Specificity Factor | |
|---|---|
| Example # | Specificity Factor |
| 1 | 2.66 |
| 2 | <1 |
| 3 | 2.07 |
| 4 | 23.8 |

9.29 Example 29: Labeling Specificity

Figure 3:
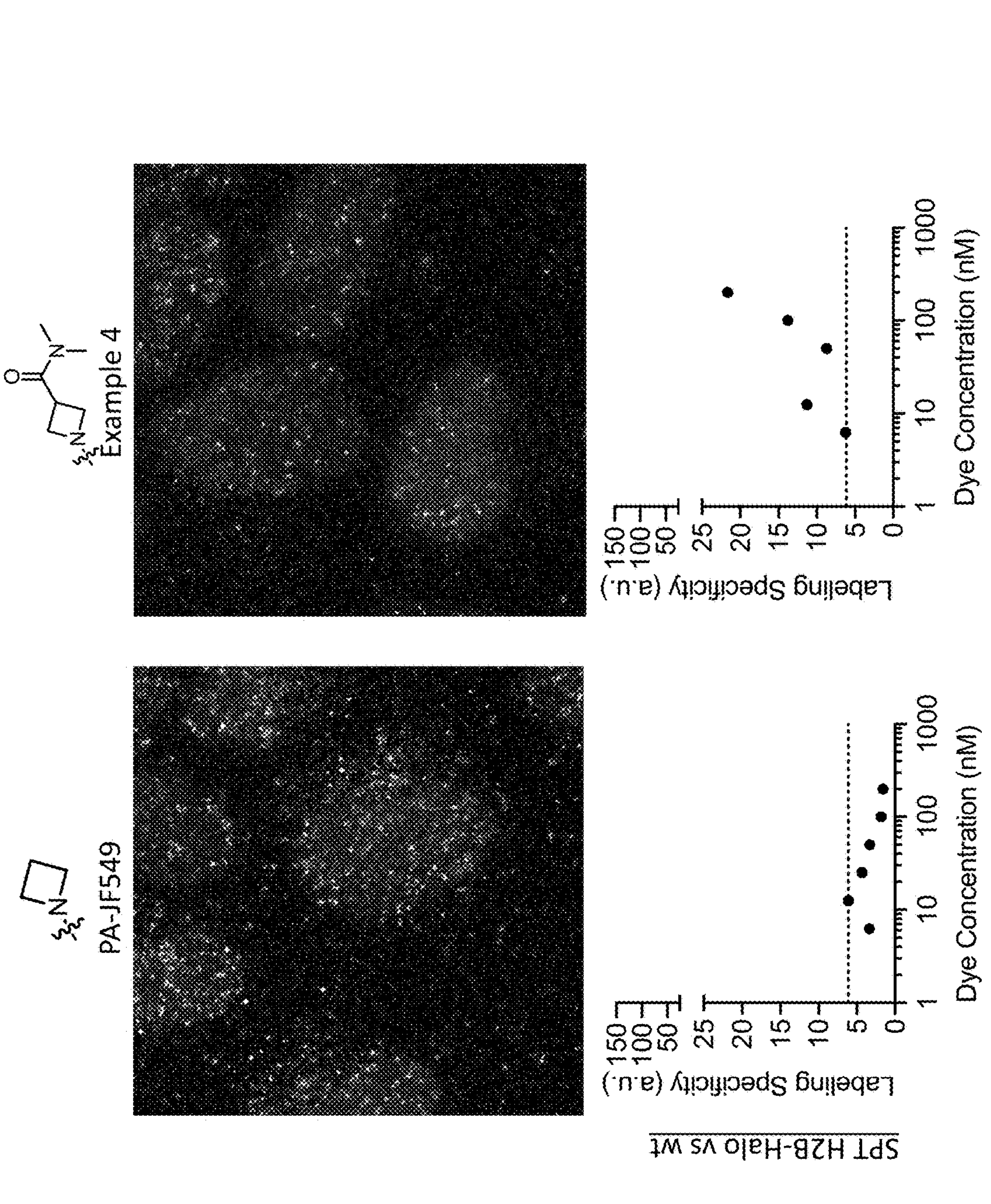
FIG. 3 shows the relative labeling specificity of PA-$JF_{549}$ compared to the photoactivatable dye compound of Example 4. Labeling specificity was calculated using Histone H2B located in the nucleus of wildtype cells not expressing any HaloTag® protein.

Using the methods described in Example 8 above, labeling specificity of the compound of Examples 1-4 was measured and compared to PA-$JF_{549}$. U2OS cells wild type or expressing H2B-HaloTag fusion were incubated with PA-$JF_{549}$ or Example 4 for 45 min. FIG. 3 shows an example field of view H2B-HaloTag Fusion expressing U2OS, nucleus labeled with Hoechst 33342 dye. Labeling specificity was calculated by number of spots detected at a given concentration of dye in H2B-HaloTag expressing U2OS cells divided by number of spots detected at the same concentration in U2OS wild-type cells.

9.30 Example 30: Signal to Noise Ratio

Figure 4:
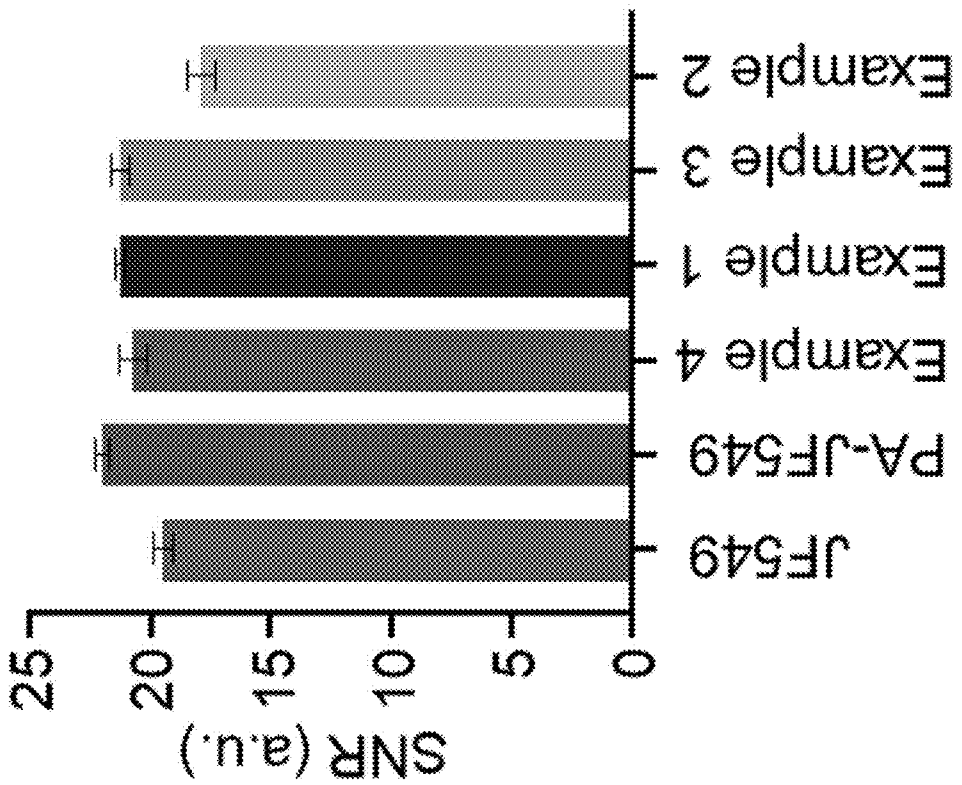
FIG. 4 shows signal to noise ratio (SNR) for $JF_{549}$, PA-$JF_{549}$, and photoactivatable dye compounds of Examples 1-4.

SNR, which is a proxy for single molecule brightness, was calculated for Examples 1-4 (see FIG. 4). Each spot in the SPT experiment described Example 8 was calculated using a log likelihood ratio test for the presence of a 2D Gaussian spot. See Serge et al., "Dynamic multiple-target tracing to probe spatiotemporal cartography of cell membranes," *Nat. Methods* 2008, 5(8), 687-694 (Sergé et al., 2008). The SNR of each spot was reported as its peak log likelihood ratio. This calculation uses a fixed-width 2D Gaussian PSF model with sigma/standard deviation equal to 0.183 μm. Only spots with SNR>=14 are included in this calculation, due to the stringency of our spot detection filter. The bars in FIG. 4 are the mean SNRs across biological replicates, while the error bars are the standard error of the mean SNR across biological replicates.

9.31 Example 31: Reduction in Nonspecific Labeling

Wild-type (WT) U20S cells or U20S cells ectopically expressing an Estrogen Receptor-HaloTag (ER-Halo) fusion were plated at 6000 cell/50 μL/well in a glass-bottomed 384-well plate and incubated at 37° C. and 5% $CO_2$ and 95% humidity overnight. The following day the cells were incubated with JF549, PA-JF549, or Examples 1-24 at a concentration of 100 nM (20 μM in the case of conventional $JF_{549}$), and 100 nM Potomac Red for 1 hr. After incubation, cells were washed three times with PBS and finally the media replaced with phenol-free media for imaging. Samples were imaged on a Nikon Ti2e microscope with fiber-optic coupled illumination source using a 60× 1.27 NA objective and sCMOS camera. 561 nm light with an integrated intensity of approx. 500 mW at the coverslip was used to stimulate emission of the fluorophore. Images were collected every 10 msec for 2 seconds per field of view. To test how sensitive to 405 nm light each dye variant was, each well was imaged multiple times with ascending 405 nm light intensity (between 0 and 5 mW at the coverslip). Approximately 60 fields of view were collected per cell-line/dye compound set.

To measure Example 19, where the fluorophore was a Si-containing far-red emission dye, a 642 nm light (approx. 500 mW at the coverslip) was used to stimulate emission of the fluorophore rather than the 561 nm lightsource, and cells were stained with 100 nM Potomac Yellow rather than Potomac Red.

After acquiring images for each compound, the images were individually inspected to qualitatively assess the performance of each test compound. It will be understood by those skilled in the art that modification of the PA-$JF_{549}$ core structure can alter not only dye properties, but also photoactivation at 405 nm light; accordingly, performance of each dye variant, which is not predictable based on structural features alone, was assessed as follows. Compounds that were obviously inappropriate for single-molecule imaging (such as those that cause dye aggregation inside the cell) were flagged and removed from subsequent analysis. The remaining dyes that reliably yielded spots consisting of a single fluorophore, and were thus quantifiable using a single-molecule detection algorithm, were further processed to generate individual trajectories. All frames from each field of view were analyzed using a maximum likelihood estimator model to detect single molecule fluorescence emissions within an image with sub-pixel precision. Individual detections were subsequently connected into trajectories across sequential camera frames. Statistics generated from the detections (e.g. signal-to-noise) and tracks (e.g. number of tracks) were used to compare between dye variants.

The number of nuclear trajectories in the ER-Halo cell line was determined for each test compound at each level of 405 nm photoactivation. In order to set a common baseline between the different test compounds, the photoactivation condition where the number of nuclear tracks most closely matched that of JF549 was selected for each test compound, and this condition was used for all subsequent comparisons.

TABLE 4a

| Specificity Factor (all values) | | |
|---|---|---|
| Example | Fold reduction in nonspecific labeling | Sensitivity to 405 nm Photoactivation |
| PA-$JF_{549}$ | 1 | +++ |
| 1 | >10 | +++ |
| 2 | >10 | – |
| 3 | 1-5 | ++ |
| 4 | >10 | ++ |
| 5 | >10 | + |
| 6 | 1-5 | ++ |
| 7 | >10 | – |
| 8 | 5-10 | +++ |
| 9 | >10 | +++ |
| 10 | 5-10 | +++ |
| 11 | 1-5 | – |
| 12 | >10 | – |
| 13 | 5-10 | + |
| 14 | >10 | – |
| 15 | 5-10 | – |
| 16 | 5-10 | ++ |
| 17 | 1-5 | +++ |
| 18 | >10 | – |

For definition of –; +; ++; +++, see Example 32.

TABLE 4b

| Specificity Factor (all values) | | |
|---|---|---|
| Example | Fold reduction in nonspecific labeling | Sensitivity to 405 nm Photoactivation |
| PA-$JF_{549}$ | 1 | +++ |
| 1 | >10 | +++ |
| 2 | >10 | – |
| 3 | 1-5 | ++ |
| 4 | >10 | ++ |
| 5 | >10 | + |
| 6 | 1-5 | ++ |
| 7 | >10 | – |
| 8 | 5-10 | +++ |
| 9 | >10 | +++ |
| 10 | 5-10 | +++ |
| 11 | 1-5 | – |
| 12 | >10 | – |
| 13 | 5-10 | + |
| 14 | >10 | – |
| 15 | 5-10 | – |
| 16 | 5-10 | ++ |
| 17 | 1-5 | +++ |
| 18 | >10 | +++ |
| 19 | >10 | +++ |
| 20 | >10 | – |
| 21 | 5-10 | – |
| 22 | 5-10 | – |
| 23 | >10 | +++ |
| 24 | 1-5 | +++ |

For definition of –; +; ++; +++, see Example 32.

9.32 Example 32: Labelling Specificity Improvement

Using the methods described in Tables 4a and 4b above, labelling specificity of the compound of Examples 1-24 was measured and compared to PA-$JF_{549}$. U2OS cells wild type or expressing ER-HaloTag fusion were incubated with PA-$JF_{549}$ or Examples 1-24 for 1 hr. FIG. 5 shows an example field of view ER-HaloTag Fusion expressing U2OS, co-stained with Potomac Red (CAS: 2127150-65-4; Grimm et al., 2017). Labeling specificity, as measured by the fold reduction in nonspecific labeling of WT cells, was calculated by number of tracks measured in WT cells for Examples 1-24 compared to the number of tracks in WT cells for PA-$JF_{549}$, expressed as the ratio with PA-$JF_{549}$ in the numerator.

Sensitivity for photoconversion under 405 nm illumination was determined qualitatively based on how much 405 nm light was required to achieve comparable numbers of tracks. Compounds which demonstrated high levels of activation with 0.25 mW of 405 nm laser input (the minimum intensity tested) received "+++", whereas those compounds that were unable to achieve high levels of activation at 5 mW 405 nm intensity received "–". A "+" and "++" were assigned to compounds that needed more than 1 and 2.5 mW of 405 nm laser power at the objective, respectively.

SNR, which is a proxy for single molecule brightness, was calculated for Examples 1-4 (see FIG. 6). Each spot in the SPT experiment described in Example 31 was calculated using a log likelihood ratio test for the presence of a 2D Gaussian spot. See Serge et al., "Dynamic multiple-target tracing to probe spatiotemporal cartography of cell membranes," *Nat. Methods* 2008, 5(8), 687-694 (Serge et al., 2008). The SNR of each spot was reported as its peak log likelihood ratio. This calculation uses a fixed-width 2D Gaussian PSF model with sigma/standard deviation equal to 0.183 μm. Only spots with SNR≥14 are included in this calculation, due to the stringency of the spot detection filter. The bars in FIG. 6 are the mean SNR calculated for all detections from a dye variant, aggregated across biological replicates, while the error bars are the standard error of the mean SNR across biological replicates. The above examples show that the compounds disclosed herein show surprisingly improved labeling specificity while maintaining brightness and control of density when used for labeling proteins.

A number of references have been cited, the disclosures of each of which are incorporated herein by reference in their entirety for all intent and purposes.

What is claimed is:

1. A compound, having a structure of Formula (IV):

(IV)

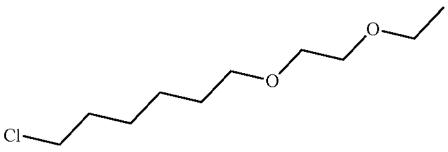

-continued

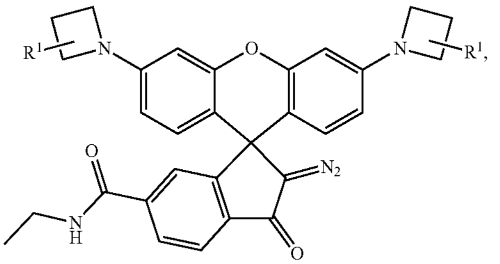

wherein $R^1$ is —OH, —C(=O)OH, —C(=O)O($C_{1-3}$ alkyl), —C(=O)N($C_{1-3}$ alkyl)$_2$, —N($C_{1-3}$ alkyl)$_2$, —$(CH_2)_n$O($C_{1-3}$ alkyl),

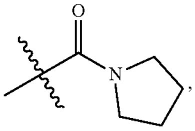,
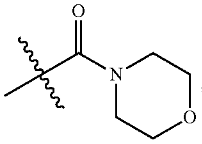, or

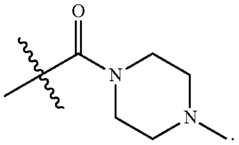.

2. The compound of claim 1, wherein $R^1$ is —N($CH_3$)$_2$, —OH,

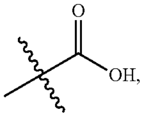
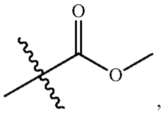,
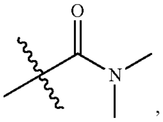,

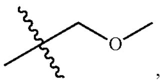,
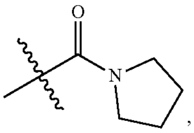,

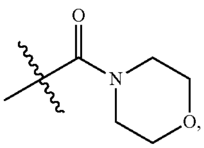, or
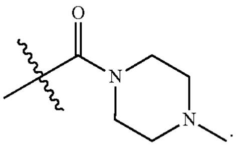.

3. The compound of claim 1, having a structure of Formula (V):

(V)
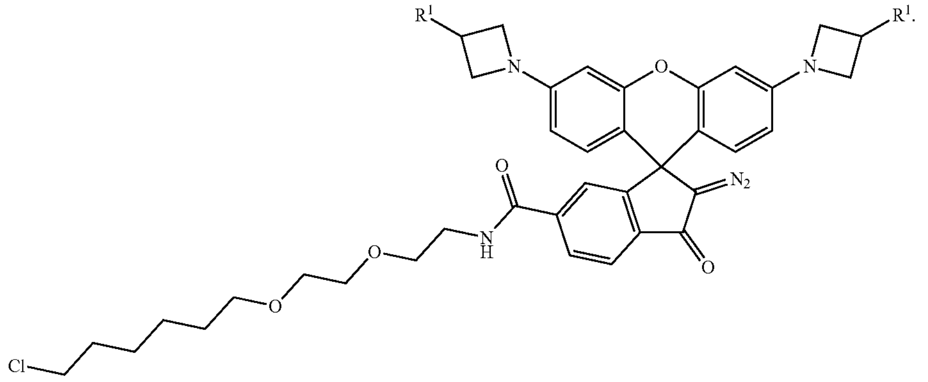
4. The compound of claim 2, wherein $R^1$ is —$N(CH_3)_2$, —OH,
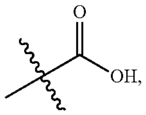 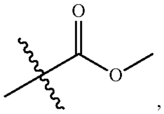, 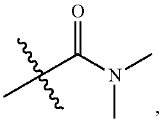,
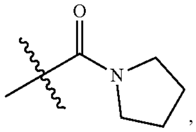, 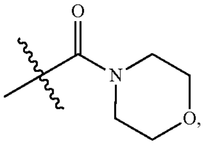
-continued
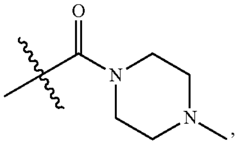, or 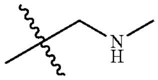.
5. The compound of claim 1, wherein the compound is:
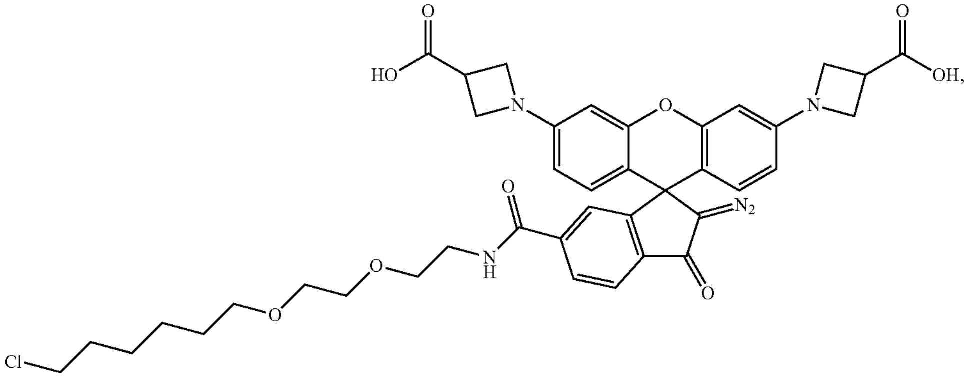
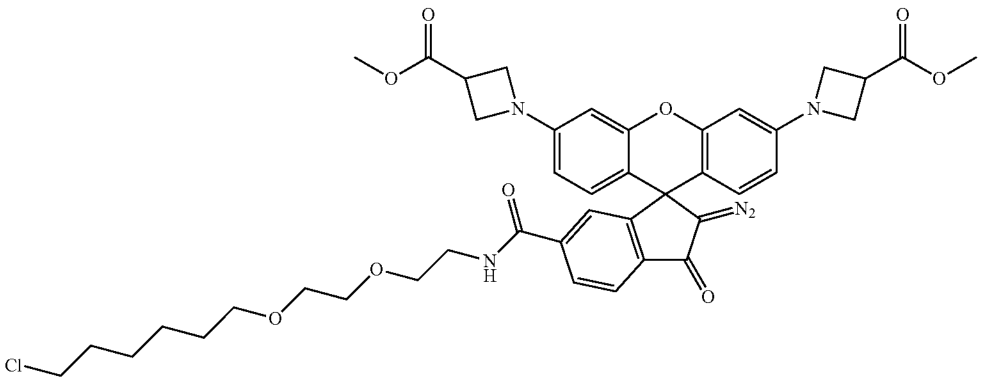, -continued
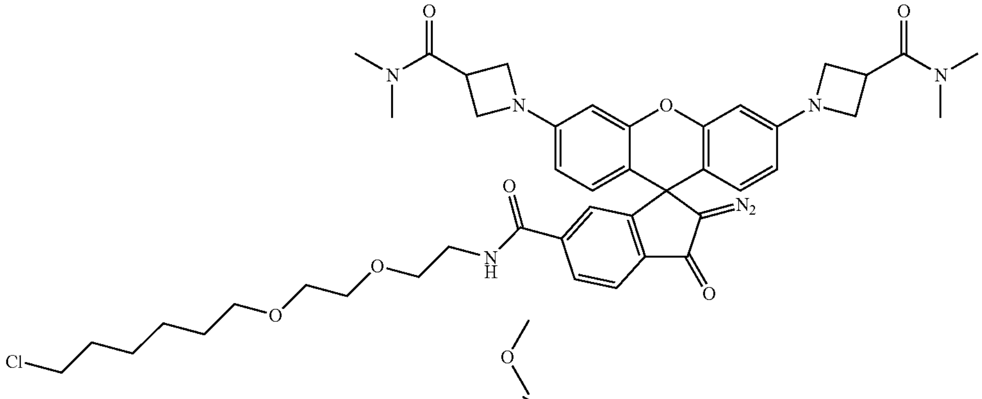
,
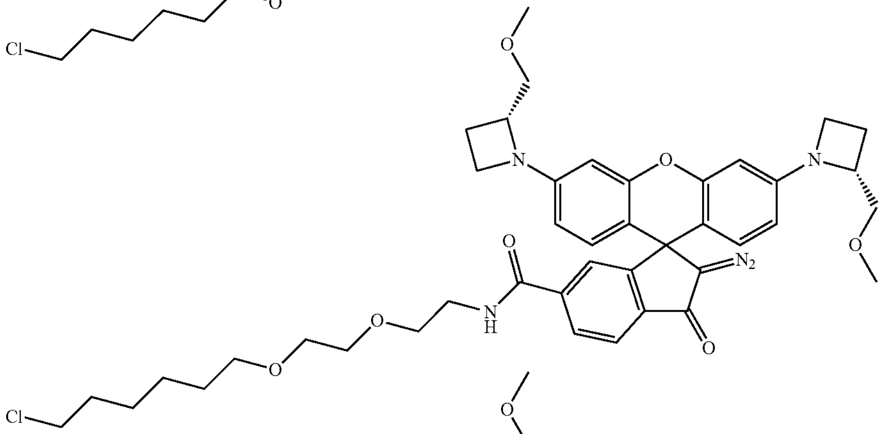
,
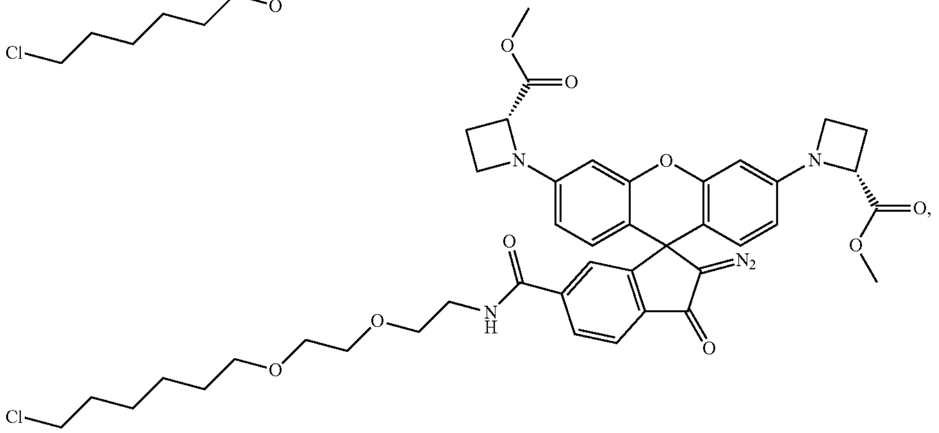
or
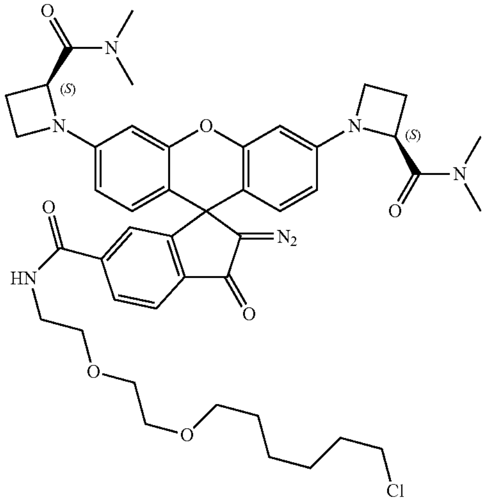
.

6. The compound of claim 1, wherein the compound is:
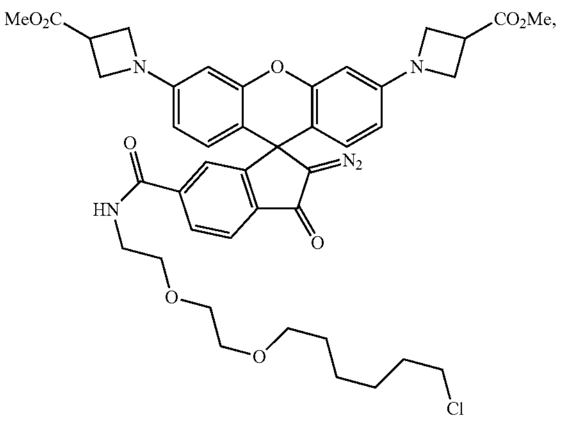
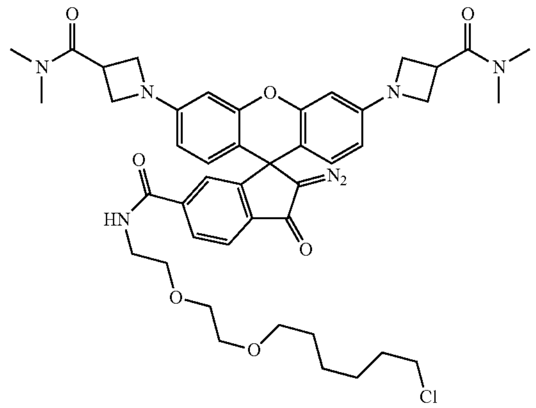
, or
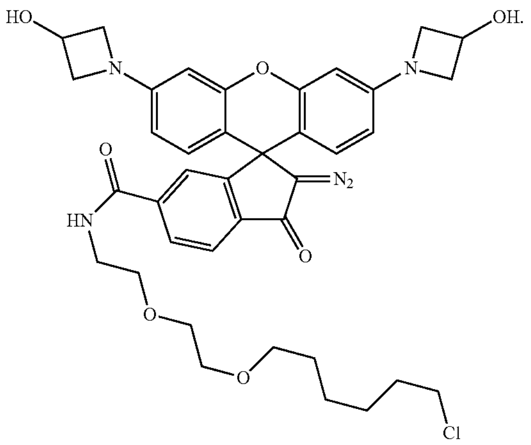
7. A compound having the following structure:
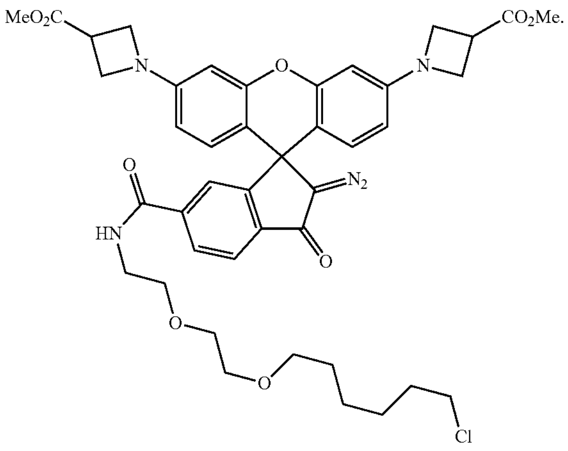
8. A compound having the following structure:
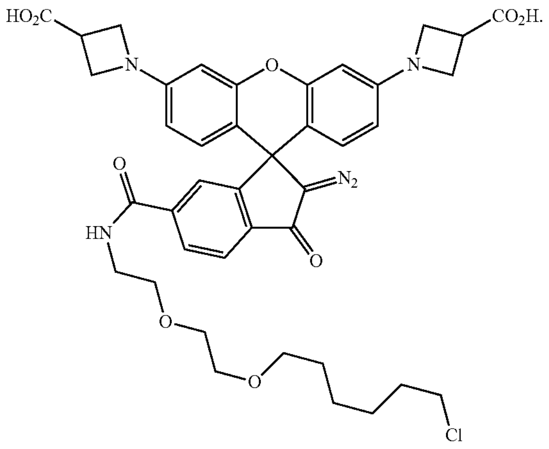
9. A compound having the following structure:
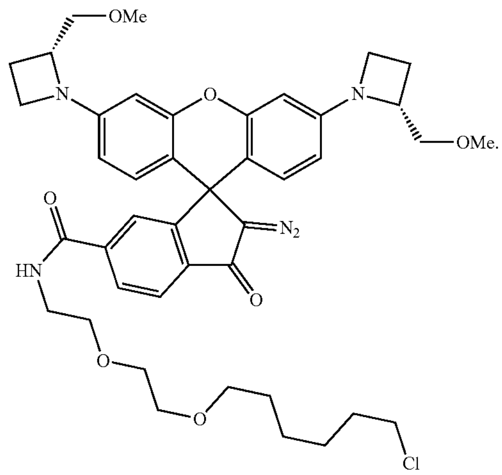

10. A compound having the following structure:
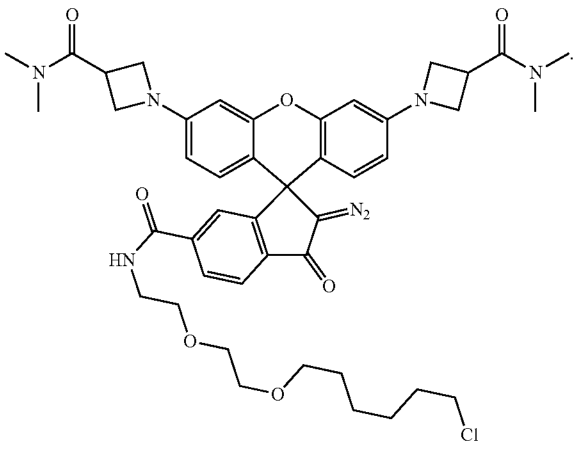
* * * * *